US012594263B2

(12) United States Patent
Gosling et al.

(10) Patent No.: US 12,594,263 B2
(45) Date of Patent: *Apr. 7, 2026

(54) CBL INHIBITORS AND COMPOSITIONS FOR EXPANSION OF IMMUNE CELLS

(71) Applicant: Nurix Therapeutics, Inc., San Francisco, CA (US)

(72) Inventors: Jennifa Gosling, San Francisco, CA (US); Arthur T. Sands, San Francisco, CA (US); Sarah Anne Whelan, San Francisco, CA (US); Michael Lotze, San Francisco, CA (US)

(73) Assignee: NURIX THERAPEUTICS, INC., San Francisco, CA (US)

(*) Notice: Subject to any disclaimer, the term of this patent is extended or adjusted under 35 U.S.C. 154(b) by 587 days.

This patent is subject to a terminal disclaimer.

(21) Appl. No.: 17/030,258

(22) Filed: Sep. 23, 2020

(65) Prior Publication Data

US 2021/0085717 A1 Mar. 25, 2021

Related U.S. Application Data

(60) Provisional application No. 63/032,462, filed on May 29, 2020, provisional application No. 62/978,254, (Continued)

(51) Int. Cl.
*A61K 31/4196* (2006.01)
*A61K 31/454* (2006.01)
(Continued)

(52) U.S. Cl.
CPC ........ *A61K 31/4196* (2013.01); *A61K 31/454* (2013.01); *A61K 31/4545* (2013.01);
(Continued)

(58) Field of Classification Search
CPC .. A61K 35/17; A61K 31/4196; A61K 31/454; A61K 31/4545; A61K 31/506;
(Continued)

(56) References Cited

U.S. PATENT DOCUMENTS 5,273,986 A 12/1993 Holland et al.
8,809,288 B2 * 8/2014 Baier ...................... A61P 35/02 536/23.1
(Continued)

FOREIGN PATENT DOCUMENTS

EP 1 364 949 A1 11/2003
EP 3 254 701 A1 12/2017
(Continued)

OTHER PUBLICATIONS

Vera, J.F., et al (2010) Accelerated production of antigen-specific T-cells for pre-clinical applications using Gas-permeable rapid expansion cultureware (G-Rex) J. Immunother 33(3); 305-315 (Year: 2010).*
(Continued)

*Primary Examiner* — Scarlett Y Goon
*Assistant Examiner* — Audrey L Buttice
(74) *Attorney, Agent, or Firm* — Squire Patton Boggs (US) LLP

(57) ABSTRACT

Methods and compositions using novel Cbl inhibitors enhancing expansion of immune cells to increase the efficacy of cell-based immunotherapeutics are disclosed. Also provided are cell-based immunotherapy methods and compositions.

31 Claims, 28 Drawing Sheets

Related U.S. Application Data filed on Feb. 18, 2020, provisional application No. 62/961,596, filed on Jan. 15, 2020, provisional application No. 62/954,323, filed on Dec. 27, 2019, provisional application No. 62/905,124, filed on Sep. 24, 2019.

(51) Int. Cl.

| | |
|---|---|
| ***A61K 31/4545*** | (2006.01) |
| ***A61K 31/506*** | (2006.01) |
| ***A61K 31/5377*** | (2006.01) |
| ***A61K 35/17*** | (2025.01) |
| ***A61K 40/11*** | (2025.01) |
| ***A61K 40/31*** | (2025.01) |
| ***A61K 40/42*** | (2025.01) |
| ***A61K 45/06*** | (2006.01) |
| ***A61P 35/00*** | (2006.01) |
| ***A61P 37/04*** | (2006.01) |
| ***C12N 5/0783*** | (2010.01) |

(52) U.S. Cl.

CPC ........ *A61K 31/506* (2013.01); *A61K 31/5377* (2013.01); *A61K 35/17* (2013.01); *A61K 40/11* (2025.01); *A61K 40/31* (2025.01); *A61K 40/42* (2025.01); *A61K 45/06* (2013.01); *A61P 35/00* (2018.01); *A61P 37/04* (2018.01); *C12N 5/0636* (2013.01); *C12N 2501/2302* (2013.01); *C12N 2501/2307* (2013.01); *C12N 2501/2315* (2013.01); *C12N 2501/2321* (2013.01); *C12N 2501/72* (2013.01); *C12N 2506/11* (2013.01)

(58) Field of Classification Search

CPC .............. A61K 31/5377; A61K 31/713; A61K 31/5375; A61K 45/06; A61K 38/20; A61K 38/2013; A61K 38/2086; A61K 38/217; A61K 38/2046; A61K 2300/00; A61P 35/00; A61P 37/04; C12N 5/0636; C12N 2501/2302; C12N 2501/2307; C12N 2501/2315; C12N 2501/2321; C12N 2501/72; C12N 2506/11

See application file for complete search history.

(56) References Cited

U.S. PATENT DOCUMENTS

| | | | | |
|---|---|---|---|---|
| 9,334,522 | B2 * | 5/2016 | Gu ...................... | C12N 15/113 |
| 11,464,802 | B2 | 10/2022 | Sand et al. | |
| 11,530,229 | B2 | 12/2022 | Sands et al. | |
| 2007/0054355 | A1 | 3/2007 | Reiss et al. | |
| 2010/0260808 | A1 | 10/2010 | Baier et al. | |
| 2014/0010781 | A1 | 1/2014 | Lametschwandtner et al. | |
| 2017/0015655 | A1 | 1/2017 | Kaieda et al. | |
| 2018/0207201 | A1 * | 7/2018 | Wardell ............... | C12N 5/0636 |
| 2020/0323904 | A1 | 10/2020 | Sands et al. | |
| 2021/0053961 | A1 | 2/2021 | Sands et al. | |
| 2021/0053986 | A1 | 2/2021 | Sands et al. | |
| 2021/0085717 | A1 | 3/2021 | Gosling et al. | |
| 2021/0087259 | A1 | 3/2021 | Gosling et al. | |
| 2021/0087529 | A1 | 3/2021 | Gosling et al. | |
| 2021/0198280 | A1 | 7/2021 | Kelly et al. | |

FOREIGN PATENT DOCUMENTS

| | | | |
|---|---|---|---|
| WO | WO 2005/021532 | A1 | 3/2005 |
| WO | WO 2007/072225 | A2 | 6/2007 |
| WO | WO 2008/033403 | A2 | 3/2008 |
| WO | WO 2009/073905 | A2 | 6/2009 |
| WO | WO 2009/098144 | A1 | 8/2009 |
| WO | WO 2011/076725 | A1 | 6/2011 |
| WO | WO 2011/140488 | A1 | 11/2011 |
| WO | WO 2012/020008 | A1 | 2/2012 |
| WO | WO 2012/089736 | A1 | 7/2012 |
| WO | WO 2012/175513 | A1 | 12/2012 |
| WO | WO 2013/067264 | A1 | 5/2013 |
| WO | WO 2013/067274 | A1 | 5/2013 |
| WO | WO 2014/040965 | A1 | 3/2014 |
| WO | WO 2015/084998 | A1 | 6/2015 |
| WO | WO 2016/196776 | A2 | 12/2016 |
| WO | WO 2018/098275 | A1 | 5/2018 |
| WO | WO 2019/148005 | A1 | 8/2019 |
| WO | WO 2020/081450 | A1 | 4/2020 |
| WO | WO 2020/167518 | A1 | 8/2020 |
| WO | WO 2020/210508 | A1 | 10/2020 |
| WO | WO 2020/236654 | A1 | 11/2020 |
| WO | WO 2020/264398 | A1 | 12/2020 |
| WO | WO 2021/021761 | A1 | 2/2021 |
| WO | WO 2021/061853 | A1 | 4/2021 |
| WO | WO 2021/061870 | A1 | 4/2021 |
| WO | WO 2021/091575 | A1 | 5/2021 |
| WO | WO 2021/113557 | A1 | 6/2021 |

OTHER PUBLICATIONS

Agarwal, S., et al (2016) Abstract 2228: Cbl-b inhibitors as novel intra-cellular checkpoint inhibitors for cancer immunotherapy Cancer Research 76(14 Supplemental); 222-2228; abstract and poster (Year: 2016).*

Bajgain, P., et al (2014) Optimizing the production of suspension cells using the G-Rex "M" series Methods & Clinical development 1(14015); 1-9 (Year: 2014).*

G-Rex Brochure by Wilson Wolf Manufacturing, Rev. 151030 (Year: NA) (Year: NA).*

Bajgain, P., et al.(2014) Methods & Clinical development 1(14015); 1-9 Supplemental materials, 1 page (Year: 2014).*

International Search Report and Written Opinion for International Patent Application PCT/US2019/015250, 10 pages, Jun. 11, 2019.

International Search Report and Written Opinion for International Patent Application PCT/US2019/056112, 8 pages, Dec. 6, 2019.

International Search Report and Written Opinion for International Patent Application PCT/US2020/016489, 8 pages, May 27, 2020.

International Search Report and Written Opinion for International Patent Application PCT/US2020/033274, 19 pages, Oct. 23, 2020.

International Search Report and Written Opinion for International Patent Application PCT/US2020/027492, 21 pages, Aug. 11, 2020.

International Search Report and Written Opinion for International Patent Application PCT/US2020/039957, 20 pages, Oct. 5, 2020.

International Search Report and Written Opinion for International Patent Application PCT/US2020/043788, 13 pages, Oct. 23, 2020.

Riling et al.: "Abstract A206: Small-molecule Cbl-b inhibitors as novel intracellular checkpoint inhibitors for cancer immunotherapy I Molecular Cancer Therapeutics", Jan. 1, 2018 (Jan. 1, 2018), XP055700949, Retrieved from the Internet:URL:https:// mct.aacrjournals.org/content/17/1_Supplement/A206 [retrieved on Jun. 4, 2020].

Gosling et al.: "Abstract 2696: Genetic and pharmacologic evaluation of the ubiquitin ligase CBL-B as a small-molecule, tumor immunotherapy target I Cancer Research", Apr. 3, 2019 (Apr. 3, 2019), XP055701108, Retrieved from the Internet: U RL:https:// cancerres.aacrjournals.org/content/79/13_Supplement/2696 [retrieved on Jun. 4, 2020].

Baboo J et al. The Impact of Varying Cooling and Thawing Rates on the Quality of Cryopreserved Human Peripheral Blood T Cells. Scientific Reports 2019 9:3417 1-13. (Year: 2019).

Bachmaier, K. et al. Negative regulation of lymphocyte activation and autoimmunity by the molecular adaptor Cbl-b. Nature, 2000, 403(6766):211-216 (Year: 2000).

Beavis RC et al. Peptide Mass Calculator Peptide Protein Research Ltd. https://www.peptidesynthetics.co.uk/tools/ (Year: 2023).

Extended European Search Report for European Patent Application No. 19744118.1, 12 pages dated Sep. 22, 2021.

Flynn JK et al. Stem memory T cells (TSCM)—their role in cancer and HIV immunotherapies. Clin Transl Immunology. 2014 3(7): e20. (Year: 2014).

(56) References Cited

OTHER PUBLICATIONS

International Search Report and Written Opinion for International Patent Application PCT/US2020/052317, 12 pages, Jan. 14, 2021.
International Search Report and Written Opinion for International Patent Application PCT/US2020/063176 12 pages, Mar. 5, 2021.
International Search Report and Written Opinion for International Patent Application PCT/US2020/052335, 12 pages, Apr. 1, 2021.
Jack et al., "Gene Expression and Linkage Analysis Implicate CBLB as a mediator of rituximab resistance", The Pharmacogenomics Journal (2018) 18: 467-473; doi: 10.1038/tpj2017.41.
Jeon et al. Essential Role of the E3 Ubiquitin Ligase Cbl-b in T Cell Anergy Induction. Immunity, 2004 21(2):167-177 (Year: 2004).
Lewis MD et al. A reproducible method for the expansion of mouse CD8 + T lymphocytes. J Immunol Methods. 2015 417: 134-138 (Year: 2015).
Loeser S et al. Spontaneous tumor rejection by cbl-b-deficient CD8+ T cells. Exp Med. 2007 204(4): 879-891 (Year: 2007).
Sachet M et al. Treatment of a cancer patient by an adoptive cell therapy protocol combining DC vaccination with cbl-b ex vivo silencing. Journal for ImmunoTherapy of Cancer 2015, 3(Suppl 2):P172. (Year: 2015).
Sharma R et al. Physiology, Blood Volume. In: StatPearls. Treasure Island (FL): StatPearls Publishing; Jan. 2022 www.ncbi.nlm.nih.gov/books/NBK526077/?report=classic) (Year: 2022).
Stewart et al., "Efforts toward elucidating Thalidomide's molecular target: an expedient synthesis of the first Thalidomide biotin analogue", Org. Biomol. Chem., 2010, 8:4059-4062.
Tigno-Aranjuez et al., "Inhibition of RIP2's tyrosine kinase activity limits NOD2-driven cytokine responses", Genes & Development, 2010, 24:2666-2677; http://www.genesdev.org/cgi/doi/10.1101/gad.964410.
Triozzi P et al. Phase I clinical trial of adoptive cellular immunotherapy with APN401 in patients with solid tumors. Journal for ImmunoTherapy of Cancer 2015, 3(Suppl 2):P175 (Year: 2015).
International Search Report and Written Opinion for International Patent Application PCT/US2019/060584, 11 pages, May 14, 2021.
Bondeson et al., "Catalytic in vivo protein knockdown by small-molecule PROTACs", Nature Chemical Biology, published online Jun. 10, 2015; DOI: 10.1038/NCHEMBIO.1858.
Good et al., Proliferative tracing with single-cell mass cytometry optimizes generation of stem cell memory-like T cells, Nature Biotechnology Mar. 2019; 37(3): 259-266. DOI:10.1038/s41587-019-0033-2.
Howe et al, "Models of Energy in the Human Jurkat T Cell Line", Assay and Drug Development Technologies, vol. 1, No. 4, 2003, pp. 537-544.
Johnson et al., "Relationships between drug activity in NCI preclinical in vitro and in vivo models and early clinical trials", British Journal of Cancer (2001) 64(10): 1424-1431.
Marelli et al., Tumor targeting via integrin ligands, Frontiers in Oncology, vol. 3, Article 222, pp. 1-12, 2013.
Marshall et al., "Superior Activity of the Type C Class of ISS In Vitro and In Vivo Across Multiple Species", DNA and Cell Biology, vol. 24, No. 2, 2005, pp. 63-72.
Pearce et al., "Failure modes in anticancer drug discovery and development", Cancer Drug Design and Discovery Edited by Stephen Neidle, Chapter 18, pp. 424-435 (2008).
Wang et al., Mathematical modeling in cancer drug discovery, Drug Discovery Today, vol. 19, No. 2, pp. 145-150, 2014.
Yang et al., "Exploiting Synthetic Lethality for the Therapy of ABC Diffuse Large B Cell Lymphoma", Cancer Cell, 21, 2012, pp. 723-737, DOI 10.1016/j.ccr.2012.05.024.
Ye et al., "Engineered Artificial Antigen Presenting Cells Facilitate Direct and Efficient Expansion of Tumor Infiltrating Lymphocytes", Journal of Translation Medicine 2011, 9:131, 13 pages.
Triozzi, et al., "Phase I clinical trial of adoptive cellular immunotherapy with APN401 in patients with solid tumors", Journal for ImmunoTherapy of Cancer; vol. 3(2), Supplement 2; p. 175; Article No. P230 (2015) SITC 2015 (Year: 2015).
Liyasova, et al., "Molecular Pathways: CBL Proteins in Tumorigenesis and Antitumor Immunity-Opportunities for Cancer Treatment", Clinical Cancer Research; 21(8) 1789-1794.
Slastnikova, et al., "Targeted Intracellular Delivery of Antibodies: The State of the Art", Frontiers in Pharmacology; Oct. 24, 2018; doi: 10.3389/fphar.2018.01208. eCollection 2018.

* cited by examiner

CBL INHIBITORS AND COMPOSITIONS FOR EXPANSION OF IMMUNE CELLS

CROSS-REFERENCE

The present application claims the benefit of U.S. provisional application nos. 62/905,124, filed Sep. 24, 2019, 62/954,323, filed Dec. 27, 2019, 62/961,596, filed Jan. 15, 2020, 62/978,254, filed Feb. 18, 2020, and 63/032,462, filed May 29, 2020, the contents of each of which are hereby incorporated in their entireties.

FIELD OF THE INVENTION

Provided herein are methods relating to use of Cbl inhibitors in cell-based immunotherapies. The methods and compositions of the disclosure are useful, for example, for the preparation of immune cell compositions and their use for the treatment of T cell dysfunction and cancers.

BACKGROUND

Cbl (Casitas B-lineage Lymphoma) proteins are part of a family of ubiquitin ligases involved in cell signaling, protein ubiquitination, and degradation of protein substrates. Members of the family include the RING-type E3 ligases cCbl, Cbl-b, and Cbl-c. Cbl-b plays an important role in the immune system due to its function as a negative regulator of immune activation. Cbl-b is highly expressed in human CD4+ and CD8+ T cells, with expression tightly regulated by CD28 and CTLA-4 and other co-stimulatory and inhibitory signals. See Lutz-Nicoladoni et al., *Frontiers in Oncology,* 5(58):1-14 (2015).

Cbl-b plays an essential role in the negative regulation of T cell activation. T cells conventionally require two signals for activation, the first provided by interaction of the T-cell receptor with a peptide presented by an MHC molecule, and the second through co-stimulatory molecules on antigen-presenting cells. Cbl-b plays a prominent role in the activation and effector functions of NK cells. In B cells, Cbl-b is recruited to the clustered B cell antigen receptor (BCR), and is required for entry of endocytosed BCRs into late endosomes. See Veselits et al., *PLOS One,* 9(3):e89792 (2014). Cbl-b's activity in myeloid cells is not fully characterized, but includes a role in negative-feedback loops of TLR signaling and regulates macrophage activation by fatty acids.

Studies have found that Cbl-b-deficient T cells display lower thresholds for activation by antigen recognition receptors and co-stimulatory molecules (e.g., CD28). For example, loss of Cbl-b in T cells uncouples the requirement for CD28 costimulation during T-cell activation and proliferation. See Bachmaier, K. et al., *Nature,* 403(6766):211-216 (2000). Such Cbl-$b^{-/-}$ T cells are largely resistant to T-cell anergy, a tolerance mechanism in which T cells are functionally inactivated and T-cell proliferation is greatly impaired. See Jeon et al., *Immunity,* 21(2):167-177 (2004) and Schwartz et al., *Annu Rev Immunol.,* 21:305-34 (2003). Evidence supporting this proposition includes the fact that loss of Cbl-b in cbl-b knockout mice results in impaired induction of T-cell tolerance and exacerbated autoimmunity. See Jeon et al., *Immunity,* 21(2):167-177 (2004). Importantly, loss of Cbl-b in mice also resulted in a robust anti-tumor response that depends primarily on cytotoxic T cells. One study showed that Cbl-$b^{-}$/− CD8+ T cells are resistant to T regulatory cell-mediated suppression and exhibit enhanced activation and tumor infiltration. Therapeutic transfer of naive Cbl-$b^{-/-}$ CD8+ T cells was sufficient to mediate rejection of established tumors. See Loeser et al., *J. Exp. Med.,* 204(4):879-891 (2007). Recent studies have shown that Cbl-b also plays a role in NK cell activation. Genetic deletion of Cbl-b or targeted inactivation of its E3 ligase activity allowed NK cells to spontaneously reject metastatic tumors in a mouse model. See Paolino et al., *Nature,* 507(7493):508-512.

Adoptive Cell Therapy (ACT) is used in otherwise treatment-resistant cancers, including metastatic melanomas, gliomas, and renal carcinomas. In ACT, NK cells or T cells from a patient's own blood or tumor tissue are harvested, then grown into large numbers in the laboratory, and then the expanded cells are transferred back to the patient to enhance the patient's immune system response to the cancer. In some versions of ACT, the T cells or NK cells are modified using genetic engineering to enable them to target the patient's cancer cells and kill the cancer cells more efficiently. Types of adoptive cell therapy include natural killer (NK) cell therapy, tumor-infiltrating lymphocyte (TIL) therapy, engineered T-cell receptor therapy (TCR), and chimeric antigen receptor T-cell (CAR T) therapy.

As the name implies, NK cell therapy uses NK cells, part of the innate immune system, and the first line of defense against infections and diseases, including cancer cells. NK cells are an attractive tool for cell-based immunotherapy because of their innate ability to discriminate between healthy and virally infected or naturally transformed cells. NK cell therapies include adoptive autologous or allogeneic cell therapy, wherein NK cells are used to support hematopoietic stem cell transplants. The cells are obtained from the patient prior to treatment, from related donors, or are allogeneic NK cells that are partially HLA-matched. Adoptive transferred cell therapy is also used with NK cells from a donor, the patient, cord blood, differentiated induced pluripotent stem cells, or from hematopoietic stem cells.

TIL therapy involves the isolation and expansion of TIL from a patient's tumor tissue. Infiltrating immune cells can function to control tumor growth and progression, but paradoxically can also help to create an immunosuppressive environment in which the tumor can thrive. See, Schreiber, *Science;* 331(6024):1565-70(2011). An important mechanism of tumor immune evasion is the expression of immune checkpoint modulators such as CTLA-4 and PD-L1, both on tumor cells and on infiltrating immune cells. By blocking these signaling pathways, immune checkpoint inhibitors can re-activate the host immune system to recognize and control the tumor; this is the mechanism of action of several current therapies. See, Pardoll, *Nat. Rev. Cancer,* 12(4):252-64 (2012), and Salgado et al., *Adv. Anat. Pathol.,* 24(5):235-251, and 24(6):311-335 (2017)).

LN-145 therapy, which has been granted Breakthrough Therapy designation by the FDA, is a TIL therapy for the treatment of patients with recurrent, metastatic, or persistent cervical cancer. In an LN-145 therapy Phase II clinical study, tumor tissue is surgically isolated from a patient, sent to a GMP facility where TIL are isolated and expanded over a three-week period. One week prior to infusion, the patient is given preconditioning therapy comprising administration of cyclophosphamide IV on days −8 and −7, fludarabine IV on days −6 to −2, and pembrolizumab (a humanized anti-PD-1 antibody) on day −1. The patient then receives the autologous expanded TIL, followed by aldesleukin IV on days +1 to +4. The patient then receives a cycle of pembrolizumab every 21 days for 12 months in the absence of disease progression or unacceptable toxicity.

TCR therapy involves the genetic engineering of T cells to express affinity-enhanced, tumor-specific T cell receptor (TCR) genes and thereby kill cancer cells. Briefly, autologous T cells are collected via apheresis and transformed in vitro, e.g., using a lentiviral vector, to express T cells recognizing a specific tumor antigen. The transformed cells are expanded in vitro before being infused into the patient. Seven days prior to reinfusion, patients receive low-dose cyclophosphamide, and low dose fludarabine for lymphocyte clearance. After infusion of expanded TCR-T cells (either once or in stages), IL-2 is administered subcutaneously (250,000 IU/twice/day) for 14 days. This therapy is effective but can cause adverse effects if the antigen is also expressed in healthy tissues.

Chimeric Antigen Receptor Therapy (CAR T) uses a patient's T cells, which are harvested and genetically engineered to express a chimeric T cell receptor comprised of an antigen binding domain, typically a single-chain variable fragment and additional intracellular costimulatory domains from receptors, such as CD19, CD28 or CD137. One advantage of CAR T-based cell therapies is that a CAR T cell can bind to a cancer cell even in the absence of the recognized antigen being expressed on the MHC (in contrast to TIL- and TCR-based cell therapies). CAR T-based cell therapies have been FDA approved for the treatment of relapsed cancers. For example, KYMRIAH® (tisagenlecleucel) is FDA-approved for the treatment of relapsed/refractory B-cell Acute Lymphoblastic Leukemia (B-cell ALL) in children and young adults. Patient T cells are removed and transduced using a lentiviral vector to express a CAR with a murine anti-CD19 single chain antibody fragment (scFv) and an intracellular portion that contains T cell signaling (CD3-ζ) and co-stimulatory (4-1B) domains. Axicabtagene ciloleucel (YESCARTA®) is an FDA-approved CAR T-based cell therapy for adults with large-B cell lymphomas whose cancer has progressed after receiving at least two prior treatment regimens. T cells are removed from the patient via leukapheresis, transduced in vitro to express a CAR with a murine single chain variable fragment (scFv) with specificity for CD19 linked to two signaling domains derived from CD3-ζ and CD28 genes.

Current CAR T-based cell therapy has a number of limitations. It may not be an effective therapy in patients with too few T cells to donate. Cross reactivity with normal cells expressing the target antigen can also be problematic. In addition, approximately 30-50% of patients with large B cell lymphomas who achieve remission at one month with CD19 CAR T cells eventually relapse. See, Shah and Fry, *Nat. Rev. Clin. Oncol.* 16:372-385 (2019). Finally, CAR T-based cell therapy has shown low efficacy against solid tumors.

CAR-NK cell therapy involves selective expansion of NK starting material, from patient cord blood, a healthy donor, stem cells, or an NK-derived cell line. NK cells are enriched within a cell population by depletion of CD3+ T cells and positive selection of CD56+ cells, and then selectively expanded in the presence of feeder cells and cytokines, including IL-2, IL-7, IL-15, IL-21, IL-12, and IL-18. Next, they are subjected to genetic engineering, e.g., using a lentiviral vector, retroviral vector or retrovirus, transposons or CRISPR, before final expansion in the presence of IL-2. Cells are once again depleted of CD3+ T cells and formulated for infusion into the patient or cryopreserved for future infusion. See, Trager, Cell and Gene Therapy Insights, 5(5):585-600 (2011). A recent phase 1 and 2 trial of allogeneic CAR-NK cells demonstrated complete remission of lymphoma or chronic lymphocytic leukemia in 7 of 11 patients. See Liu et al., 2020, *N. Engl. J. Med.* 382:545-553.

Notwithstanding the promise of the above-described cell-based immunotherapies, many patients are not able to benefit from them because of the inability to collect or manufacture immune cells, especially from intensively treated subjects with low counts of immune cells that are defective at baseline. Even for patients where sufficient numbers of immune cells can be manufactured, their clinical outcomes can be improved by improving engraftment of the effused immune cells or increasing the durability of their response. Therefore, more effective immune cell therapies are needed.

SUMMARY OF INVENTION

In several aspects, provided herein are methods and compositions for the enhancement of cell therapy with Cbl inhibitors. In certain embodiments, the Cbl inhibitors enhance expansion of immune cells in vivo prior to harvesting. In certain embodiments, the Cbl inhibitors enhance an initial expansion of immune cells ex vivo. In certain embodiments, the Cbl inhibitors enhance a rapid expansion of immune cells ex vivo. In certain embodiments, the Cbl inhibitors enhance an initial expansion of immune cells ex vivo and eliminate the need for a second, rapid expansion of the immune cells. In certain embodiments, the Cbl inhibitors can activate immune cells in the absence of co-stimulation. In certain embodiments, the Cbl inhibitors augment the benefits of receiving an infusion of immune cells to a patient in need thereof. The methods are useful, for example, for the treatment of T cell dysfunction and cancers. While not intending to be bound by a theory of operation, the methods are based, in part, on the discovery that Cbl inhibitors can enrich immune cell populations for memory cells, thereby enhancing the durability of the immune cell response in vivo and in vitro.

In one aspect, provided herein are methods of enhancing expansion of immune cells in vivo with a Cbl inhibitor. In another aspect, provided herein are methods of enhancing expansion of immune cells ex vivo with a Cbl inhibitor. In another aspect, provided herein are immune cells enhanced by methods provided herein. In another aspect, provided herein are compositions comprising the immune cells. In another aspect, provided herein are methods of treatment comprising administration of the immune cells or compositions. In another aspect, provided herein are methods of enhancing administration of immune cells or compositions by combination administration of a Cbl inhibitor. In yet another aspect, any or all of these aspects are combined.

Useful Cbl inhibitors include compounds that inhibit the activity of cCbl, Cbl-b, and/or Cbl-c enzymes. The Cbl inhibitors can be small molecules, peptides, antibodies, or nucleic acids. In certain embodiments, the Cbl inhibitor is a compound according to Formula (A):

Formula (A)

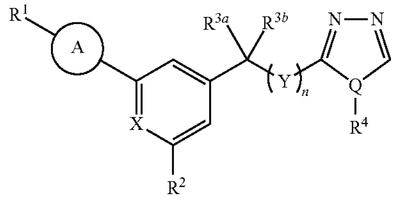

or a tautomer thereof, or a pharmaceutically acceptable salt of any of the foregoing, wherein:

$R^1$ is H, $C_1$-$C_6$ alkyl, $C_3$-$C_6$ cycloalkyl, 3- to 6-membered heterocyclyl, $C_1$-$C_6$ alkyl-($C_3$-$C_6$ cycloalkyl), $C_1$-$C_6$ alkyl-(3- to 6-membered heterocyclyl);

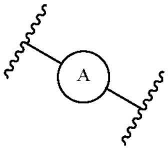
is
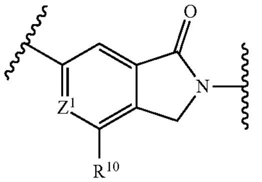
or
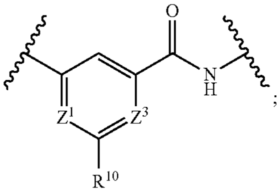
;

$Z^1$ is CH or N;

$Z^2$ is CH or N;

$Z^3$ is CH or N;

X is CH or N;

$R^2$ is H, halo, $C_3$-$C_6$ cycloalkyl, —NH-(3- to 6-membered heterocyclyl), —NH—($C_1$-$C_6$ alkyl), —NH—($C_3$-$C_6$ cycloalkyl), —O-(3- to 6-membered heterocyclyl), —O—($C_1$-$C_6$ alkyl), or —O—($C_3$-$C_6$ cycloalkyl);

$R^{3a}$ is H, halo, or $C_1$-$C_6$ alkyl;

$R^{3b}$ is H, halo, $C_1$-$C_6$ alkyl, or $C_3$-$C_6$ cycloalkyl; or $R^{3a}$ and $R^{3b}$ are taken together with the carbon atom to which they are attached to form a 4- to 8-membered heterocyclyl or a $C_3$-$C_6$ cycloalkyl, wherein the heterocyclyl or cycloalkyl are optionally substituted by 1-3 $R^{12}$ groups;

or $R^{3b}$ and $R^{11a}$ are taken together with the carbon atoms to which they are attached to form a $C_3$-$C_6$ cycloalkyl optionally substituted by $C_1$-$C_6$ alkyl;

n is 0 or 1;

Y is $C(R^{11a})(R^{11b})$ or S, with the optional proviso that if either or both of $R^{3a}$ and $R^{3b}$ are halo, Y is $C(R^{11a})(R^{11b})$;

Q is CH or N;

$R^4$ is H, $C_1$-$C_6$ alkyl, $C_1$-$C_6$ haloalkyl, or $C_3$-$C_6$ cycloalkyl;

$R^{10}$ is H, $C_1$-$C_6$ alkyl, $C_1$-$C_6$ haloalkyl, or $C_3$-$C_6$ cycloalkyl;

$R^{11a}$ and $R^{11b}$ are independently H, halo, $C_1$-$C_6$ alkyl, or $C_1$-$C_6$ haloalkyl; or $R^{11a}$ and $R^{11b}$ are taken together with the carbon atom to which they are attached to form a $C_3$-$C_6$ cycloalkyl; or $R^{3b}$ and $R^{11a}$ are taken together with the carbon atoms to which they are attached to form a $C_3$-$C_6$ cycloalkyl optionally substituted by $C_1$-$C_6$ alkyl; and each $R^{12}$ is independently $C_1$-$C_6$ alkyl, halo, hydroxy, —O($C_1$-$C_6$ alkyl), —CN, $C_1$-$C_6$ alkyl-CN, $C_1$-$C_6$ alkyl-OH, or $C_1$-$C_6$ haloalkyl; wherein two geminal $R^{12}$ groups can be taken together with the carbon atom to which they are attached to form a spiro $C_3$-$C_4$ cycloalkyl.

In certain embodiments, the Cbl inhibitor is selected from compounds 101-129 described herein. In some embodiments, the Cbl inhibitor is an antibody. In some embodiments, the Cbl inhibitor is a peptide. In some embodiments, the Cbl inhibitor is an siRNA.

In one aspect, provided herein are expansion methods, compositions, and cell therapy methods for treating a condition in a patient in need thereof. In certain embodiments, the methods comprise administering a Cbl inhibitor to a donor under conditions suitable to promote activation or expansion of immune cells in the donor. In certain embodiments, the methods further comprise harvesting circulating immune cells from the donor. In certain embodiments, the methods further comprise harvesting immune cells obtained from a tumor, or a portion thereof, from the donor. In certain embodiments, the methods further comprise genetically modifying the harvested immune cells. In certain embodiments, the methods further comprise expanding immune cells from said donor ex vivo in one or two steps. In certain embodiments, the first step is an expansion step. In certain embodiments, the second step is a rapid expansion step. In some embodiments, one or more expansion steps is in the presence of one or more Cbl inhibitors. In certain embodiments, the methods further comprise administering the immune cells to a patient in need thereof. In some embodiments, the administering is in combination with one or more Cbl inhibitors.

In another aspect, provided herein are expansion methods, compositions, and cell therapy methods for treating a condition in a patient in need thereof. In certain embodiments, the methods comprise harvesting a tumor, or a portion thereof, from a donor. In certain embodiments, the methods comprise administering a Cbl inhibitor to a donor under conditions suitable to promote activation or expansion of immune cells in the donor. In certain embodiments, the harvested cells are genetically modified. In certain embodiments, the methods further comprise expanding immune cells from said tumor ex vivo in one or two steps. In other embodiments, the methods comprise a second expansion step, for instance, a rapid expansion step. In certain embodiments, the methods further comprise administering the immune cells to a patient in need thereof.

In another aspect, provided herein are expansion methods, compositions, and cell therapy methods for treating a condition in a patient in need thereof. In certain embodiments, the methods comprise harvesting immune cells from a tumor, or a portion thereof, from a donor. In certain embodiments, the harvested cells are genetically modified. In certain embodiments, the methods further comprise expanding immune cells from said tumor ex vivo in one or two steps. In certain embodiments, the first step is an expansion step in the presence of a Cbl inhibitor. In certain embodiments, the first step in the presence of the Cbl inhibitor yields a sufficient number of effective immune cells so that no second, rapid expansion step is needed. In other embodiments, the method comprise a second expansion step, for instance, a rapid expansion step. In certain embodiments, the methods further comprise administering the immune cells to a patient in need thereof.

In another aspect, provided herein are expansion methods, compositions, and cell therapy methods for treating a condition in a patient in need thereof. In certain embodiments, the methods comprise harvesting immune cells from a tumor, or a portion thereof, from a donor. In certain embodiments, the harvested immune cells are genetically modified. In certain embodiments, the methods further comprise expanding immune cells from said tumor ex vivo in one or two steps. In certain embodiments, the first step is an expansion step. In certain embodiments, the methods comprise a second expansion step, for instance, a rapid expansion step, in the presence of a Cbl inhibitor. In certain embodiments, the methods further comprise administering the immune cells to a patient in need thereof.

In another aspect, provided herein are expansion methods, compositions, and cell therapy methods for treating a condition in a patient in need thereof. In certain embodiments, the methods comprise harvesting immune cells from a tumor, or a portion thereof, from a donor. In certain embodiments, the harvested immune cells are genetically modified. In certain embodiments, the methods further comprise expanding immune cells from said tumor ex vivo in one or two steps. In certain embodiments, the first step is an expansion step in. In other embodiments, the methods comprise a second expansion step, for instance, a rapid expansion step. In certain embodiments, the methods further comprise administering the immune cells to a patient in need thereof in combination with administering a sufficient amount of a Cbl inhibitor, for instance to enhance effectiveness of the immune cells. In certain embodiments, the Cbl inhibitor enhances durability of the immune cells. In certain embodiments, the Cbl inhibitor enhances engraftment of the immune cells.

In certain aspects, any of the above methods are combined. In certain embodiments, the methods comprise administering a Cbl inhibitor to a donor prior to harvesting, and administering expanded immune cells to a patient in need thereof in combination with a Cbl inhibitor. In certain embodiments, the methods comprise administering a Cbl inhibitor to a donor prior to harvesting and conducting a first expansion in the presence of a Cbl inhibitor. In certain embodiments, the methods comprise administering a Cbl inhibitor to a donor prior to harvesting, and conducting no second, rapid expansion. In certain embodiments, the methods comprise administering a Cbl inhibitor to a donor prior to harvesting, conducting a first expansion in the presence of a Cbl inhibitor, conducting no second, rapid expansion, and/or administering expanded immune cells to a patient in need thereof in combination with a Cbl inhibitor. In certain embodiments, the methods comprise conducting a first expansion in the presence of a Cbl inhibitor, and administering expanded immune cells to a patient in need thereof in combination with a Cbl inhibitor. In certain embodiments, the methods comprise administering a Cbl inhibitor to a donor prior to harvesting, conducting a first expansion in the presence of a Cbl inhibitor, and conducting no second, rapid expansion. In certain embodiments, the methods comprise administering a Cbl inhibitor to a donor prior to harvesting, conducting a first expansion in the presence of a Cbl inhibitor, and administering expanded immune cells to a patient in need thereof in combination with a Cbl inhibitor. In certain embodiments, the methods comprise administering a Cbl inhibitor to a donor prior to harvesting, conducting no second, rapid expansion, and administering expanded immune cells to a patient in need thereof in combination with a Cbl inhibitor. In certain embodiments, the methods comprise conducting a first expansion in the presence of a Cbl inhibitor, conducting no second, rapid expansion, and administering expanded immune cells to a patient in need thereof in combination with a Cbl inhibitor.

In one aspect, provided herein are expansion methods, compositions, and cell therapy methods for treating a condition in a patient in need thereof. In certain embodiments, the methods comprise administering a Cbl inhibitor to a donor under conditions suitable to promote activation or expansion of immune cells in the donor. In certain embodiments, the methods further comprise harvesting circulating immune cells from the donor. In certain embodiments, the methods further comprise optionally genetically modifying the harvested immune cells. In certain embodiments, the methods further comprise expanding immune cells from the donor ex vivo. In certain embodiments, the methods further comprise administering the immune cells to a patient in need thereof.

In another aspect, provided herein are expansion methods, compositions, and cell therapy methods for treating a condition in a patient in need thereof. In certain embodiments, the methods comprise harvesting circulating immune cells from the donor. In certain embodiments, the methods further comprise optionally genetically modifying the harvested immune cells. In certain embodiments, the methods further comprise expanding immune cells ex vivo. In certain embodiments, the expansion step is in the presence of a Cbl inhibitor. In certain embodiments, the methods further comprise administering the expanded immune cells to a patient in need thereof.

In another aspect, provided herein are expansion methods, compositions, and cell therapy methods for treating a condition in a patient in need thereof. In certain embodiments, the methods comprise harvesting circulating immune cells from a donor. In certain embodiments, the methods further comprise optionally genetically modifying the harvested immune cells. In certain embodiments, the methods further comprise expanding immune cells ex vivo. In certain embodiments, the methods further comprise administering the immune cells to a patient in need thereof in combination with administering a sufficient amount of a Cbl inhibitor to enhance effectiveness of the immune cells. In certain embodiments, the Cbl inhibitor enhances durability of the immune cells. In certain embodiments, the Cbl inhibitor enhances engraftment of the immune cells.

In certain aspects, any of the above methods are combined. In certain embodiments, the methods comprise administering a Cbl inhibitor to a donor prior to harvesting circulating immune cells, optionally genetically modifying the harvested immune cells, conducting expansion in the presence of a Cbl inhibitor, and/or administering expanded immune cells to a patient in need thereof in combination with a Cbl inhibitor.

The immune cells can be any immune cells deemed useful to the person of skill. The immune cells can be isolated from tumors or from circulating cells in the blood or plasma. In certain embodiments, the immune cells are selected from tumor infiltrating lymphocytes, T cells, CAR-T cells, TCR T cells, natural killer cells, and NK-CAR cells. In certain embodiments, the immune cells are a patient's T cells that have been selected for the presence of a specific tumor antigen. In certain embodiments, the immune cells are engineered and selected for the presence of, for instance, a T cell receptor or chimeric antigen receptor. The methods can be used for any purpose deemed suitable by the practitioner of skill. In certain embodiments, the methods are useful for enhancing cell engraftment in a patient in need thereof. In certain embodiments, the methods are useful for treating immune cell dysfunction in a patient in need thereof. In certain embodiments, the methods are useful for treating T cell dysfunction in a patient in need thereof. In certain embodiments, the methods are useful for treating cancer in a patient in need thereof. In certain embodiments, cells made by the methods described herein can be used in the treatment of solid tumors. In certain embodiments, cells made by the methods described herein can be used in the treatment of a relapsing or refractory cancer. In certain embodiments, cells made by the methods described herein can be used in combination with chemotherapy for the treatment of cancer or T cell dysfunction.

In another aspect, provided herein are methods of expanding immune cells in vitro. In certain embodiments, the methods comprise expanding immune cells in vitro in the presence of a Cbl inhibitor under conditions wherein more memory immune cells are produced than in the absence of the Cbl inhibitor, and optionally subjecting the expanded cells to a second round of expansion, optionally in the presence of a Cbl inhibitor. In some embodiments, the immune cells are T cells and more $T_{SCM}$ and/or $T_{CM}$ are produced than in the absence of the Cbl inhibitor. In some embodiments, more $T_{CM}$ are produced than in the absence of the Cbl inhibitor. In certain embodiments, the expanded immune cells are not subjected to a second round of expansion. In certain other embodiments, the expanded immune cells are subject to a second round of expansion optionally in the presence of a Cbl inhibitor.

In another aspect, provided herein are compositions comprising cells made by any of the methods described herein. The compositions of the methods described herein can be used, for example, for the treatment of cancer and/or immune cell dysfunction. In certain embodiments, cells made by the methods described herein can be used in the treatment of solid tumors. In certain embodiments, cells made by the methods described herein can be used in the treatment of a relapsing or refractory cancer. In certain embodiments, cells made by the methods described herein can be used in combination with chemotherapy for the treatment of cancer or immune cell dysfunction.

BRIEF DESCRIPTION OF THE FIGURES

FIG. 1A shows the number of cells/well after culture in the presence of 10 μM, 1 μM, and 0.1 μM Cbl inhibitor alone for 28 days. FIG. 1B shows the numbers of cells from the same source materials after culture in the presence of 10 μM, 1 μM, and 0.1 μM Cbl inhibitor and 6000 IU IL-2 after 28 days incubation.

FIGS. 4A, 4B, and 4D are TIL cells derived from ovarian tumors from 3 separate patients. FIG. 4C shows the results for TIL cells derived from colon tumor tissue.

FIG. 14A provides results showing that OT-1 cells expanded with Cbl inhibitor demonstrate higher frequency in total CD45+ cells in the tumors. FIGS. 14B and 14C provide results showing that OT-1 cells expanded with Cbl inhibitor decrease the expression of exhaustion markers PD1 and TIM3 (FIG. 14B) and PD1, TIM3, and LAG3 (FIG. 14C) in the tumor.

FIGS. 16A and 16B provides multifunctionality (IFN-gamma and TNF-alpha double positive cells) of peptide-restimulated OT-1 cells expanded with and without Cbl inhibitor. FIG. 16C provides exhaustion markers (PD1 and TIM3) frequency in multifunctional (IFN-gamma and TNF-alpha double positive) OT-1 cells expanded with and without Cbl inhibitor.

FIG. 17A provides IFN-gamma production upon restimulation. FIG. 17B provides IFN-gamma and IL-2 production upon restimulation.

FIG. 23A provides FACS data showing percentages of memory phenotype CD4+ T cells (CD3+CD8−). FIG. 23B provides CD8+ T cells (CD3+CD8+) among CD45RO+. FACS results were expressed as the mean ±SEM. Statistical significance was calculated using two-tailed Wilcoxon signed-rank test (*, $p<0.05$).

FIG. 25A provides FACS data showing percentages of memory phenotype CD8+ T cells (CD3+CD8+) among CD45RO+. FIG. 25B provides total number of CD8 + TIL obtained after 14 days' ex vivo culture from cancer tissues of patients. FACS results expressed as the mean ±SEM. Statistical significance was calculated using two-tailed Wilcoxon signed-rank text (*, $p<0.05$).

DETAILED DESCRIPTION

Definitions

Figure 1A:
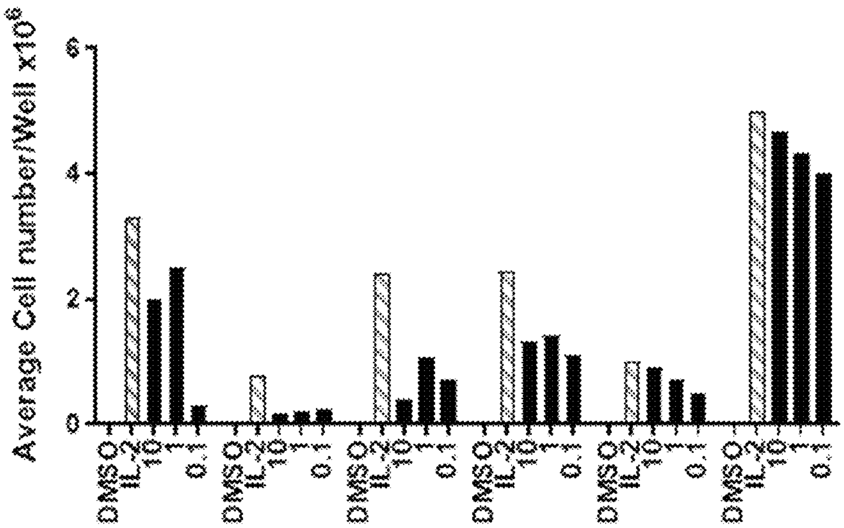
FIGS. 1A and 1B provide results of TIL studies using cells derived from human ovary and colon tumor fragments to show the effects of a Cbl inhibitor in the absence and presence of IL-2 on cell growth in vitro.

When referring to the compounds and methods provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise. The techniques and procedures described or referenced herein are generally well understood and commonly employed using conventional methodologies by those skilled in the art, such as, for example, the widely utilized molecular cloning methodologies described in Green & Sambrook, *Molecular Cloning: A Laboratory Manual* 4$^{th}$ ed. (2012), Cold Spring Harbor Laboratory Press, Cold Spring Harbor, N.Y.; Ausubel et al., *Current Protocols in Molecular Biology*, John Wiley & Sons; and Rosenberg et al., *J. Natl. Cancer Inst.,* 86(15):1159-1166 (1994). As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise.

The term "about" indicates and encompasses an indicated value and a range above and below that value. In certain embodiments, the term "about" indicates the designated value ±10%, ±5%, or ±1%. In certain embodiments, the term "about" indicates the designated value±one standard deviation of that value. For logarithmic scale, "about" indicates a designated value ±0.1 or ±0.2 log units.

The term "abnormal cell proliferation" as used herein includes hyperplasia or cancer cell proliferation. The cancer cell can be derived from a hematologic cancer or a non-hematologic cancer such as those described herein.

"Activation" in vivo, as used herein, refers to providing a suitable set of conditions in vivo, particularly in an individual undergoing cell-based immunotherapy, for the contacting the immune cell with an effective amount of a Cbl inhibitor to modulate activity of the immune cell population of said individual prior to harvest. In some embodiments, the immune cell is a T-cell, a B cell, or a natural killer (NK) cell. The immune cell can be a circulating T cell. The immune cell can be a tumor infiltrating lymphocyte. In some of any such embodiments, the immune cell is a T-cell, and modulating activity of the T-cell comprises one or more of increased T-cell activation, increased T-cell proliferation, decreased T-cell exhaustion, and decreased T-cell tolerance. In a further embodiment, increased T-cell activation comprises increased production of a cytokine such as one or more selected from the group consisting of: IL-2, IFN-γ, and TNFα. In yet another further embodiment, increased T-cell activation comprises increased cell surface expression of one or more T-cell activation markers such as one or more of CD25, CD69, and CD45RO. In some of any such embodiments, the T-cell has been or is in contact with an anti-CD3 antibody alone or in combination with an anti-CD28 antibody. In some of any such embodiments, the immune cell is a NK cell, and modulating activity of an NK cell comprises increased NK cell activation. In a further embodiment, increased NK cell activation comprises increased production of a cytokine such as IFN-γ. In some of any such embodiments, the immune cell is a B cell, and modulating activity of a B cell comprises increased B cell activation (e.g., increase in CD69 and the like). In some any of such embodiments, the immune cell is a human immune cell.

"Administration" and variants thereof (in some embodiments, "administering" a compound or a population of cells) in reference to a compound, e.g., a Cbl inhibitor, or population of cells of the disclosure means introducing the compound or a prodrug of the compound, or a population of cells treated with said compound, e.g., a Cbl inhibitor, into the system of the animal for activation of cells or for treatment. When a compound of the disclosure or prodrug thereof is provided in combination with one or more other active agents (in some embodiments, e.g., infusion of a population of cells, surgery, radiation, and chemotherapy, etc.), "administration" and its variants are each understood to include concurrent and sequential introduction of the compound and other agents or elements.

The term "Cbl" as used herein refers to a Cbl protein selected from a group comprising cCbl, Cbl-b, and Cbl-c. The term also includes naturally occurring variants of these proteins, including splice variants or allelic variants. The term also includes non-naturally occurring variants of these proteins, such as a recombinant Cbl protein or truncated variants thereof, which generally preserve the binding ability of naturally occurring Cbl or naturally occurring variants of Cbl (e.g., the ability to bind to an E2 enzyme).

The term "Cbl inhibitor" as used herein refers to a compound that binds to Cbl and inhibits activity or function of a Cbl protein. In some embodiments, the Cbl inhibitor is a compound that inhibits the activity of Cbl-b. In other embodiments, the Cbl inhibitor is a compound that is capable of activating T cells in the absence of co-stimulation.

"Contacting" cells in vivo, ex vivo, or in vitro, refers to exposing a cell or cells in a population to a specific compound, molecule, or reagent. Compounds that may be contacted with cells include cytokines, antibodies, mitogens, recombinant ligands, and lectins.

As used herein, a "donor" is a mammal. A "mammal" for purposes of a source for immune cells to be used in the methods of the disclosure includes humans; non-human primates; domestic and farm animals; and zoo, sports, or pet animals, such as dogs, horses, rabbits, cattle, pigs, hamsters, gerbils, mice, ferrets, rats, cats, etc. In some embodiments, the donor is human. A "related donor" is a close blood relative of the individual undergoing treatment. A "living nonrelated donor" is an individual who is not a close blood relative of the individual undergoing treatment.

"Drug-enhanced adoptive cell therapy" refers to adoptive cell therapies comprising the use of one or more Cbl inhibitors to increase the quantities of cell to be harvested for use in adoptive cell therapies, shorten the length of time needed for selection and expansion of cells in vitro, increase the numbers and durability of cells to be produced in adoptive cell therapies for infusion into a patient in need thereof, and/or increase the efficacy of the adoptive cell therapy in a patient in need thereof.

"Drug-enhanced chimeric antigen receptor therapy" refers to chimeric antigen therapies comprising the use of one or more Cbl inhibitors to increase the quantities of cells to be harvested for use in adoptive cell therapies, shorten the length of time needed for selection and expansion of genetically modified cells in vitro, increase the numbers and durability of genetically modified cells for infusion into a patient in need thereof, and/or increase the efficacy of the chimeric antigen receptor therapy in a patient in need thereof.

"Drug-enhanced TIL therapy" refers to tumor infiltrating lymphocyte therapies comprising the use of one or more Cbl inhibitors to increase the quantities of cells to be harvested from tumor fragments, shorten the length of time needed for selection and expansion of TIL in vitro, increase the numbers and durability of TIL to be produced for infusion into a patient in need thereof, and/or increase the efficacy of the TIL therapy in a patient in need thereof.

An "effective amount" of an agent disclosed herein is an amount sufficient to carry out a specifically stated purpose. An "effective amount" may be determined empirically and in a routine manner, in relation to the stated purpose. An "effective amount" or an "amount sufficient" of an agent is that amount adequate to produce a desired biological effect, such as a beneficial result, including a beneficial clinical result. In some embodiments, the term "effective amount" refers to an amount of an agent effective to "treat" a disease or disorder in an individual (e.g., a mammal such as a human).

An "enriched" cell population refers to a group of cells that have been purified, sorted, or exposed to conditions (e.g., culture in vitro in the presence of specific compounds or molecules) for a period of time that promotes survival or proliferation of a cells of a particular phenotype or functional activity. In some embodiments, an enriched cell population will have a higher concentration or proportion of a particular cell type than found in normal tissue environments.

As used herein, the term "hematopoietic cells" includes hematopoietic stem cells and hematopoietic progenitor cells.

"Immune cells" refer to hematopoietic cells, multipotent stem cells, myeloid progenitor cells, lymphoid progenitor cells, tumor infiltrating lymphocytes, T cells, B cells, and/or NK cells.

As used herein, the term "inhibits growth" (e.g. referring to cells, such as tumor cells) is intended to include any measurable decrease in cell growth (e.g., tumor cell growth) when contacted with cells that have been treated with Cbl inhibitors. In certain embodiments, cell growth is compared to the growth of the same cells not in contact with cells or cells that have been treated with Cbl inhibitors. In some embodiments, growth may be inhibited by at least about 10%, 20%, 30%, 40%, 50%, 60%, 70%, 80%, 90%, 95%, 99%, or 100%. The decrease in cell growth can occur by a variety of mechanisms, including but not limited to protein internalization, apoptosis, necrosis, and/or effector function-mediated activity.

As used herein, the terms "prophylactic agent" and "prophylactic agents" refer to any agent(s) which can be used in the prevention of a condition, disease, or disorder or one or more symptoms thereof. In certain embodiments, the term "prophylactic agent" includes a compound provided herein. In certain other embodiments, the term "prophylactic agent" does not refer to a compound provided herein. In certain embodiments, a prophylactic agent can be an agent which is known to be useful for, or has been or is currently being used to prevent or impede the onset, development, progression and/or severity of a condition, disease, or disorder associated with cancer or an immune-mediated disorder, or which is known to be useful for, or has been or is currently being used to prevent or impede the onset of side effects or reduce the severity of side effects (e.g., nausea, vomiting).

As used herein, the phrase "prophylactically effective amount" refers to the amount of a therapy (e.g., prophylactic agent) which is sufficient to result in the prevention or reduction of the development, recurrence or onset of one or more symptoms associated with a condition, disease, or disorder, or reduce or prevent side effects, or to enhance or improve the prophylactic effect(s) of another therapy (e.g., another prophylactic agent).

"Selection," "selective enrichment," or "selective expansion" refers to the ex vivo culture of immune cells harvested from an individual, or the in vitro culture of immune cells or stem cells from a donor, or cell line, under conditions to promote the proliferation of said immune cells, with enrichment of immune cells of a particular type, e.g., CD8+ T cells, or T cells of a particular phenotype, such as ($CD45RO^+/CD95^+$) memory T cells.

As used herein, the terms "subject", "individual" and "patient" are used interchangeably. The term "subject" refers to an animal, such as a mammal including anon-primate (e.g., a cow, pig, horse, cat, dog, rat, and mouse) and a primate (e.g., a monkey such as a cynomolgous monkey, a chimpanzee and a human), and in certain embodiments, a human. In certain embodiments, the subject is a farm animal (e.g., a horse, a cow, a pig, etc.) or a pet (e.g., a dog or a cat). In certain embodiments, the subject is a human.

As used herein, the term "T-cell dysfunction" refers to a state of reduced immune responsiveness to antigenic stimulation. The term "T-cell dysfunction" includes common elements of both T-cell exhaustion and/or T-cell anergy in which antigen recognition may occur, but the ensuing immune response is ineffective to control tumor growth. The term "T-cell dysfunction" also includes being refractory or unresponsive to antigen recognition, such as, impaired capacity to translate antigen recognition to downstream T-cell effector functions, such as proliferation, cytokine production and/or target cell killing.

The term "T-cell anergy" refers to the state of unresponsiveness to antigen stimulation resulting from incomplete or insufficient signals delivered through the T-cell receptor. "T-cell anergy" can also result upon stimulation with antigen in the absence of co-stimulation, resulting in the cell becoming refractory to subsequent activation by the antigen even in the context of co-stimulation.

The term "T-cell exhaustion" refers to a state of T-cell dysfunction that arises from sustained TCR signaling that can occur during cancer. It is distinguished from anergy in that it arises not through incomplete or deficient signaling, but from sustained signaling. It is defined by poor effector function, sustained expression of inhibitory receptors, and a transcriptional state distinct from that of functional effector or memory T cell.

The term "T-cell durability" refers to a transplanted or infused T cell's ability to persist as a reservoir and also continue proliferating post-infusion for a period of time, allowing for continued immune surveillance by said T cells to promote eradication of current and potentially future malignancies. Some of these T cells are in an activated state. Durability also refers to engrafted cells' ability to survive or persist upon infusion. Durability of the T cell response or cell engraftment can be associated with disease remission.

A "T-cell dysfunction disorder" is a disorder or condition characterized by decreased responsiveness of T cells to antigenic stimulation. Decreased responsiveness may result in ineffective control of a tumor. In some embodiments, the term "T-cell dysfunction disorder" encompasses cancer such as a hematologic cancer or a non-hematologic cancer. In some embodiments, a "T-cell dysfunction disorder" is one in which T cells are anergic or have decreased ability to secrete cytokines, to proliferate and/or to execute cytolytic activity.

"Enhancing T-cell function" means to induce, cause or stimulate a T cell to have a sustained or amplified biological function, or renew or reactivate exhausted or inactive T cells. Examples of enhanced T-cell function include increased T-cell activation (e.g., increased cytokine production, increased expression of T-cell activation markers, etc.), increased T-cell proliferation, decreased T-cell exhaustion, and/or decreased T-cell tolerance relative to the state of the T cells before treatment with a Cbl inhibitor. Methods of measuring enhancement of T-cell function are known in the art.

As used herein, the term "therapeutically effective amount" or "effective amount" refers to an amount of a protein or composition that when administered to a subject is effective to treat a disease or disorder. In some embodiments, a therapeutically effective amount or effective amount refers to an amount of a composition that when administered to a subject is effective to prevent or ameliorate a disease or the progression of the disease, or result in amelioration of symptoms. The term "therapeutic agent" can refer to a Cbl inhibitor, a modified immune cell population, or combinations, or compositions thereof.

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter)

or both. In yet another embodiment, "treating" or "treatment" includes delaying or preventing the onset of the disease or disorder.

In another embodiment, the terms "treating" or "treatment" of a disease refer to executing a protocol, which may include administering one or more therapeutic agents to an individual (human or otherwise), in an effort to obtain beneficial or desired results in the individual, including clinical results. Beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total). "Treatment" also can mean prolonging survival as compared to expected survival of an individual not receiving treatment. Further, "treating" and "treatment" may occur by administration of one dose of a therapeutic agent or therapeutic agents, or may occur upon administration of a series of doses of a therapeutic agent or therapeutic agents. "Treating" or "treatment" does not require complete alleviation of signs or symptoms, and does not require a cure. "Treatment" also can refer to clinical intervention, such as administering one or more therapeutic agents to an individual, designed to alter the natural course of the individual or cell being treated (i.e., to alter the course of the individual or cell that would occur in the absence of the clinical intervention).

"Alkyl" as used herein refers to a saturated linear (i.e., unbranched) or branched univalent hydrocarbon chain or combination thereof. Particular alkyl groups are those having a designated number of carbon atoms, for example, an alkyl group having 1 to 20 carbon atoms (a "$C_1$-$C_{20}$ alkyl"), having 1 to 10 carbon atoms (a "$C_1$-$C_{10}$" alkyl), having 1 to 8 carbon atoms (a "$C_1$-$C_8$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Amino" refers to the group $—NH_2$.

"Aryl" as used herein refers to an aromatic carbocyclic group having a single ring (e.g., phenyl), or multiple condensed rings (e.g., naphthyl or anthryl) where one or more of the condensed rings may not be aromatic. Particular aryl groups are those having from 6 to 14 annular (i.e., ring) carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position. Examples of aryls include, but are not limited to, groups such as phenyl, naphthyl, 1-naphthyl, 2-naphthyl, 1,2,3,4-tetrahydronaphthalen-6-yl, and the like.

"Arylene" as used herein refers to the same residues as aryl, but having bivalency. Particular arylene groups are those having from 6 to 14 annular carbon atoms (a "$C_6$-$C_{14}$ arylene"). Examples of arylene include, but are not limited to, groups such as phenylene, o-phenylene (i.e., 1,2-phenylene), m-phenylene (i.e., 1,3-phenylene), p-phenylene (i.e., 1,4-phenylene), naphthylene, 1,2-naphthylene, 1,3-naphthylene, 1,4-naphthylene, 2,7-naphthylene, 2,6-naphthylene, and the like.

"Carbocyclyl" or "carbocyclic" refers to a univalent cyclic group in which all of the ring members are carbon atoms, such as cyclohexyl, phenyl, 1,2-dihydronaphthyl, etc.

"Cycloalkyl" as used herein refers to non-aromatic, saturated or unsaturated, cyclic univalent hydrocarbon structures. Particular cycloalkyl groups are those having a designated number of annular (i.e., ring) carbon atoms, for example, a cycloalkyl group having from 3 to 12 annular carbon atoms (a "$C_3$-$C_{12}$ cycloalkyl"). A particular cycloalkyl is a cyclic hydrocarbon having from 3 to 8 annular carbon atoms (a "$C_3$-$C_8$ cycloalkyl"), or having 3 to 6 annular carbon atoms (a "$C_3$-$C_6$ cycloalkyl"). Cycloalkyl can consist of one ring, such as cyclohexyl, or multiple rings, such as adamantyl, but excludes aryl groups. A cycloalkyl comprising more than one ring may be fused, spiro, or bridged, or combinations thereof. Examples of cycloalkyl groups include, but are not limited to, cyclopropyl, cyclobutyl, cyclopentyl, cyclohexyl, 1-cyclohexenyl, 3-cyclohexenyl, cycloheptyl, norbornyl, and the like.

"Cycloalkylene" as used herein refers to the same residues as cycloalkyl, but having bivalency. Particular cycloalkylene groups are those having 3 to 12 annular carbon atoms (a "$C_3$-$C_{12}$ cycloalkylene"), having from 3 to 8 annular carbon atoms (a "$C_3$-$C_8$ cycloalkylene"), or having 3 to 6 annular carbon atoms (a "$C_3$-$C_6$ cycloalkylene"). Examples of cycloalkylene groups include, but are not limited to, cyclopropylene, cyclobutylene, cyclopentylene, cyclohexylene, 1,2-cyclohexenylene, 1,3-cyclohexenylene, 1,4-cyclohexenylene, cycloheptylene, norbornylene, and the like.

"Halo" or "halogen" refers to elements of the Group 17 series having atomic number 9 to 85. Halo groups include fluoro, chloro, bromo, and iodo.

"Haloalkyl," "haloalkylene," "haloaryl," "haloarylene," "haloheteroaryl," and similar terms refer to a moiety substituted with at least one halo group. Where a haloalkyl moiety or other halo-substituted moiety is substituted with more than one halogen, it may be referred to by using a prefix corresponding to the number of halogen moieties attached. For example, dihaloaryl, dihaloalkyl, trihaloaryl, trihaloalkyl, etc., refer to aryl and alkyl substituted with two ("di") or three ("tri") halo groups, which may be, but are not necessarily, the same halo; thus, for example, the haloaryl group 4-chloro-3-fluorophenyl is within the scope of dihaloaryl. The subset of haloalkyl groups in which each hydrogen of an alkyl group is replaced with a halo group is referred to as a "perhaloalkyl." A particular perhaloalkyl group is trifluoroalkyl ($—CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy ($—OCF_3$). "Haloalkyl" includes monohaloalkyl, dihaloalkyl, trihaloalkyl, perhaloalkyl, and any other number of halo substituents possible on an alkyl group; and similarly for other groups such as haloalkylene, haloaryl, haloarylene, haloheteroaryl, etc.

"Heteroaryl" as used herein refers to an unsaturated aromatic cyclic group having from 1 to 14 annular carbon atoms and at least one annular heteroatom, including, but not limited to, heteroatoms such as nitrogen, oxygen, and sulfur. A heteroaryl group may have a single ring (e.g., pyridyl or imidazolyl) or multiple condensed rings (e.g., indolizinyl, indolyl, or quinolinyl) where at least one of the condensed rings is aromatic. Particular heteroaryl groups are 5- to 14-membered rings having 1 to 12 annular carbon atoms and 1 to 6 annular heteroatoms independently selected from the group consisting of nitrogen, oxygen, and sulfur (a "5- to 14-membered heteroaryl"); 5- to 10-membered rings having 1 to 8 annular carbon atoms and 1 to 4 annular heteroatoms independently selected from the group consisting of nitrogen, oxygen, and sulfur (a "5- to 10-membered heteroaryl"); or 5-, 6-, or 7-membered rings having 1 to 5 annular carbon atoms and 1 to 4 annular heteroatoms independently selected from the group consisting of nitrogen, oxygen, and sulfur (a "5- to 7-membered heteroaryl"). In one variation, heteroaryl includes monocyclic aromatic 5-, 6-, or 7-membered rings having from 1 to 6 annular carbon atoms and 1 to 4 annular heteroatoms independently selected from the group consisting of nitrogen, oxygen, and sulfur. In another variation, heteroaryl includes polycyclic aromatic rings having from 1 to 12 annular carbon atoms and 1 to 6 annular heteroatoms independently selected from the group consisting of nitrogen, oxygen, and sulfur. A heteroaryl group having more than one ring where at least one ring is non-aromatic may be connected to the parent structure at either an aromatic ring position or at a non-aromatic ring position. Examples of heteroaryl include, but are not limited to, groups such as pyridyl, benzimidazolyl, benzotriazolyl, benzo[b]thienyl, quinolinyl, indolyl, benzothiazolyl, and the like. "Heteroaryl" also includes moieties such as

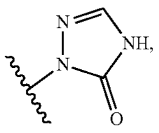 [SMILES: *n1nc[nH]c1=O]

2,4-dihydro-3H-1,2,4-triazol-3-one-2-yl, which has the tautomeric structure

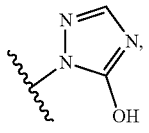

1H-1,2,4-triazol-5-ol-1-yl.

"Heteroarylene" as used herein refers to the same residues as heteroaryl, but having bivalency. Particular heteroarylene groups are 5- to 14-membered rings having 1 to 12 annular carbon atoms and 1 to 6 annular heteroatoms independently selected from the group consisting of nitrogen, oxygen, and sulfur (a "5- to 14-membered heteroarylene"); 5- to 10-membered rings having 1 to 8 annular carbon atoms and 1 to 4 annular heteroatoms independently selected from the group consisting of nitrogen, oxygen, and sulfur (a "5- to 10-membered heteroarylene"); or 5-, 6-, or 7-membered rings having 1 to 5 annular carbon atoms and 1 to 4 annular heteroatoms independently selected from the group consisting of nitrogen, oxygen, and sulfur (a "5- to 7-membered heteroarylene"). Examples of heteroarylene include, but are not limited to, groups such as pyridylene, benzimidazolylene, benzotriazolylene, benzo[b]thienylene, quinolinylene, indolylene, benzothiazolylene, and the like.

"Heterocyclyl" and "heterocyclic groups" as used herein refer to non-aromatic saturated or partially unsaturated cyclic groups having the number of atoms and heteroatoms as specified, or if no number of atoms or heteroatoms is specified, having at least three annular atoms, from 1 to 14 annular carbon atoms, and at least one annular heteroatom, including, but not limited to, heteroatoms such as nitrogen, oxygen, and sulfur. A heterocyclic group may have a single ring (e.g., tetrahydrothiophenyl, oxazolidinyl) or multiple condensed rings (e.g., decahydroquinolinyl, octahydrobenzo[d]oxazolyl). Multiple condensed rings include, but are not limited to, bicyclic, tricyclic, and quadracylic rings, as well as bridged or spirocyclic ring systems. Examples of heterocyclic groups include, but are not limited to, aziridinyl, azetidinyl, pyrrolidinyl, piperidinyl, oxiranyl, oxetanyl, tetrahydrofuranyl, tetrahydropyranyl, oxazolidinyl, piperazinyl, morpholinyl, dioxanyl, 3,6-dihydro-2H-pyranyl, 2,3-dihydro-1H-imidazolyl, and the like.

"Oxo" refers to the group =O, that is, an oxygen atom doubly bonded to carbon or another element.

"Optionally substituted," unless otherwise specified, means that a group is unsubstituted or substituted by one or more (e.g., 1, 2, 3, 4, or 5) of the substituents listed for that group, in which the substituents may be the same or different. In one embodiment, an optionally substituted group is unsubstituted. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, or 1 to 5 substituents. When multiple substituents are present, each substituent is independently chosen unless indicated otherwise. For example, each ($C_1$-$C_4$ alkyl) substituent on the group —N($C_1$-$C_4$ alkyl)($C_1$-$C_4$ alkyl) can be selected independently from the other, so as to generate groups such as —N($CH_3$)($CH_2CH_3$), etc.

A "small molecule" as used herein refers to a compound of 2,000 daltons or less in molecular weight.

In addition to the disclosure herein, the term "substituted," when used to modify a specified group or radical, can also mean that one or more hydrogen atoms of the specified group or radical are each, independently of one another, replaced with the same or different substituent groups as defined herein. In some embodiments, a group that is substituted has 1, 2, 3, or 4 substituents, 1, 2, or 3 substituents, 1 or 2 substituents, or 1 substituent.

Substituents can be attached to any chemically possible location on the specified group or radical, unless indicated otherwise. Thus, —$C_1$-$C_8$ alkyl-OH includes, for example, —$CH_2CH_2OH$ and —CH(OH)—$CH_3$, and —$CH_2C(OH)(CH_3)_2$.

Unless a specific isotope of an element is indicated in a formula, the disclosure includes all isotopologues of the compounds disclosed herein, such as, for example, deuterated derivatives of the compounds (where H can be $^2H$, i.e., D). Deuterated compounds may provide favorable changes in pharmacokinetic (ADME) properties. Isotopologues can have isotopic replacements at any or at all locations in a structure, or can have atoms present in natural abundance at any or all locations in a structure.

"Excipients" as used herein include pharmaceutically acceptable excipients, carriers, vehicles or stabilizers that are nontoxic to the cell or mammal being exposed thereto at the dosages and concentrations employed. Often the physiologically acceptable excipient is an aqueous pH buffered solution.

The terms "pharmaceutical formulation" and "pharmaceutical composition" refer to preparations that are in such form as to permit the biological activity of the active ingredient to be effective, and that contain no additional components that are unacceptably toxic to an individual to which the formulation or composition would be administered. Such formulations or compositions may be sterile.

Reference to a compound as described in a pharmaceutical composition, or to a compound as described in a claim to a pharmaceutical composition, refers to the compound described by the formula recited in the pharmaceutical composition, without the other elements of the pharmaceutical composition, that is, without carriers, excipients, etc.

The disclosure is intended to embrace all salts of the compounds described herein, as well as methods of using such salts of the compounds. In one embodiment, the salts of the compounds comprise pharmaceutically acceptable salts. Pharmaceutically acceptable salts are those salts that can be administered as drugs or pharmaceuticals to humans and/or animals and that, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, also can be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N'-dibenzylethylenediamine, and triethylamine salts. Salts of acidic compounds with amino acids, such as lysine salts, also can be prepared. For lists of pharmaceutically acceptable salts, See, for example, P. H. Stahl and C. G. Wermuth (eds.) "Handbook of Pharmaceutical Salts, Properties, Selection and Use" Wiley-VCH, 2011 (ISBN: 978-3-90639-051-2). Several pharmaceutically acceptable salts are disclosed in Berge, *J. Pharm. Sci.* 66:1 (1977).

Overview

Provided herein are methods and compositions using Cbl inhibitors for cell therapy. The cells can be any immune cells deemed useful by the practitioner of skill. In certain embodiments, the cells are tumor infiltrating lymphocytes, T cells, NK cells, CAR-T cells, TCR-T cells or NK-CAR cells. In some embodiments, a Cbl inhibitor is used to activate T cells to enable a desired result as described herein. In some embodiments, a Cbl inhibitor is used to activate T cells in the absence of co-stimulation to enable a desired result as described herein.

Methods for cell therapy are well known, and the steps provided herein can utilize standard techniques known to the practitioner of skill, unless specified otherwise. Generally, the methods comprise any or all of the following steps. One or more Cbl inhibitors can enhance one or more of the steps, as described in detail below.

In a first step, cells are harvested from a donor. Harvesting can proceed by standard techniques. In certain embodiments, circulating immune cells, for instance blood cells, are harvested from the donor. In certain embodiments, one or more tumors or tumor tissue is obtained from the donor and fragmented, and immune cells are then isolated and harvested from the tumor fragments. In a second step, the harvested immune cells are expanded in one or two steps. Generally, harvested circulatory immune cells typically are expanded in one step due to the relatively large number of cells that are obtained. In contrast, immune cells harvested from tumors typically require expansion in two steps due to fewer numbers of immune cells that are typically obtained from the tumor fragments as compared to from blood. In either case, the harvested immune cells optionally can be genetically modified prior to expansion. In either case, the first expansion can proceed from 3-28 days, preferably for 3-14 days. The first expansion should result in a several-fold increase in the number of immune cells.

Some methods comprise an optional second expansion. In the second expansion, the cell culture medium may be supplemented to enhance growth of the immune cells than could be obtained without such supplementation. The second expansion can proceed for 3-14 days, preferably for 7-14 days. Importantly, in certain advantageous embodiments, the second expansion is not needed for immune cells harvested from tumors because of the effects of the Cbl inhibitor in earlier steps. Thus, in certain embodiments, there is no second expansion step. Following expansion (whether in one or two steps), expanded immune cells are recovered. The immune cells can be stored. In a further step, the recovered immune cells are administered to a patient by standard techniques, for instance infusion. As described in detail below, one or more Cbl inhibitors can enhance growth, expansion, and development of immune cells in the host prior to harvesting, can enhance either of the expansion steps, can enhance administration of the immune cells for therapy, and/or can enhance the immune cells post-administration to enhance their engraftment. Embodiments are described briefly in the following paragraphs and in more detail in the sections below.

The Cbl inhibitors are useful at one or more steps of the methods. In certain embodiments, a Cbl inhibitor is used in one step. In certain embodiments, Cbl inhibitors are used in more than one step. In certain embodiments, Cbl inhibitors are used in two steps. In certain embodiments, Cbl inhibitors are used in three steps. In certain embodiments, a Cbl inhibitor enhances expansion of immune cells in vivo in a donor. In certain embodiments, a Cbl inhibitor enhances a first expansion of immune cells ex vivo. In certain embodiments, a Cbl inhibitor enhances a second or rapid expansion of immune cells ex vivo. In certain embodiments, a Cbl inhibitor enhances the post-administration engraftment of the administered immune cells in the patient. In certain embodiments, a Cbl inhibitor administered to a patient enhances the benefits of the administered immune cells in the patient in need of such immune cells therapy.

In certain embodiments, the methods comprise administering a Cbl inhibitor to an individual. The individual can be a donor of immune cells. The donor can be an autologous donor and also a patient in need of therapy. The donor also can be an individual providing cells for allogeneic therapy. In certain embodiments, the Cbl inhibitor is administered to a donor prior to harvest of immune cells. In certain embodiments, the Cbl inhibitor increases the overall number of immune cells that can be harvested from the donor. In certain embodiments, the Cbl inhibitor increases levels of activated cells in the donor. In certain embodiments, the Cbl inhibitor increases cells with specific activity, e.g., is cytotoxic to or binds to a particular tumor or cancer type. In certain embodiments, the Cbl inhibitor increases levels of tumor infiltrating lymphocytes. In certain embodiments, the Cbl inhibitor increases levels of circulating T cells.

In certain embodiments, a Cbl inhibitor enhances expansion of immune cells. The immune cells can be harvested according to standard techniques. In certain embodiments, the cell sample is circulating blood cells or plasma comprising immune cells. In certain embodiments, the cell sample is tumor tissue comprising immune cells. In certain embodiments, the harvested immune cells are cultured ex vivo in the presence of one or more Cbl inhibitors. In some embodiments, culture in the presence of the Cbl inhibitors results in increased yields of immune cells that are harvested from tumor fragments. In certain embodiments, culture in the presence of Cbl inhibitors results in higher propagation rates. In certain embodiments, culture in the presence of Cbl inhibitors results in a higher percentage of propagated cells displaying phenotypes of activated immune cells. For example, a cell cultured from one of many different tumor sources, i.e., melanoma, breast cancer, ovarian or colon tumors, when cultured in the presence of Cbl inhibitors, in certain embodiments shows increased expression of a phenotype that is desirable for some types of cell-based immunotherapies. In certain embodiments, a culture of immune cells in the presence of Cbl inhibitors yields higher levels of cells with the memory phenotype (e.g., CD45RO+/CD95+), which promote a more durable immune response which is associated with higher remission rates. An immune cell selectively expanded in the presence of Cbl inhibitors can display a different phenotype than one cultured in the presence of IL-2, another cytokine, or a combination thereof (e.g., IL-2 in combination with IL-7 and IL-15), providing more effective engraftment of the immune cells upon infusion into a patient in need thereof. In certain embodiments, expansion in the presence of a Cbl inhibitor eliminates the need for a second, rapid expansion of the immune cells. In certain embodiments, a Cbl inhibitor enhances the second, rapid expansion step. In certain embodiments, the Cbl inhibitor in any of the expansion steps is compound 103.

In certain embodiments, a Cbl inhibitor enhances administration of immune cells to a recipient or patient in need thereof. In certain embodiments, a Cbl inhibitor is administered in combination with expanded immune cells to an individual in need thereof. In certain embodiments, the administration promotes engraftment and/or growth rates of the immune cells. In certain embodiments, administration of a Cbl inhibitor enhances the durability of the immune response. In certain embodiments, administration of a Cbl inhibitor results in markedly decreased rates of disease progression and/or higher rates of remission. In certain embodiments, provided here are methods of cellular immunotherapy in an individual in need thereof, comprising: administering a Cbl inhibitor to the individual in an amount effective to enhance the cellular immunotherapy; and administering an effective amount of expanded immune cells to the individual for cellular immunotherapy. The Cbl inhibitor can be administered any time deemed suitable by the practitioner of skill. In certain embodiments, the Cbl inhibitor is administered prior to harvest, after harvest, prior to infusion, after infusion, or any combination thereof. In particular embodiments, the Cbl inhibitor is administered on day 1 following infusion and continuing for a number of days deemed suitable by the practitioner of skill. In certain embodiments, the Cbl inhibitor is administered daily for 1, 2, 3, 4, 5, 6, 7, 8, 9, 10, or up to 15, 20, 25, 30, or 35 days following infusion. In certain embodiments, the Cbl inhibitor is administered to the individual orally, intravenously, subcutaneously, or intratumorally. In certain embodiments, the Cbl inhibitor administered to the patient is compound 116 delivered orally. In certain embodiments, these methods are combined with any of the immune cell expansion embodiments described herein. In certain embodiments, the expansion steps comprise the use of compound 103 as described herein, and the administration steps comprise the use of compound 116 orally as described herein.

Cbl Inhibitors

Cbl inhibitors include small molecules, peptides, nucleic acids, or antibodies that inhibit the Cbl enzymes. Cbl enzymes include cCbl, Cbl-b, and Cbl-c. Cbl inhibitors for use in methods of treatment and compositions of the disclosure, include, but are not limited to, compounds and pharmaceutical compositions for cell-based immunotherapy. The Cbl inhibitors can be used in in vivo treatment methods to modulate the immune system, such as increasing activation of T cells, NK cells, circulating T cells, tumor infiltrating lymphocytes and B cells, to increase engraftment of infused ex vivo expanded immune cells, or to increase the durability of response to the infused ex vivo expanded immune cells. In addition, the Cbl inhibitors can be used to help expand such immune cells in vitro or ex vivo to increase their growth and proliferation or to modulate the phenotype of the resulting expanded immune cells In certain embodiments, the Cbl inhibitor is a compound according to Formula (A):

Formula (A)

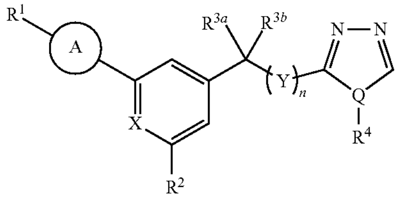

or a tautomer thereof, or a pharmaceutically acceptable salt of any of the foregoing, wherein:

$R^1$ is H, $C_1$-$C_6$ alkyl, $C_3$-$C_6$ cycloalkyl, 3- to 6-membered heterocyclyl, $C_1$-$C_6$ alkyl-($C_3$-$C_6$ cycloalkyl), $C_1$-$C_6$ alkyl-(3- to 6-membered heterocyclyl);

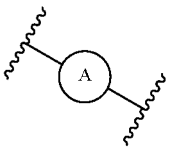 is 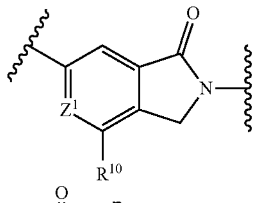 or

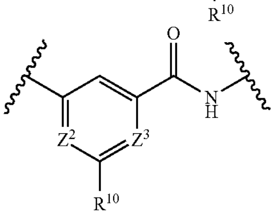 ;

$Z^1$ is CH or N;

$Z^2$ is CH or N;

$Z^3$ is CH or N;

X is CH or N;

$R^2$ is H, halo, $C_3$-$C_6$ cycloalkyl, —NH-(3- to 6-membered heterocyclyl), —NH—($C_1$-$C_6$ alkyl), —NH—($C_3$-$C_6$ cycloalkyl), —O-(3- to 6-membered heterocyclyl), —O—($C_1$-$C_6$ alkyl), or —O—($C_3$-$C_6$ cycloalkyl);

$R^{3a}$ is H, halo, or $C_1$-$C_6$ alkyl;

$R^{3b}$ is H, halo, $C_1$-$C_6$ alkyl, or $C_3$-$C_6$ cycloalkyl; or $R^{3a}$ and $R^{3b}$ are taken together with the carbon atom to which they are attached to form a 4- to 8-membered heterocyclyl or a $C_3$-$C_6$ cycloalkyl, wherein the heterocyclyl or cycloalkyl are optionally substituted by 1-3 $R^{12}$ groups;

or $R^{3b}$ and $R^{11a}$ are taken together with the carbon atoms to which they are attached to form a $C_3$-$C_6$ cycloalkyl optionally substituted by $C_1$-$C_6$ alkyl;

n is 0 or 1;

Y is $C(R^{11a})(R^{11b})$ or S, with the optional proviso that if either or both of $R^{3a}$ and $R^{3b}$ are halo, Y is $C(R^{11a})(R^{11b})$;

Q is CH or N;

$R^4$ is H, $C_1$-$C_6$ alkyl, $C_1$-$C_6$ haloalkyl, or $C_3$-$C_6$ cycloalkyl;

$R^{10}$ is H, $C_1$-$C_6$ alkyl, $C_1$-$C_6$ haloalkyl, or $C_3$-$C_6$ cycloalkyl;

$R^{11a}$ and $R^{11b}$ are independently H, halo, $C_1$-$C_6$ alkyl, or $C_1$-$C_6$ haloalkyl; or $R^{11a}$ and $R^{11b}$ are taken together with the carbon atom to which they are attached to form a $C_3$-$C_6$ cycloalkyl; or $R^{3b}$ and $R^{11a}$ are taken together with the carbon atoms to which they are attached to form a $C_3$-$C_6$ cycloalkyl optionally substituted by $C_1$-$C_6$ alkyl; and each $R^{12}$ is independently $C_1$-$C_6$ alkyl, halo, hydroxy, —O($C_1$-$C_6$ alkyl), —CN, $C_1$-$C_6$ alkyl-CN, $C_1$-$C_6$ alkyl-OH, or $C_1$-$C_6$ haloalkyl; wherein two geminal $R^{12}$ groups can be taken together with the carbon atom to which they are attached to form a spiro $C_3$-$C_4$ cycloalkyl.

In certain embodiments, $R^1$ is H, $C_1$-$C_6$ alkyl, $C_3$-$C_6$ cycloalkyl,

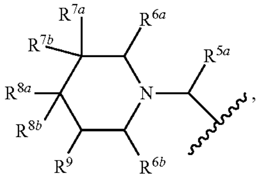,
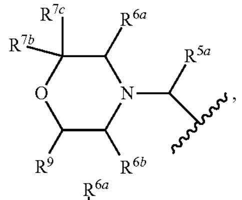,
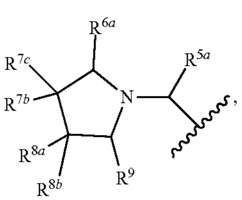, or
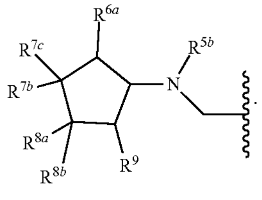.

In some embodiments, $R^1$ is

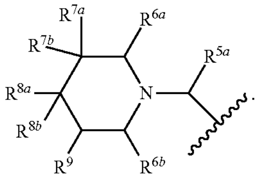.

In some embodiments, $R^1$ is

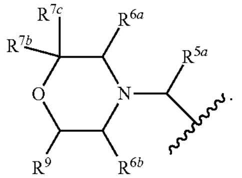.

In some embodiments, $R^1$ is

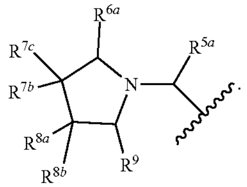.

In some embodiments $R^1$ is

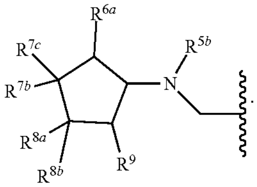.

In some embodiments of Formula (A), X is CH. In some embodiments, X is N.

In some embodiments of Formula (A), $R^2$ is H. In some embodiments, $R^2$ is —NH—($C_1$-$C_6$ alkyl).

In some embodiments, $R^2$ is —O—($C_1$-$C_6$ alkyl).

In some embodiments of Formula (A), $R^{3a}$ and $R^{3b}$ are taken together with the carbon atom to which they are attached to form

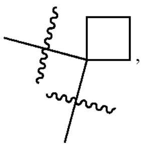,
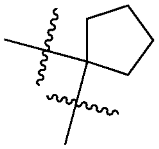,
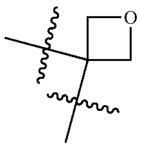,
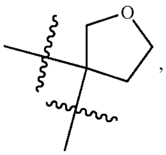,
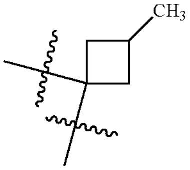,
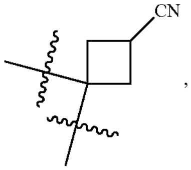,
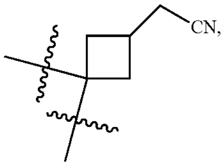,
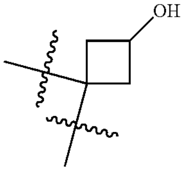, -continued

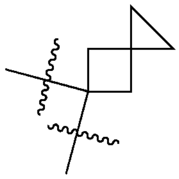
, or
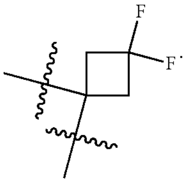

In some embodiments, $R^{3a}$ and $R^{3b}$ are taken together with the carbon atom to which they are attached to form

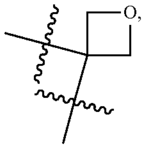
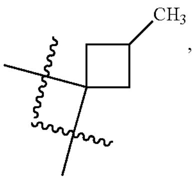
,
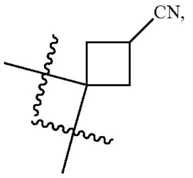
or
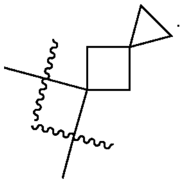

In some embodiments of Formula (A), $R^{3b}$ is $C_3$-$C_6$ cycloalkyl. In some embodiments, $R^{3b}$ is cyclobutyl. In some embodiments, $R^{3a}$ is H.

In some embodiments of Formula (A), $R^{3b}$ and $R^{11}$ are taken together with the carbon atoms to which they are attached to form a $C_3$-$C_6$ cycloalkyl optionally substituted by $C_1$-$C_6$ alkyl.

In some embodiments of Formula (A), n is 0. In some embodiments, n is 1.

In some embodiments of Formula (A), Y is C(Ria)(Rb). In some embodiments, $R^{11}$ and $R^{11b}$ are independently H, F, $CH_2F$, $CHF_2$, or $CF_3$. In some embodiments, Y is $CH_2$.

In some embodiments of Formula (A), Q is CH. In some embodiments, Q is N.

In some embodiments of Formula (A), $R^4$ is H. In some embodiments, $R^4$ is $CH_3$.

In some embodiments of Formula (A), $R^{5a}$ is H.

In some embodiments of Formula (A), $R^1$ is

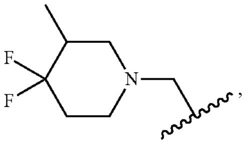
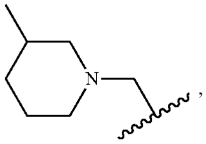
or
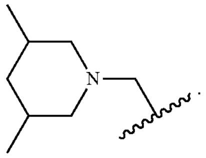

In some embodiments of Formula (A), $R^{5b}$ is H.

In some embodiments of Formula (A), $R^1$ is

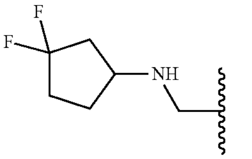
or
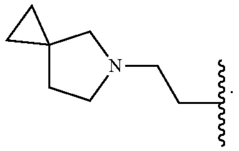

In some embodiments of Formula (A), $R^1$ is

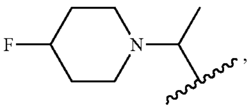
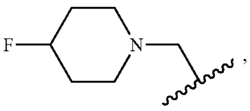
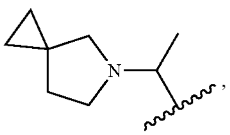
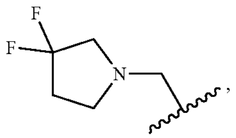
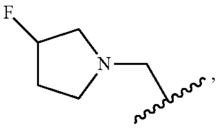
or
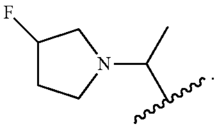

In some embodiments of Formula (A), $R^1$ is methyl. In some embodiments of Formula (A), $R^1$ is trifluoromethyl.

In some embodiments of Formula (A), $Z^1$ is CH. In some embodiments, $Z^1$ is N. In some embodiments, $Z^2$ is CH. In some embodiments, $Z^2$ is N. In some embodiments, $Z^3$ is CH. In some embodiments, $Z^3$ is N.

In some embodiments of Formula (A), $R^{10}$ is H. In some embodiments, $R^{10}$ is $CH_3$. In some embodiments, $R^{10}$ is $CF_3$. In some embodiments, $R^{10}$ is cyclopropyl. In some embodiments, $R^{10}$ is cyclopropyl and $R^1$ is methyl.

In some embodiments of Formula (A), $R^{3a}$ and $R^{3b}$ are taken together with the carbon atom to which they are attached to form a $C_3$-$C_6$ cycloalkyl optionally substituted by 1 $R^{12}$ group. In some embodiments, $R^{3a}$ and $R^{3b}$ are taken together with the carbon atom to which they are attached to form a $C_3$-$C_6$ cycloalkyl substituted by $C_1$-$C_6$ alkyl, —CN, or $C_1$-$C_6$ alkyl-CN.

In some embodiments, $R^{3a}$ and $R^{3b}$ are taken together with the carbon atom to which they are attached to form a $C_3$-$C_6$ cycloalkyl optionally substituted by CN or $CH_3$.

In certain embodiments, the Cbl inhibitor is a compound of Table 1. The compounds are prepared according to International application no. PCT/US2020/027492 or PCT/US2020/033274 or U.S. provisional application No. 62/888,845 or 62/888,870, each of which is incorporated herein by reference in its entirety.

TABLE 1
| Compound No. | Structure |
|---|---|
| 101 | 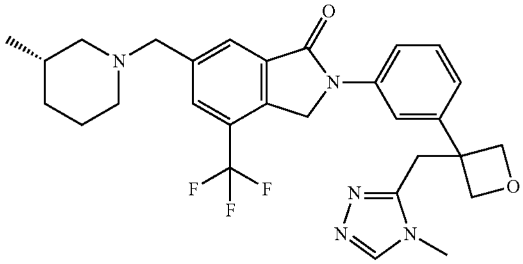 [SMILES: C[C@H]1CCCN(Cc2cc3c(c(C(F)(F)F)c2)CN(c2cccc(C4(Cc5nncn5C)COC4)c2)C3=O)C1] |
| 102 | 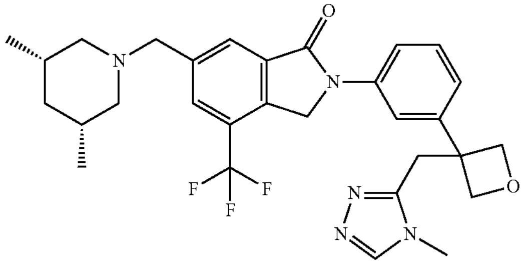 |
| 103 | 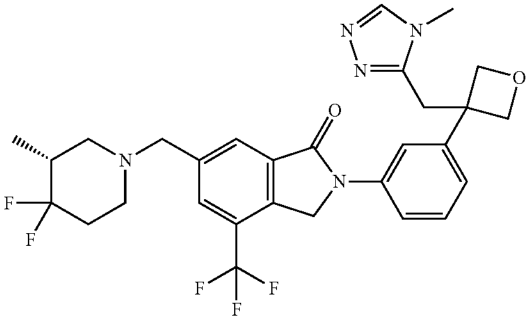 [SMILES: C[C@@H]1CN(Cc2cc3c(c(C(F)(F)F)c2)CN(c2cccc(C4(Cc5nncn5C)COC4)c2)C3=O)CCC1(F)F] |
| 104 | 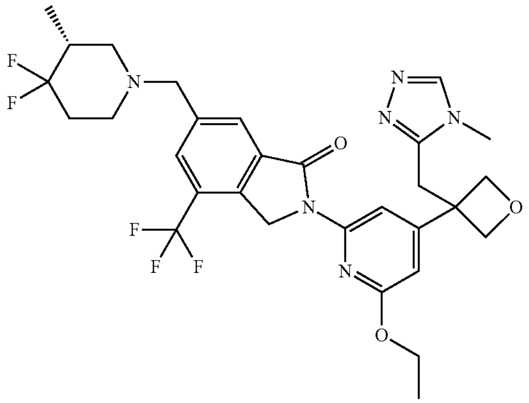 [SMILES: CCOc1cc(C2(Cc3nncn3C)COC2)cc(N2Cc3c(cc(CN4CCC(F)(F)[C@H](C)C4)cc3C(F)(F)F)C2=O)n1] |
| 105 | 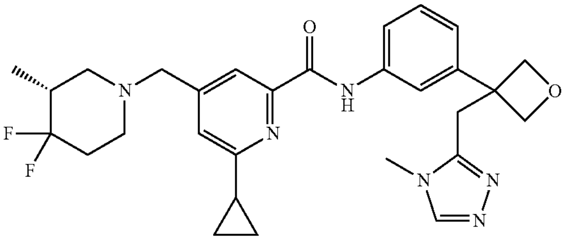 [SMILES: C[C@@H]1CN(Cc2cc(C(=O)Nc3cccc(C4(Cc5nncn5C)COC4)c3)nc(C3CC3)c2)CCC1(F)F] |

TABLE 1-continued
| Compound No. | Structure |
|---|---|
| 106 | 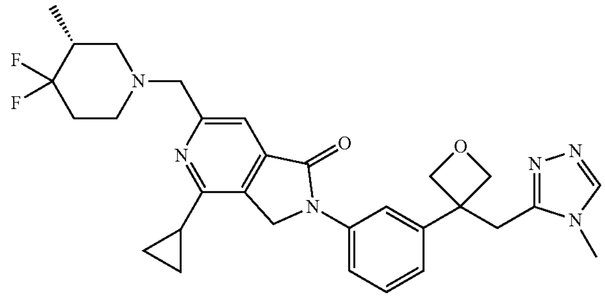 [SMILES: C[C@@H]1CN(Cc2cc3c(c(C4CC4)n2)CN(c2cccc(C4(Cc5nncn5C)COC4)c2)C3=O)CCC1(F)F] |
| 107 | 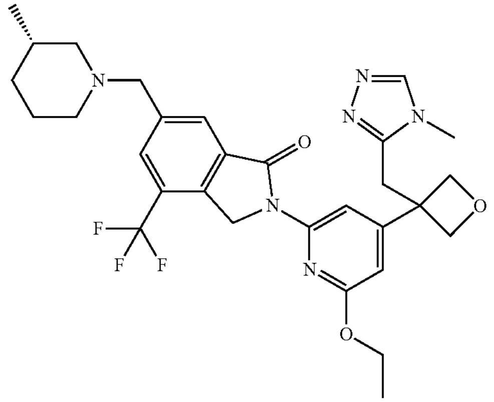 [SMILES: CCOc1cc(C2(Cc3nncn3C)COC2)cc(N2Cc3c(cc(CN4CCC[C@H](C)C4)cc3C(F)(F)F)C2=O)n1] |
| 108 | 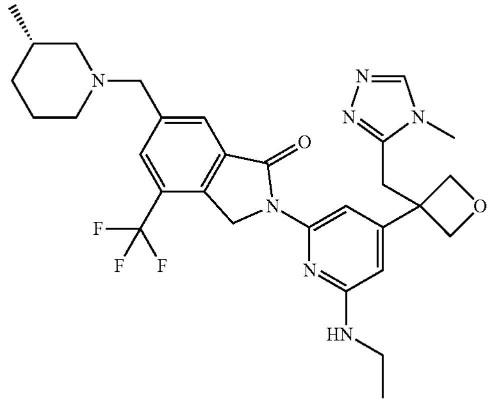 |
| 109 | 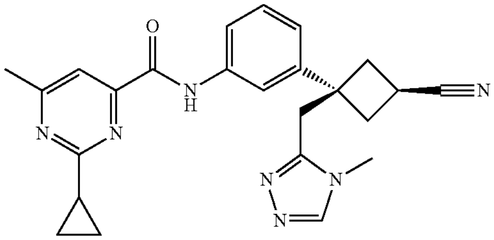 [SMILES: Cc1cc(C(=O)Nc2cccc([C@]3(Cc4nncn4C)C[C@@H](C#N)C3)c2)nc(C2CC2)n1] |

TABLE 1-continued
| Compound No. | Structure |
|---|---|
| 110 | 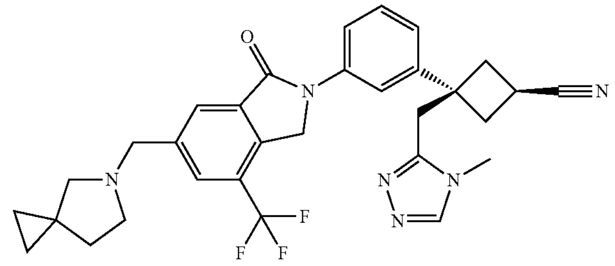 [SMILES: Cn1cnnc1C[C@]1(c2cccc(N3Cc4c(cc(CN5CCC6(CC6)C5)cc4C(F)(F)F)C3=O)c2)C[C@H](C#N)C1] |
| 111 | 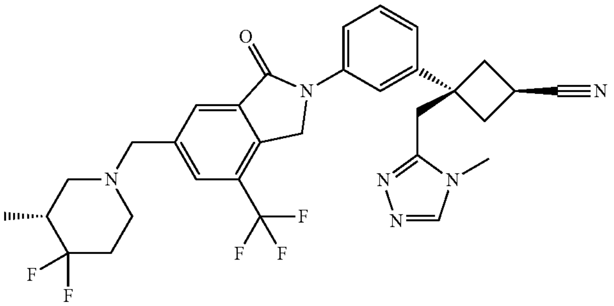 [SMILES: C[C@@H]1CN(Cc2cc3c(c(C(F)(F)F)c2)CN(c2cccc([C@]4(Cc5nncn5C)C[C@@H](C#N)C4)c2)C3=O)CCC1(F)F] |
| 112 | 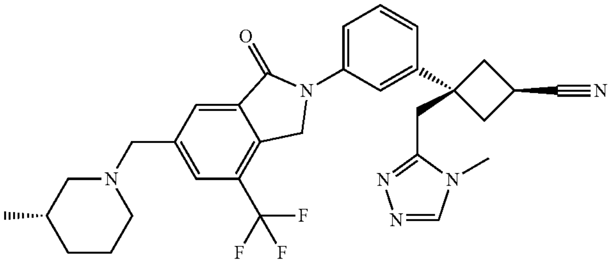 [SMILES: C[C@H]1CCCN(Cc2cc3c(c(C(F)(F)F)c2)CN(c2cccc([C@]4(Cc5nncn5C)C[C@@H](C#N)C4)c2)C3=O)C1] |
| 113 | 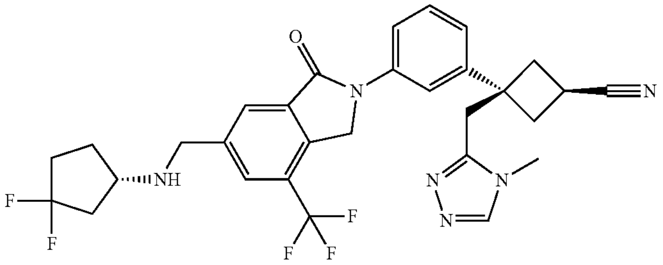 [SMILES: Cn1cnnc1C[C@]1(c2cccc(N3Cc4c(cc(CN[C@H]5CCC(F)(F)C5)cc4C(F)(F)F)C3=O)c2)C[C@H](C#N)C1] |
| 114 | 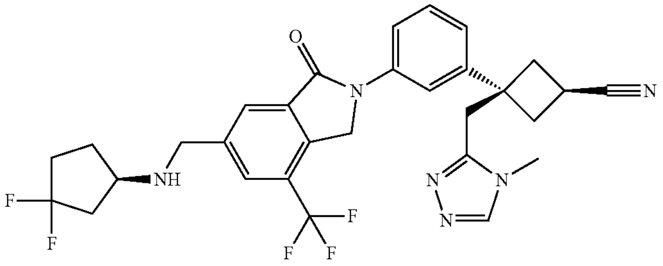 [SMILES: Cn1cnnc1C[C@]1(c2cccc(N3Cc4c(cc(CN[C@@H]5CCC(F)(F)C5)cc4C(F)(F)F)C3=O)c2)C[C@H](C#N)C1] |

TABLE 1-continued
| Compound No. | Structure |
| --- | --- |
| 115 | 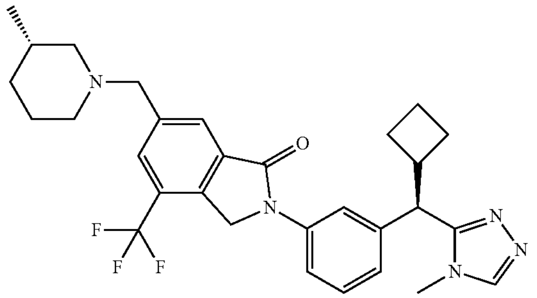 [SMILES: C[C@H]1CCCN(Cc2cc3c(c(C(F)(F)F)c2)CN(c2cccc([C@H](c4nncn4C)C4CCC4)c2)C3=O)C1] |
| 116 | 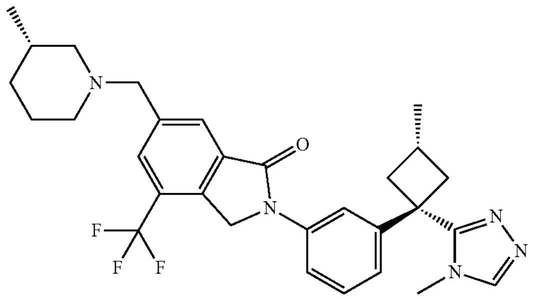 [SMILES: C[C@H]1CCCN(Cc2cc3c(c(C(F)(F)F)c2)CN(c2cccc([C@]4(c5nncn5C)C[C@@H](C)C4)c2)C3=O)C1] |
| 117 | 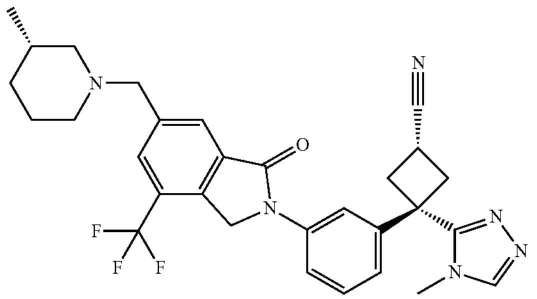 [SMILES: C[C@H]1CCCN(Cc2cc3c(c(C(F)(F)F)c2)CN(c2cccc([C@]4(c5nncn5C)C[C@@H](C#N)C4)c2)C3=O)C1] |
| 118 | 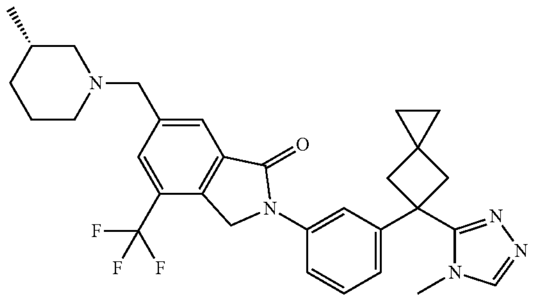 [SMILES: C[C@H]1CCCN(Cc2cc3c(c(C(F)(F)F)c2)CN(c2cccc(C4(c5nncn5C)CC5(CC5)C4)c2)C3=O)C1] |
| 119 | 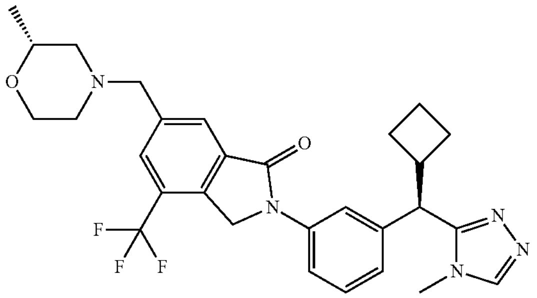 [SMILES: C[C@@H]1CN(Cc2cc3c(c(C(F)(F)F)c2)CN(c2cccc([C@H](c4nncn4C)C4CCC4)c2)C3=O)CCO1] |

TABLE 1-continued
| Compound No. | Structure |
|---|---|
| 120 | 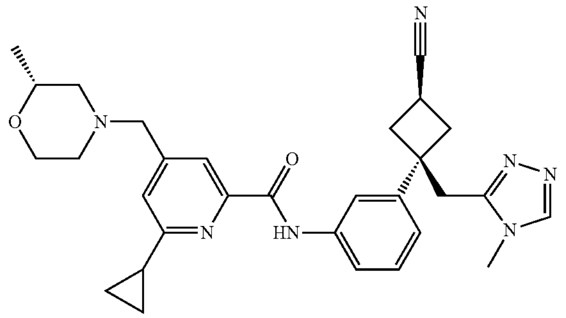 [SMILES: C[C@@H]1CN(Cc2cc(C(=O)Nc3cccc([C@]4(Cc5nncn5C)C[C@@H](C#N)C4)c3)nc(C3CC3)c2)CCO1] |
| 121 | 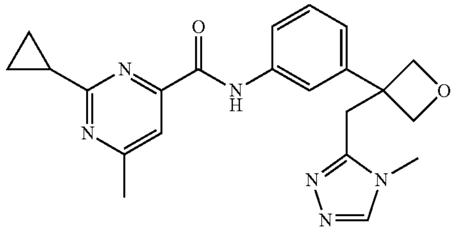 [SMILES: Cc1cc(C(=O)Nc2cccc(C3(Cc4nncn4C)COC3)c2)nc(C2CC2)n1] |
| 122 | 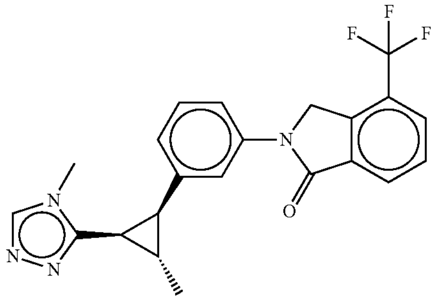 |
| 123 | 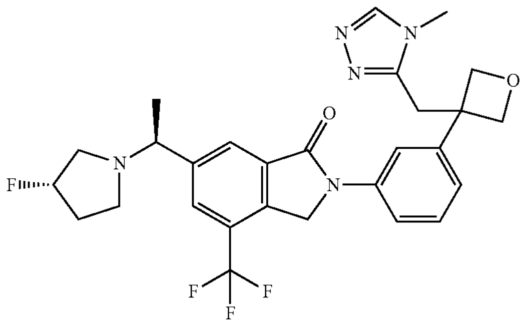 [SMILES: C[C@@H](c1cc2c(c(C(F)(F)F)c1)CN(c1cccc(C3(Cc4nncn4C)COC3)c1)C2=O)N1CC[C@H](F)C1] |
| 124 | 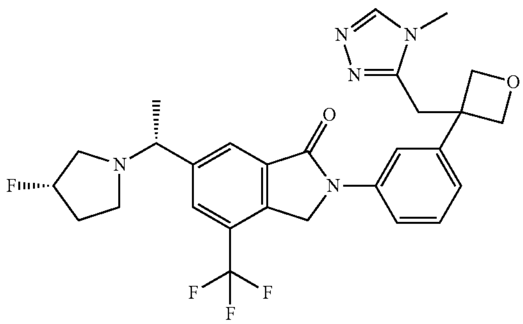 [SMILES: C[C@H](c1cc2c(c(C(F)(F)F)c1)CN(c1cccc(C3(Cc4nncn4C)COC3)c1)C2=O)N1CC[C@H](F)C1] |

TABLE 1-continued
| Compound No. | Structure |
|---|---|
| 125 | 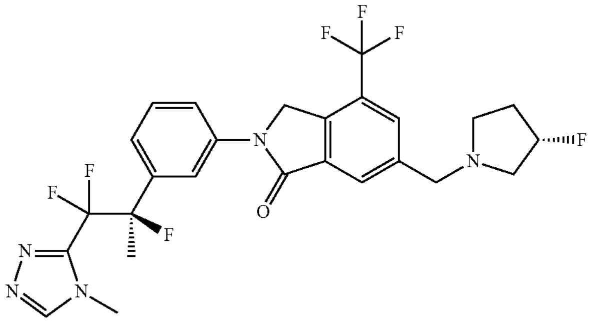 [SMILES: Cn1cnnc1C(F)(F)[C@](C)(F)c1cccc(N2Cc3c(cc(CN4CC[C@H](F)C4)cc3C(F)(F)F)C2=O)c1] |
| 126 | 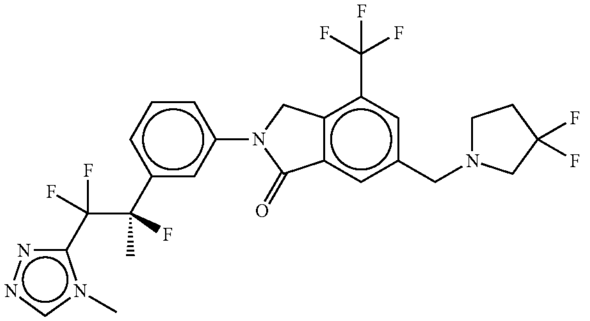 |
| 127 | 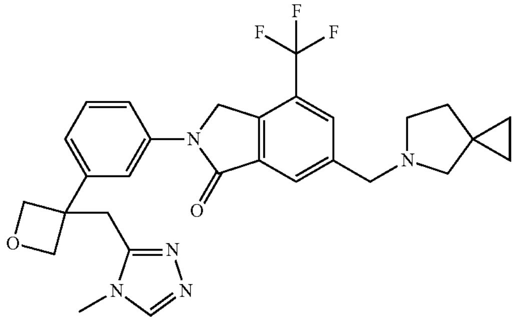 [SMILES: Cn1cnnc1CC1(c2cccc(N3Cc4c(cc(CN5CCC6(CC6)C5)cc4C(F)(F)F)C3=O)c2)COC1] |
| 128 | 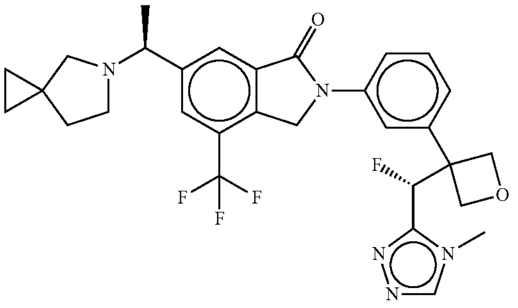 |
| 129 | 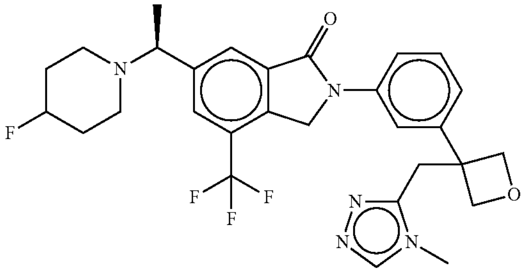 |

In some embodiments, provided for use in the compositions and methods described herein is a compound selected from compound Nos. 101-129 in Table 1, or a tautomer thereof, or a pharmaceutically acceptable salt of any of the foregoing.

In some embodiments, one or more of the small molecule Cbl inhibitors disclosed in WO 2019/148005, which is incorporated by reference in its entirety, are used in methods described herein.

The disclosure also includes any or all of the stereochemical forms, including any enantiomeric or diastereomeric forms of the compounds described herein, and cis/trans or E/Z isomers. Unless stereochemistry is explicitly indicated in a chemical structure or name, the structure or name is intended to embrace all possible stereoisomers of a compound depicted. In addition, where a specific stereochemical form is depicted, it is understood that all other stereochemical forms are also described and embraced by the disclosure, as well as the general non-stereospecific form and mixtures of the disclosed compounds in any ratio, including mixtures of two or more stereochemical forms of a disclosed in any ratio, such that racemic, non-racemic, enantioenriched and scalemic mixtures of a compound are embraced. Compositions comprising a disclosed compound also are intended, such as a composition of substantially pure compound, including a specific stereochemical form thereof. Compositions comprising a mixture of disclosed compounds in any ratio also are embraced by the disclosure, including compositions comprising mixtures of two or more stereochemical forms of a disclosed compound in any ratio, such that racemic, non-racemic, enantioenriched, and scalemic mixtures of a compound are embraced by the disclosure. If stereochemistry is explicitly indicated for one portion or portions of a molecule, but not for another portion or portions of a molecule, the structure is intended to embrace all possible stereoisomers for the portion or portions where stereochemistry is not explicitly indicated. The disclosure embraces any and all tautomeric forms of the compounds described herein.

The disclosure embraces all salts of the compounds described herein, as well as methods of using such salts of the compounds. In one embodiment, the salts of the compounds comprise pharmaceutically acceptable salts. Pharmaceutically acceptable salts are those salts that can be administered as drugs or pharmaceuticals to humans and/or animals and that, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, also can be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N'-dibenzylethylenediamine, and triethylamine salts. Salts of acidic compounds with amino acids, such as lysine salts, also can be prepared. For lists of pharmaceutically acceptable salts, see, for example, P. H. Stahl and C. G. Wermuth (eds.) "Handbook of Pharmaceutical Salts, Properties, Selection and Use" Wiley-VCH, 2011 (ISBN: 978-3-90639-051-2). Several pharmaceutically acceptable salts are also disclosed in Berge, J. Pharm. Sci. 66: 1 (1977).

In some embodiments, the Cbl inhibitors are prepared as disclosed in WO 2019/148005, which is incorporated by reference in its entirety. In some embodiments, the Cbl inhibitor(s) are commercially available from sources including but are not limited to Progenra, Inc.

In some embodiments, any of compounds 101-129, or a combination of two or more thereof, are used for the compositions and/or the methods described herein. In other embodiments, one or more of the Cbl inhibitor compounds as disclosed in WO 2019/148005, which is incorporated by reference in its entirety, are used as inhibitors in the methods of the disclosure.

In various embodiments, and as further described herein, Cbl inhibitor compounds as provided herein (as well as compositions comprising compounds described herein, and methods using the compounds or compositions) have $IC_{50}$ values of less than 1 nM, between 1 and 100 nM, between 100 nM-300 nM, between 301 nM-1000 nM, between 1,001 nM-3,000 nM, between 3,001 nM-10,000 nM, or greater than 10,000 nM as measured in an in vitro assay of Cbl inhibition as described in Biological Example 1 of WO 2019/148005. In a particular embodiment, the Cbl inhibitor has an $IC_{50}$ of between about 0.1 and 10 nM in an in vitro assay of Cbl inhibition as described in Biological Example 1 of WO 2019/148005. In a further embodiment, and as further described herein, compounds as provided herein (as well as compositions comprising compounds described herein, and methods using the compounds or compositions) have $IC_5$ values of less than 100 nM in an in vitro assay of Cbl inhibition as described in Biological Example 1 of WO 2019/148005. In a further embodiment, and as further described herein, compounds as provided herein (as well as compositions comprising compounds described herein, and methods using the compounds or compositions) have $IC_{50}$ values of between 100 nM-300 nM as determined in an in vitro assay of Cbl inhibition as described in Biological Example 1 of WO 2019/148005. In a further embodiment, and as further described herein, compounds as provided herein (as well as compositions comprising compounds described herein, and methods using the compounds or compositions) have $IC_{50}$ values of between 301 nM-1000 nM as determined in an in vitro assay of Cbl inhibition as described in Biological Example 1 of WO 2019/148005. In a further embodiment, and as further described herein, compounds as provided herein (as well as compositions comprising compounds described herein, and methods using the compounds or compositions) have $IC_{50}$ values of between 1,001 nM-3,000 nM as determined in an in vitro assay of Cbl inhibition as described in Biological Example 1 of WO 2019/148005. In a further embodiment, and as further described herein, compounds as provided herein (as well as compositions comprising compounds described herein, and methods using the compounds or compositions) have $IC_{50}$ values of between 3,001 nM-10,000 nM as determined in an in vitro assay of Cbl inhibition as described in Biological Example 1 of WO 2019/148005. In a further embodiment, and as further described herein, compounds as provided herein (as well as compositions comprising compounds described herein, and methods using the compounds or compositions) have $IC_{50}$ values of greater than 10,000 nM as determined in an in vitro assay of Cbl inhibition as described in Biological Example 1 of WO 2019/148005.

In some embodiments, the Cbl inhibitor is a synthetic or naturally occurring peptide. In some embodiments, the peptide is a fusion protein. The peptide may be, e.g., a DGpYMP peptide mimetic of tyrosine(608)-phosphorylated insulin receptor substrate-1 (IRS-1) (Cblin), or a fusion peptide, e.g., comprising a cell delivery portion and a casitas b-lineage lymphoma-b(Cbl) binding peptide, wherein the Cbl binding peptide has the sequence N/D$X_1$PY$X_2$P, wherein X, $X_1$ and $X_2$ are selected from any amino acid, N/D is either asparagine (N) or aspartic acid (D), and pY is phosphotyrosine binds to the tyrosine kinase binding (TKB) domain of Cbl, in some embodiments the Cbl binding peptide is a peptide fragment of spleen tyrosine kinase (Syk).

In some embodiments, the Chi inhibitor is an antibody, e.g., one that selectively binds a Cbl epitope thereby inactivating it Monoclonal and polyclonal anti-Cb antibodies can be used in the methods and compositions of the disclosure.

In some embodiments, the Cbl inhibitor is a nucleic acid, e.g., an siRNA that targets a Cbl protein, e.g. Cbl See, e.g., U.S. Pat. No. 10,421,945. siRNA compositions as described in U.S. Pat. Nos. 10,421,945, 9,186,373, or U.S. Pat. No. 8,809,288 can also be used in methods of the disclosure.

In certain embodiments, the Cbl inhibitors of the disclosure are administered orally, intravenously, subcutaneously, intratumorally, or by pulmonary administration in vivo, in an individual undergoing autologous cell-based immunotherapy, or administered orally, intravenously, subcutaneously or by pulmonary administration to a donor providing immune cells for allogeneic cell-based immunotherapy.

Harvesting Cells

In the cell therapy methods described herein, cells are harvested from a donor. The cells can be any cells deemed suitable by the person of skill. The harvesting can be according to standard techniques. In certain embodiments, immune cells are harvested from a donor. In certain embodiments, the immune cells are circulating immune cells and are harvested by apheresis. In certain embodiments, circulating cells are harvested by leukapheresis. In certain embodiments, immune cells are harvested from a tumor is obtained from a donor. In certain embodiment, the tumor is obtained from a donor via biopsy or surgical removal of a solid tumor tissue. In some embodiments, tumor tissue is removed from an individual and fragmented or subjected to enzymatic digestion to disrupt the extracellular matrix and/or mechanical disruption and make a tumor cell suspension prior to culturing from which the immune cells will be isolated. A initial cell population may be a heterogeneous cell population derived from peripheral blood, cord blood, a tumor or tumor biopsy, lymph, skin, tumor-infiltrating lymphocytes, or derived from stem cell precursors and induced pluripotent stems cells. The culturing conditions favor the growth of immune cells over the other cell types such that the resulting cell population is enriched with the desired immune cells.

For the methods described herein, the same removal and the expansion steps may be used whether or not the donor is pre-treated with Cbl inhibitor.

In some embodiments, between $10^6$ and $10^{10}$ cells are collected by leukapheresis for selection and expansion. In some embodiments, between $10^8$ and $10^{10}$ cells are collected by leukapheresis for selection and expansion. In some embodiments, between $10^9$ and $10^{10}$ cells are collected for selection and expansion.

In certain embodiments, tumor fragments, for instance between 1 $mm^3$ and 2 $cm^3$, are isolated from a patient for isolation and expansion of TIL. In some embodiments, the tumor fragments collected are between 0.5 $mm^3$ and 1 $cm^3$. In some embodiments, the tumor fragments are between 1 $mm^3$ and 8 $mm^3$. In some embodiments, the tumor fragments collected are between 1 $mm^3$ and 5 $mm^3$. In some embodiments, the tumor fragments collected are between 1 $mm^3$ and 3 $mm^3$.

In certain embodiments, one or more Cbl inhibitors enhance the harvesting step. In certain embodiments, one or more Cbl inhibitors activate immune cells in vivo prior to harvesting. In such embodiments, one or more Cbl inhibitors are administered to a donor in an amount sufficient to enhance the desired cells for harvest. In certain embodiments, one or more Cbl inhibitors are administered to an individual prior to harvest. In certain embodiments, the Cbl inhibitor enhances in vivo activation. In certain embodiments, the Cbl inhibitor enhances in vivo differentiation. In certain embodiments, the Cbl inhibitor enhances in vivo stimulation. In certain embodiments, the Cbl inhibitor enhances in vivo priming of cells. In some individuals, administration of the Cbl inhibitor stimulates proliferation of immune cells which specifically recognize a cancer or tumor from which a patient is suffering.

The dose of the Cbl inhibitor can be any dose deemed suitable by the person of skill. In certain embodiments, the dose is effective to enhance the cells desired for harvest. In certain embodiments, the dose is between 0.001-5000 mg, 0.01-2500 mg, 0.1-2000 mg, 1-1500 mg, 1-1000 mg, 1-750 mg, 1-500 mg, 1-400 mg, 1-300 mg, 1-250 mg, 1-200 mg, 1-100 mg, 1-10 mg, 0.1-10 mg, 0.1-5 mg, or 0.1-1 mg Cbl inhibitor. In certain embodiments, the dose is between 1-5000 mg, 1-2500 mg, 1-2000 mg, 1-1500 mg, 1-1000 mg, 1-750 mg, 1-500 mg, 1-400 mg, 1-300 mg, 1-250 mg, 1-200 mg, 1-100 mg, 1-10 mg, 0.1-10 mg, 0.1-5 mg, or 0.1-1 mg.

The dose is administered for a period of time on a schedule deemed suitable by the person of skill. In certain embodiments, the dosage is sufficient to enhance the cells desired to be harvested. In some embodiments, the period of treatment with Cbl inhibitor, i.e., the in vivo activation period, is from about 1 minute to about 1 hour, about 5 minutes to about 1 hour, about 10 minutes to about 1 hour, about 15 minutes to about 1 hour, about 20 minutes to about 1 hour, about 30 minutes to about 1 hour, about 45 minutes to about 1 hour, about 1 hour to about 2 hours, about 1 hour to about 4 hours, about 1 hour to about 6 hours, about 1 hour to about 8 hours, about 1 hour to about 12 hours, about 1 hour to about 24 hours, about 2 hours to about 24 hours, about 6 hours to about 7 hours, about 6 hours to about 24 hours, about 8 hours to about 24 hours, about 10 hours to about 24 hours, about 15 hours to about 24 hours, about 20 hours to about 24 hours, about 12 hours to about 48 hours, about 24 hours to about 48 hours, or about 36 hours to about 48 hours. In some embodiments, the in vivo activation period is about 1 minute, about 5 minutes, about 10 minutes, about 15 minutes, about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, or about 24 hours. In some embodiments, the in vivo activation period is about 1 day, about 2 days, about 3 days, about 4 days, about 5 days, about 6 days or about 7 days, 1 to 2 days, 1 to 3 days, 1 to 4 days, 1 to 5 days, 1 to 6 days, 1 to 7 days, 1 to 10 days, 1 to 14 days, 1 to 21 day, 1 to 28 days or 1 to 45 days, 1 to 60 days, 2 to 3 days, 2 to 4 days, 2 to 5 days, 2 to 6 days, 2 to 7 days, 2 to 10 days, 2 to 14 days, 2 to 21 days, 2 to 28 days or 2 to 45 days, 2 to 60 days, 4 to 5 days, 4 to 6 days, 4 to 7 days, 4 to 10 days, 4 to 14 days, 4 to 21 days, 4 to 28 days, 4 to 45 days, 4 to 60 days, 7 to 10 days, 7 to 14 days, 7 to 21 days, 7 to 28 days, 7 to 45 days or 7 to 60 days. In some embodiments, the length of the in vivo expansion phase is 0-4 days, 0-7 days, 0-11 days, 0-14 days, or 0-30 days.

In some embodiments, the Cbl inhibitor is administered in combination with an agent selected from the group consisting of IL-2, IL-4, IL-7, IL-12. IL-15, IL-21, or granulocyte-macrophage colony stimulating factor (G-MCSF) or a combination thereof. In some embodiments, the Cbl inhibitor is administered in combination with IL-2. In some embodiments, the Cbl inhibitor is administered in combination with IL-4. In some embodiments, the Cbl inhibitor is administered in combination with IL-7. In some embodiments, the Cbl inhibitor is administered in combination with IL-15. In some embodiments, the Cbl inhibitor is administered in combination with IL-7 and IL-15. In some embodiments, the Cbl inhibitor is administered in combination with IL-12. In some embodiments, the Cbl inhibitor is administered in combination with IL-21. In some embodiments, the Cbl inhibitor is administered in combination with G-MCSF.

In some embodiments, the biological activity of the donor's immune cell population is measured before and after activation and/or prior to harvest. Immune cells can be measured by methods known in the art. Parameters to assess include overall number, or activity of cells before and after activation. For example, specific binding of modified immune cell or other immune cell to antigen, in vivo (e.g., by imaging) or ex vivo (e.g., by ELISA or flow cytometry) may be measured. In some embodiments, the ability of immune cells to destroy target cells can be measured using any suitable method known in the art, such as cytotoxicity assays described in, for example, Kochenderfer et al., *J. Immunotherapy,* 32 (7): 689-702 (2009), and Herman et al. *J. Immunological Methods,* 285(1):25-40 (2004). In some embodiments, the biological activity of the immune cells also can be measured by assaying expression and/or secretion of certain cytokines, such as IL-2 and IFNγ. In some embodiments, the initial size and/or number of tumors is assessed prior to beginning treatment.

In some embodiments, the immune cells are derived from cell lines. In some embodiments, the immune cells are genetically engineered prior to expansion. In some embodiments, the immune cells are derived from a cell line selected from a T-cell line, a B cell line, and a NK cell line. In some embodiments, the immune cells to be selectively expanded or a cell population comprising the immune cells to be selectively expanded and optionally, genetically engineered, are derived from a cell line (e.g., a T-cell line, a B cell line, a NK cell line, etc.). In some embodiments, the immune cells are obtained from a xenogeneic source, such as from mouse, rat, non-human primate, or pig. In some embodiments, cell lines are exposed to a Cbl inhibitor prior to harvest for use in cell-based immunotherapy.

In certain embodiments, the harvested cells are formulated in cryopreservation media and placed in cryogenic storage units such as liquid nitrogen freezers (−195° C.) or ultra-low temperature freezers (−65° C., −80° C., or −120° C.) for long term storage of at least one month, 2 months, 3 months, 4 months, 6 months, 1 year, 2 years, 3 years, or at least 5 years. The cryopreservation medium can comprise glycerol, DMSO (dimethylsulfoxide), NaC, dextrose, dextran sulfate, and/or hydroxyethyl starch (HES) with culture media or physiological buffering agents to maintain a pH of 6.0 to 6.5, 6.5 to 7.0, 6.5 to 7.5, 7.0 to 7.5, 7.5 to 8.0. or 8.0 to 8.5. The frozen cells can be thawed and subjected to rounds of stimulation and/or expansion. In some embodiments, cryopreserved cells are thawed and genetically modified to express recombinant T cell receptors or chimeric T cell receptors.

In some embodiments, thawed cells are expanded by methods described herein. T cells can be further cryopreserved to generate cell banks in quantities of at least about 1, 5, 10, 100, 150, 200, or 500 vials at about at least $10^1$, $10^2$, $10^3$, $10^4$, $10^5$, $10^6$, $10^7$, $10^8$, $10^9$, or at least about $10^{10}$ cells per mL in freeze media. The cryopreserved cell banks may retain their functionality and can be thawed and further stimulated and expanded.

In some aspects, thawed cells can be stimulated and expanded in suitable closed vessels such as cell culture bags and/or bioreactors to generate quantities of cells as allogeneic cell product.

In certain embodiments, cryopreserved T cells maintain their biological functions for at least about 6 months, 7 months, 8 months, 9 months, 10 months, 11 months, 12 months, 13 months, 15 months, 18 months, 20 months, 24 months, 30 months, 36 months, 40 months, 50 months, or at least about 60 months under cryogenic storage conditions.

In certain embodiments, the harvested cell population is isolated or cultured under selective conditions wherein certain types of immune cells are enriched prior to the cell population being expanded ex vivo or in vitro. In some embodiments, the selective conditions enrich the cell population for a specific T cell population. In other embodiments, the selective conditions enrich the cell population for a preponderance of a desired T cell maturation level, phenotype, or specificity.

Genetically Modified Cells

In certain embodiments, harvested immune cells are genetically engineered, for instance, prior to expansion. In some embodiments, the immune cells are T cells and the T cells are genetically modified to express chimeric antigen receptor T cells (CAR T cells) or recombinant T cell receptors (TCR). T cells may be genetically modified to express CAR or TCR receptors to recognize cancer or malignancy-associated antigens by methods established in the art. See, e.g., Brenner et al., *Current Opinion in Immunology,* 22(2):251-257 (2010); Rosenberg et al., *Nature Reviews Cancer,* 8(4):299-308 (2008)). T cells can be genetically modified to express chimeric antigen receptors (CARs), which are fusion proteins comprised of an antigen recognition moiety and T cell activation domains. See, e.g., Eshhar et al., *Proc. Natl. Acad. Sci. USA,* 90(2):720-724 (1993), and Sadelain et al., *Curr. Opin. Immunol.,* 21(2): 215-223 (2009)). In some embodiments, the immune cells are NK cells and the NK cells are genetically modified to express chimeric antigen receptors (NK CAR cells) or recombinant T cell receptors (TCR).

Expansion of Immune Cells

In certain embodiments, the immune cells described herein are expanded in culture by any method deemed suitable by the person of skill. Standard techniques are useful here. In some embodiments, the expansion of immune cells ex vivo or in vitro is performed in one or more culture vessels comprising a gas permeable membrane. In other embodiments, the expansion of immune cells ex vivo or in vitro is performed using a G-Rex™ cell culture vessel (cell culture vessel that include a gas permeable rapid expansion cell culture membrane).

Circulating Immune Cells

In certain embodiments, the immune cells from blood are expanded in one round of expansion. In some embodiments, the immune cells are expanded using a culture vessel comprising a gas permeable membrane. In certain embodiments, the immune cells are expanded using single expansion using a G-Rex™ cell culture vessel. Advantageously, in some embodiments, expansion in the presence of a Cbl inhibitor yields a sufficient number and/or activity of immune cells.

In some embodiments, circulating immune cells are collected from a patient and expanded ex vivo to increase cell number to between about $10^9$ and about $2\times10^{11}$ cells prior to infusing the resulting cells into the patient. In certain embodiments, the Cbl inhibitor increases the number of cells relative to expansion in its absence. In certain embodiments, the Cbl inhibitor improves one or more phenotypes of the cells relative to expansion in its absence. In certain embodiments, the Cbl inhibitor decreases expansion time relative to expansion in its absence. In certain embodiments, expansion is complete after 10 or fewer days. In certain embodiments, the immune cells complete at least one additional doubling in culture with the Cbl inhibitor relative to expansion in its absence In certain embodiments, the immune cells from blood are expanded in one round of expansion. In some embodiments, the immune cells are expanded using a culture vessel comprising a gas permeable membrane. In certain embodiments, the immune cells are expanded using single expansion using a G-Rex™ cell culture vessel. Advantageously, in some embodiments, expansion in the presence of a Cbl inhibitor yields a sufficient number and/or activity of immune cells.

Tumor Immune Cells

In some embodiments, tumor immune cells are collected from a patient and expanded ex vivo twice—once for selective expansion of desired immune cells followed by a second expansion to increase cell number further to between about $10^9$ and about $2\times10^{11}$ cells ("double expansion") prior to infusing the resulting cells into the patient. In other embodiments, immune cells are collected from a patient and expanded ex vivo only once to a cell number between about $10^9$ and about $2\times10^{11}$ cells ("single expansion") prior to infusing the resulting cells into the patient. In other embodiments, the single expansion occurs in a G-Rex™ cell culture vessel. In some embodiments, the double expansion occurs in a single cell culture vessel. In other embodiments, the double expansion occurs in the same G-Rex™ cell culture vessel.

Expansion Culture

In certain methods, cells undergoing expansion are cultured in the presence of one or more agents or compounds to facilitate propagation, including enrichment of cells of particularly desired maturation levels prior to being infused into an individual in need thereof. Useful compounds include proinflammatory cytokines, such as IL-2, IL-4, IL-7, IL-12, IL-15, IL-21 or combination thereof. In some embodiments, the cytokine is IL-2. In some embodiments, the cytokine is IL-4. In some embodiments, the cytokine is IL-7. In some embodiments, the cytokine is IL-12. In some embodiments, the cytokine is IL-15. In some embodiments, the cytokine is IL-7 and IL-15 in combination. In some embodiments, the cytokine is IL-21. In some embodiments, the cytokine is IL-2, IL-7, and IL-15 in combination.

Each cytokine can be used at a concentration of between 0 and 25000 IU/ml, or between 0 and 10,000 IU/ml, or between 0 and 5000 IU/ml, or between 0-2500 IU/ml, or between 0-1000 IU/ml, or between 0-500 IU/ml, or between 0-100 IU/ml. The cytokines used during expansion may optionally be replenished during the culture period to replace the amount used by the cells during culture.

In certain methods, the cells undergoing expansion are provided additional IL-2 to replenish the amount used by the cells during culture. In some embodiments, IL-2 is replenished during single expansion. In other embodiments, IL-2 is replenished during double expansion but only the selective expansion phase. In other embodiments, IL-2 is replenished during double expansion but only during the second expansion phase. In other embodiments, IL-2 is replenished during double expansion during both the selective expansion phase and the second expansion phase. In other embodiments, IL-2 is added to the culture, every 2, 3, 4, 5, 6, 7, 8, 9, 10, or 11 days (whether during a single expansion, selective expansion, second expansion, or both selective expansion and second expansion). In other embodiments, IL-2 is replenished only once, twice, or three times during expansion (whether during a single expansion, selective expansion, second expansion, or both selective expansion and second expansion).

In certain methods, the cells undergoing expansion are provided additional IL-7 and IL-15 to replenish the amount used by the cells during culture. In some embodiments, IL-7 and IL-15 are replenished during single expansion. In other embodiments, IL-7 and IL-15 are replenished during double expansion but only the selective expansion phase. In other embodiments, IL-7 and IL-15 are replenished during double expansion but only during the second expansion phase. In other embodiments, IL-7 and IL-15 are is replenished during double expansion during both the selective expansion phase and the second expansion phase. In other embodiments, IL-7 and IL-15 are added to the culture, every 2, 3, 4, 5, 6, 7, 8, 9, 10, or 11 days (whether during a single expansion, selective expansion, second expansion, or both selective expansion and second expansion). In other embodiments, IL-7 and IL-15 are replenished only once, twice, or three times during expansion (whether during a single expansion, selective expansion, second expansion, or both selective expansion and second expansion).

In certain methods, the cells are cultured in the presence of an immunostimulatory agent. In some embodiments, the immunostimulatory agent is a compound that binds to a surface receptor of an immune cell. The surface receptor can be any such surface receptor recognized by the person of skill in the art. In some embodiments, the immunostimulatory agent is a compound that binds to a T cell receptor. In some embodiments, the immunostimulatory agent is a compound that binds to CD3. In some embodiments, the immunostimulatory agent is an anti-CD3 antibody. In some embodiments, the immunostimulatory agent is a compound that binds to CD28. In some embodiments, the immunostimulatory agent is an anti-CD28 antibody. In some embodiments, the immunostimulatory agent is combination of an anti-CD3 antibody and an anti-CD28 antibody. In other embodiments, the immunostimulatory agent is immobilized on a surface. In other embodiments, the immunostimulatory agent is immobilized on a magnetic bead.

In certain methods, cells are cultured in the presence of feeder cells. The feeder cells are typically treated so they themselves do not proliferate but instead aid in the proliferation or the activation of the immune cells as a source of either stimulating agent or beneficial agent or both. In some embodiments, the feeder cells are irradiated. Generally, feeder cells are used for expanding immune cells harvested from tumors and are typically added during the second expansion phase of double expansion. In some embodiments, the feeder cells are irradiated peripheral blood mononuclear cells. In certain embodiments, the feeder cells are added during the second expansion, and the feeder cells are irradiated peripheral blood mononuclear cells.

In certain methods, the cells are cultured in the presence of both feeder cells and an immunostimulatory agent. Generally, the combination of feeder cells and immunostimulatory agent are used for expanding immune cells harvested from tumors and are typically added during the second expansion phase of double expansion. In some embodiments, the feeder cells are irradiated peripheral blood mononuclear cells and the immunostimulatory agent is an anti-CD3 antibody.

In certain embodiments, one or more expansion steps is enhanced with a Cbl inhibitor. Advantageously, the Cbl inhibitor can reduce the time of the expansion step and in cases where multiple expansions are needed, eliminate the additional one or more expansion steps. In certain embodiments, the Cbl inhibitor can reduce or eliminate the need for additional immunostimulatory agents. In certain embodiments, the Cbl inhibitor eliminates the need for feeder cells. In certain embodiments, the Cbl inhibitor eliminates the need for immunostimulator agents and for feeder cells. In certain embodiments, the expansion steps proceed in the absence of irradiated peripheral blood mononuclear cells. In certain embodiments, the expansion steps proceed in the absence of anti-CD3 antibody. In certain embodiments, the expansion steps proceed in the absence of OKT3. In certain embodiments, the expansion steps proceed in the absence of 4-IBB agonist, e.g. 4-BBL. In certain embodiments, the expansion steps proceed in the absence of irradiated peripheral blood mononuclear cells, in the absence of anti-CD3 antibody, and in the absence of 4-IBB agonist. In certain embodiments, the expansion steps proceed in presence of Cbl inhibitor and TL-2 as described herein, in the absence of irradiated peripheral blood mononuclear cells, in the absence of anti-CD3 antibody, e.g. OKT3, and in the absence of 4-IBB agonist, e.g. 4-BBL. In certain embodiments, the expansion steps proceed in presence of Cbl inhibitor, IL-2, OKT3, and irradiated peripheral blood mononuclear cells, as described herein and in the absence of 4-IBB agonist, e.g. 4-BBL.

In certain embodiments, the methods comprise expansion in the presence of a Cbl inhibitor. In certain embodiments, the methods comprise expansion in the presence of a Cbl inhibitor and no additional immunostimulatory agent. In certain embodiments, the methods comprise expansion in the presence of a Cbl inhibitor and without the addition of feeder cells. In certain embodiments, the methods comprise expansion in the presence of a Cbl inhibitor and without a second expansion step. In certain embodiments, the methods comprise expansion in the presence of a Cbl inhibitor without the addition of an immunostimulatory agent and without a second expansion step. In certain embodiments, the methods comprise expansion in the presence of a Cbl inhibitor without the addition of feeder cells and without a second expansion step.

In certain embodiments, immune cells are cultured ex vivo or in vitro in the presence of a Cbl inhibitor, at a concentration of between 1 μM to about 100 mM, about 0.001 μM to about 100 μM, about 0.01 μM to about 50 μM, about 0.001 nM to about 50 μM, about 100 nM to about 10 μM, about 0.01 μM to about 25 μM, about 0.1 μM to about 15 μM, about 1 μM to about 10 μM, about 0.1 μM to about 100 nM, about 1 μM to about 10 nM, about 1 μM to about 1 nM, In some embodiments, the concentration of a Cbl inhibitor added to a composition (e.g., cell culture medium) comprising the immune cells is about 1 μM, about 2 μM, about 3 μM, about 4 μM, or about 5 μM. In some embodiments, the concentration of a Cbl inhibitor added to a composition (e.g., cell culture medium) comprising the immune cells is about 1 μM. In some embodiments, the concentration of a Cbl inhibitor added to a composition (e.g., cell culture medium) comprising the immune cells is between about 0.1 to about 1 μM. In some embodiments, the concentration of a Cbl inhibitor added to a composition (e.g., cell culture medium) comprising the immune cells is about 1 μM.

In certain methods, the cells undergoing expansion in the presence of Cbl inhibitor are provided additional Cbl inhibitor to replenish the amount used by the cells during culture. In some embodiments, the Cbl inhibitor is replenished during single expansion. In other embodiments, the Cbl inhibitor is replenished during double expansion but only during the selective expansion phase. In other embodiments, the Cbl inhibitor is replenished during expansion but only during the second expansion phase. In other embodiments, the Cbl inhibitor is replenished during expansion during both the selective expansion phase and the second expansion phase. In other embodiments, the Cbl inhibitor is added to the culture every 2, 3, 4, 5, 6, 7, 8, 9, 10, or 11 days during expansion (whether during a single expansion, selective expansion, second expansion or both selective expansion and second expansion). In other embodiments, the Cbl inhibitor is replenished only once, twice, or three times during expansion (whether during a single expansion, selective expansion, second expansion, or both selective expansion and second expansion).

In certain methods, the cells are cultured during ex vivo expansion without the addition feeder cells and without an anti-CD3 and/or without anti-CD28 antibody, and Cbl inhibitor or IL-2 is added to the culture every 2 or 3 days. In some embodiments, the cells are cultured using single expansion without the addition of irradiated peripheral blood mononuclear cells and without an anti-CD3 antibody, and where Cbl inhibitor and IL-2 are added to the culture every 2 or 3 days. In other embodiments, the cells are cultured using double expansion without the addition of irradiated peripheral blood mononuclear cells and without an anti-CD3 antibody during the second expansion phase, and where Cbl inhibitor and IL-2 are added to the culture every 2 or 3 days during the selective expansion phase and the second expansion phase.

In certain embodiments, immune cells are subjected to expansion using methods described herein for a period of from about 1 day to about 48 days, about 7 days to about 28 days, about 7 days to about 24 days, about 11 days to about 24 days, 1 day to about 28 days, about 2 days to about 24 days, about 3 days to about 20 days, about 4 days to about 17 days, about 5 days to about 15 days, about 5 days to about 14 days, about 5 days to about 12 days, about 6 days to about 14 days, about 6 days to about 12 days, or about 8 days to about 14 days.

In some embodiments, the expansion is a single expansion and is for a period from about 7 days to about 28 days. In other embodiments, the expansion is a single expansion and is for a period from about 11 to about 28 days. In other embodiments, the expansion is a single expansion and is for a period from about 10 days to about 24 days. In other embodiments, the expansion is a single expansion and is for a period from about 7 days to about 14 days. In other embodiments, the expansion is a single expansion and is for 10 days. In other embodiments, the expansion is a single expansion and is for 11 days.

In some embodiments, the expansion is a double expansion wherein the selective expansion is from about 3 days to about 7 days, about 3 days to 8 days, about 3 days to 10 days, about 3 days to 12 days, about 3 days to 14 days, 3 days to 18 days, 3 days to 22 days, about 4 days to about 7 days, about 4 days to 8 days, about 4 days to 10 days, about 4 days to 12 days, about 4 days to 14 days, about 4 days to 18 days, about 4 days to about 22 days, about 5 days to 8 days, about 5 days to 10 days, about 5 days to about 18 days, about 5 days to about 21 days, about 5 days to about 28 days, about 6 days to 8 days, about 6 days to 10 days, about 6 days to 12 days, about 6 days to 14 days, about 6 days to about 18 days, about 6 days to about 21 days, about 6 days to about 28 days, about 7 days to 8 days, about 7 days to 10 days, about 7 days to 12 days, about 7 days to 14 days, about 7 days to about 18 days, about 7 days to about 21 days, about 8 days to 10 days, about 8 days to 12 days, about 8 days to 14 days, about 8 days to about 18 days, about 8 days to about 21 days, or about 8 days to about 28 days. In other embodiments, the expansion is a double expansion wherein the second expansion is from about 3 days to about 15 days, about 4 days to 14 days, about 5 days to 13 days, about 6 days to 12 days, about 7 days to 1 days, about 6 days to about 18 days, about 6 days to about 21 days, about 6 days to about 28 days, about 7 days to 8 days, about 7 days to 10 days, about 7 days to 12 days, about 7 days to 14 days, about 7 days to about 18 days, about 7 days to about 21 days, about 8 days to 10 days, about 8 days to 12 days, about 8 days to 14 days, about 8 days to about 18 days, about 8 days to about 21 days, or about 8 days to about 28 days.

In some embodiments, the total period of expansion ex vivo is for about 1 day, about 2 days, about 3 days, about 4 days, about 5 days, about 6 days, about 7 days, about 8 days, about 10 days, about 11 days, about 12 days, about 14 days, about 18 days, about 22 days or about 28 days. In other embodiments, the total period of expansion ex vivo is between 10 days and 14 days. In still other embodiments, the total period of expansion ex vivo is between 14 days and 22 days. In a preferred embodiment, cells are expanded for less than 14 days prior to infusion into a cancer patient or patient in need thereof. In a more preferred embodiments, cells are expanded for less than 11 day prior to infusion into a cancer patient or a patient in need thereof.

Phenotype of Expanded Immune Cells

In general, the desired phenotype of the infusion population (immune cells that are infused into a patient) includes traits that are correlated with better patient treatment outcomes. As such, the desired phenotype in certain embodiments will be the same regardless of the starting population of cells (e.g., whether the expanded immune cells are used directly or whether the expanded immune cells are further screened for a desirable property).

In certain methods, the expanded immune cells are screened for a desirable property, and a subpopulation of the expanded cells are selected for infusion into a patient. In this case, the starting population is the expanded immune cells, and the infusion population is the subset of the expanded cells that were selected for infusion. In some embodiments, the infusion population is enriched with immune cells exhibiting tumor recognition activity. In other embodiments, the infusion population is enriched with immune cells expressing an engineered T cell receptor. In other embodiments, the infusion population is enriched with immune cells expressing an engineered chimeric antigen receptor.

In certain embodiments, immune cells expanded in the presence of a Cbl inhibitor are already enriched for the cells having desirable properties. As a consequence, the immune cells that are expanded in the presence of a Cbl inhibitor in certain embodiments do not need a further selection step to identify a desirable subpopulation for infusion in a patient.

In some embodiments, the expanded immune cells are screened for their ability to produce IL-2 and/or IFNγ, and a subpopulation of cells enriched for IL-2 or IFNγ-producing cells is selected. In other embodiments, the immune cells are screened for T cell phenotype using maturation stage-specific markers, and a subpopulation of cells enriched for the desired maturation stage is selected. For example, a desirable property may be immune cells expressing one or more of the following markers: CD8+, CD45RA+, CD45RA−, CD45RO+, CD45RO−, CD95+, CD95−, CCR7+, CD62L+, CD62L−, CCR7−, CD56+, IL-2Rβ+, and IL-2Rβ−. In other embodiments, the immune cells are screened for T cells with a memory phenotype and a subpopulation of cells enriched for memory T cells is selected. In other embodiments, the immune cells are screened for $T_{CM}$ or $T_{SCM}$ cells and a subpopulation of cells enriched for $T_{CM}$ or $T_{SCM}$ cells is selected. Methods for distinguishing $T_{CM}$ and $T_{SCM}$ are described by, for example, Schmueck-Henneresse et al., *J. Immunol.,* 194(11):5559-5567 (2015) and Berger et al., *J. Cin. Invest.,* 118(1):294-305 (2008).

In some embodiments, the infusion population comprises a greater percentage and/or larger number of TIL than the starting population. In other embodiments, the infusion population comprises a greater percentage and/or larger number of T cells than the starting population. In other embodiments, the infusion contains a greater percentage and/or larger number of $T_{CM}$ or $T_{SCM}$ cells than the starting population. In other embodiments, the infusion population contains a greater percentage and/or higher number of $T_{EM}$ cells than the starting population. In other embodiments, the infusion population contains a lower percentage and/or lower number of naïve T cells than the starting population.

In some embodiments described herein, the infusion population comprises between about 10 and about 20% memory T cells. In other embodiments, the infusion population comprises between about 5 and about 40% memory T cells. In still other embodiments the infusion population comprises between about 10 and about 30% memory T cells. In some embodiments, the memory T cells are $T_{CM}$ or $T_{SCM}$. In some embodiments, the memory T cells are $CD45RO^+$ cells.

In certain embodiments, the methods provide expanded TIL that are enriched for CD8+ cells. In certain embodiments, the methods provide expanded TIL that have decreased amounts of CD4+ cells. In certain embodiments, the methods provide expanded TIL that are enriched for CD8+ central memory cells. In certain embodiments, the methods provide expanded TIL that have increased secretion of CD107a. In certain embodiments, the methods provide expanded TIL that have increased secretion of granzyme, for instance granzyme B. In certain embodiments, the methods provide expanded TIL that have increased secretion of one or more cytokines. In certain embodiments, the cytokines are selected from IFN-γ, TNF-α, GMCSF, MIP1α, MIP1βb, IP10, IL-2, IL-8, IL-7, IL-21, IL-23, and combinations thereof. As used herein, enrichment or increase or decrease is relative to similar TIL that are harvested or expanded in the absence of Cbl inhibitor. In certain embodiments, the enrichment, increase, or decrease is by 10%, 20%, 30%, 40%, 50%, 100%, 200%, or more. Amounts can be measured by standard techniques such as those described in the Examples herein.

In some embodiments, the infusion population is formulated in cryopreservation media and placed in cryogenic storage units such as liquid nitrogen freezers (−195° C.) or ultra-low temperature freezers (−65° C., −80° C., or −120° C.) for long term storage of at least one month, 2 months, 3 months, 4 months, 6 months, 1 year, 2 years, 3 years, or at least 5 years. The cryopreservation medium can comprise glycerol, DMSO (dimethylsulfoxide), NaCl, dextrose, dextran sulfate, and/or hydroxyethyl starch (HES) with culture media or physiological buffering agents to maintain a pH of 6.0 to 6.5, 6.5 to 7.0, 6.5 to 7.5, 7.0 to 7.5, 7.5 to 8.0. or 8.0 to 8.5. The frozen cells can be thawed and subjected to additional rounds of stimulation and/or expansion. Cryopreserved T cells maintain their biological functions for at least about 6 months, 7 months, 8 months, 9 months, 10 months, 11 months, 12 months, 13 months, 15 months, 18 months, 20 months, 24 months, 30 months, 36 months, 40 months, 50 months, or at least about 60 months under cryogenic storage condition. In some aspects, no preservatives are used in the formulation. The cryopreserved T cells can be thawed and administered to (e.g., infused into) multiple patients as allogeneic off-the-shelf cell product.

Methods of Treatment

In the cell therapy methods provided herein, expanded cells are administered to a patient in need thereof. In certain embodiments, the patient is the same as the donor. In certain embodiments, the patient and the donor are not the same individual. In certain embodiments, the donor is xenogeneic, and the patient is human. In some embodiments, patients are administered autologous cells according to methods described herein. In some embodiments, patients are administered allogeneic cells according to methods described herein.

Methods of cell-based immunotherapy are disclosed herein. Cell-based immunotherapy methods include, adoptive cell therapy, tumor infiltrating lymphocytes (TIL)-based therapy, chimeric T cell receptor (CAR) T cell therapy, engineered T-cell receptor (TCR) therapy, natural killer cell (NK) therapy, or natural killer chimeric antigen receptor therapy (NK CAR). In some embodiments, individuals may be administered the infusion population in more than one session of treatment.

In certain embodiments, the methods comprise administering to an individual in need of treatment, a composition comprising an effective amount of the immune cells that have been produced ex vivo or in vitro as provided herein. Therapeutically effective doses of the infusion population can be in the range of about one million to about 200 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges. In some embodiments, the method comprises administering between $2\times10^6$ and $2\times10^8$ viable immune cells per kg of body weight.

The infusion population and compositions thereof can be administered to an individual in need thereof using standard administration techniques, formulations, and/or devices. Provided are formulations and administration with devices, such as syringes and vials, for storage and administration of the compositions. Formulations or pharmaceutical composition comprising the immune cells include those for intravenous, intraperitoneal, subcutaneous, intramuscular, or pulmonary administration. In some embodiments, the immune cells are administered parenterally. The term "parenteral," as used herein, includes intravenous, intramuscular, subcutaneous, rectal, vaginal, and intraperitoneal administration. In some embodiments, the cell populations are administered to a subject using peripheral systemic delivery by intravenous, intraperitoneal, or subcutaneous injections. Compositions of the modified immune cells can be provided as sterile liquid preparations, e.g., isotonic aqueous solutions, suspensions, emulsions, dispersions, or viscous compositions, which may in some aspects be buffered to a selected pH. Viscous compositions can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof. Sterile injectable solutions can be prepared by incorporating the immune cells in a solvent, such as in admixture with a suitable carrier, diluent, or excipient such as sterile water, physiological saline, glucose, dextrose, or the like.

In some embodiments, the infusion population is co-administered with one or more additional therapeutic agents or in connection with another therapeutic intervention, either simultaneously or sequentially in any order.

In some embodiments, the individual undergoes a preparative regimen prior to being administered the infusion population of immune cells. For example, prior to receiving the infusion population, the individual may undergo one or more of the following: immunosuppression, immunodepletion, lymphocyte clearance, or stem cell flushing.

Agents that may be used for immunosuppression include, but are not limited to cyclosporine, tacrolimus, rilonacept, canakinumab, brodalumab, anakinra, reslizumab, ustekinumab, mepolizumab, tocilizumab, dupilumab, ixekizumab, secukinumab, guselkumab, tildrakizumab, benralizumab, sarilumab, basiliximab, risankizumab, siltuximab, daclizumab, pomalidomide, methotrexate, omalizumab, azathioprine, lenalidomide, thalidomide, alefacept, sirolimus, efalizumab, mycophenolic acid, mycophenolate mofetil, belimumab, natalizumab, fingolimod, leflunomide, dimethyl fumarate, everolimus, abatacept, teriflunomide, vedolizumab, everolimus, emapalumab, siponimod, belatacept, baricitinib, muromonab-cd3, eculizumab, ravulizumab, everolimus, etanercept, infliximab, golimumab, certolizumab, or adalimumab.

Agents that can be used for immunodepletion include, but are not limited to cyclophosphamide (Cytoxan), fludarabine, bendamustine, cisplatin, etoposide, paclitaxel, and gemcitabine.

Agents that can be used for lymphocyte clearance include, but are not limited to: etodolac.

Agents that can be used for stem cell mobilization or flushing include, but are not limited to G-CSF, pegfilgrastim, cyclophosphamide, and plerixafor (Mozobil, Genzyme).

In some embodiments, a Cbl inhibitor is administered in conjunction with one of these agents as supplemental pre-infusion treatment.

In some embodiments of the disclosure, individuals undergo immunosuppression, immunodepletion, lymphocyte clearance, or stem cell flushing prior to treatment, for 0-60 days 0-30 days, 0-15 days, 0-14 days, 0-13 days, 0-12 days, 0-11 days, 0-10 days, 0-9 days, 0-8 days, 0-7 days, 0-6 days, 0-5 days, 0-4 days, 0-3 days 0-2 days or 0-1 day prior to infusion of cells.

In some embodiments, the patient is conditioned by immunodepletion with a combination of cyclophosphamide and fludarabine. The cyclophosphamide and fludarabine can be administered according to standard techniques. In certain embodiments, the administration of cyclophosphamide is at a dose of between about 200 mg/$m^2$/day and about 2000 mg/$m^2$/day (e.g., 200 mg/$m^2$/day, 300 mg/$m^2$/day, or 500 mg/$m^2$/day). In certain embodiments, the dose of cyclophosphamide is about 300 mg/$m^2$/day. In certain embodiments, the administration of fludarabine is at a dose of between about 20 mg/$m^2$/day and about 900 mg/$m^2$/day (e.g., 20 mg/$m^2$/day, 25 mg/$m^2$/day, 30 mg/$m^2$/day, or 60 mg/$m^2$/day). In certain embodiments, the dose of fludarabine is about 25 mg/$m^2$/day. In certain embodiments, the administration of cyclophosphamide is at a dose of between about 200 mg/$m^2$/day and about 2000 mg/$m^2$/day (e.g., 200 mg/$m^2$/day, 300 mg/$m^2$/day, or 500 mg/$m^2$/day), and the administration of fludarabine is at a dose of between about 20 mg/$m^2$/day and about 900 mg/$m^2$/day (e.g., 20 mg/$m^2$/day, 25 mg/$m^2$/day, 30 mg/$m^2$/day, or 60 mg/$m^2$/day). In certain embodiments, the administration of cyclophosphamide is at a dose of about 500 mg/$m^2$/day, and the administration of fludarabine is at a dose of about 30 mg/$m^2$/day. In an exemplary embodiment, the dosing of cyclophosphamide is 500 mg/$m^2$/day over three days, and the dosing of fludarabine is 30 mg/$m^2$/day over three days. Dosing of lymphodepletion may be scheduled on Days −6 to −4 (with a +/−1 day window, i.e., dosing on Days −7 to −5) relative to T cell infusion on Day 0. Dosing of lymphodepletion may be scheduled on Days −5 to −3 (with a +/−1 day window, i.e., dosing on Days −4 to −2) relative to T cell infusion on Day 0.

In some embodiments, the patient is administered a cytokine with cell therapy. In certain embodiments, the cytokine is IL-2. The IL-2 is administered according to standard techniques. In certain embodiments, the IL-2 is administered at a dose of 100,000 IU/kg to 1,000,000 IL/kg. In certain embodiments, the IL-2 dose is from 400,000 IU/kg to 800,000 IU/kg. In certain embodiments, the IL-2 dose is about 600,000 IU/kg. Dosing of cytokine may be scheduled on Days 1 to 3 (with a +/−1 day window, i.e., dosing on Days 2 to 4) relative to T cell infusion on Day 0. In certain embodiments, cytokine is administered every eight hours for a total of six doses over the dosing schedule. In certain embodiments, IL-2 is administered every eight hours for a total of six doses on Days 1 to 3.

In some embodiments, individuals may have the modified cells infused in more than one session of treatment.

In some embodiments of the disclosure, cell-based immunotherapy is administered in combination with another anti-cancer therapy.

Combination Therapy with Cbl Inhibitor

In certain embodiments, the cell therapy is administered in combination with one or more Cbl inhibitors. For instance, in some therapeutic regimens of the present disclosure, both the modified immune cells and a Cbl inhibitor are administered to a subject in need thereof, wherein the Cbl inhibitor is a compound described herein or a pharmaceutically acceptable salt or solvate thereof.

In some embodiments, one or more of the small molecule Cbl inhibitors disclosed in WO 2019/148005, which is incorporated by reference in its entirety, are used in a treatment method described herein. In certain embodiments, the Cbl inhibitor is according to Formula (A). In certain embodiments, the Cbl inhibitor is selected from compounds 101-129. In certain embodiments, the Cbl inhibitor is compound 116. In certain embodiments, a combination of Cbl inhibitors is used. In certain embodiments, the Cbl inhibitor is an antibody. In certain embodiments, the Cbl inhibitor is a peptide. In certain embodiments, the Cbl inhibitor is an siRNA.

In certain embodiments, Cbl inhibitors are administered to a patient receiving therapeutic cells to support engraftment of said cells.

In some of these embodiments, said cells to be engrafted are organized as tissues or organs. In these embodiments, one or more Cbl inhibitors are administered to support engraftment of transplanted bone marrow, skin, corneas, tendons, bone tissue, blood vessels, or heart valves. In some embodiments, Cbl inhibitors are administered to support engraftment of one or more transplanted organs selected from a group comprising transplantable organs including heart, lung, kidney, liver, and pancreas. In other embodiments, Cbl inhibitors are administered to a patient receiving immune cells to support engraftment of said immune cells.

The daily dosage of a Cbl inhibitor for an individual receiving therapeutic cells to support engraftment of said therapeutic cells is between 1-5000 mg, 1-2500 mg, 1-2000 mg, 1-1500 mg, 1-1000 mg, 1-750 mg, 1-500 mg, 1-400 mg, 1-300 mg, 1-250 mg, 1-200 mg, 1-100 mg, 1-10 mg, 0.1-10 mg, 0.1-5 mg, or 0.1-1 mg.

Patients receiving therapeutic cells may be administered Cbl inhibitors to support engraftment of said cells for 1 to 2 days, 1 to 3 days, 1 to 4 days, 1 to 5 days, 1 to 6 days, 1 to 7 days, 1 to 10 days, 1 to 14 days, 1 to 21 days, 1 to 28 days, 1 to 45 days, 1 to 60 days, 2 to 3 days, 2 to 4 days, 2 to 5 days, 2 to 6 days, 2 to 7 days, 2 to 10 days, 2 to 14 days, 2 to 21 days, 2 to 28 days, 2 to 45 days, 2 to 60 days, 4 to 5 days, 4 to 6 days, 4 to 7 days, 4 to 10 days, 4 to 14 days, 4 to 21 days, 4 to 28 days, 4 to 45 days, 4 to 60 days, 7 to 10 days, 7 to 14 days, 7 to 21 days, 7 to 28 days, 7 to 45 days, or 7 to 60 days post-infusion of immune cells.

An effective amount of a Cbl inhibitor for supporting the engraftment of therapeutic cells received via an infusion, upon administration to a patient in need thereof, results in a concentration of said Cbl inhibitor of between 0-0.5 μM, 0-1 μM, between 0-5 μM, between 0-10 μM, between 0-25 μM, between 0-50 μM, between 0-100 μM, or between 0-1000 μM within the patient.

In certain embodiments, in addition to the Cbl inhibitor, one or more agents or compounds selected from a group comprising IL-2, IL-7, IL-15, IL-21, and combinations thereof are also administered to the patient after an infusion of therapeutic cells to facilitate engraftment of the infused therapeutic cells. In certain embodiments, the additional agent is IL-2. In certain embodiments, the additional agent is IL-7. In certain embodiments, the additional agent is IL-15. In certain embodiments, the additional agent is IL-21. In certain embodiments, the additional agent is a combination of IL-7 and IL-15. In certain embodiments, the one or more agents include cyclophosphamide and fludarabine.

In certain embodiments, administration of the Cbl inhibitor reduces or even eliminates the need for administration of any or all of the one or more additional agents. In certain embodiments, cyclophosphamide is administered at a dose reduced compared to therapy without the Cbl inhibitor. In certain embodiments, fludarabine is administered at a dose reduced compared to therapy without the Cbl inhibitor. In certain embodiments, IL-2 is administered at a dose reduced compared to therapy without the Cbl inhibitor. In certain embodiments, IL-2 is not administered. In certain embodiments, the administration of cyclophosphamide is at a dose of about 500 $mg/m^2/day$, and the administration of fludarabine is at a dose of about 25 $mg/m^2/day$. In an exemplary embodiment, the dosing of cyclophosphamide is 500 $mg/m^2/day$ over three days, and the dosing of fludarabine is 25 $mg/m^2/day$ over three days. Dosing of lymphodepletion may be scheduled on Days −5 to −3 (with a +/−1 day window, i.e., dosing on Days −4 to −2) relative to T cell infusion on Day 0. In certain embodiments, the administration of cyclophosphamide is at a dose of about 500 $mg/m^2/day$, the administration of fludarabine is at a dose of about 25 $mg/m^2/day$, and no IL-2 is administered.

T Cell Dysfunction

In certain embodiments, an effective amount of a Cbl inhibitor may be administered to a patient in need thereof to treat T cell dysfunction.

The daily dosage of a Cbl inhibitor for an individual suffering T cell dysfunction is between 1-5000 mg, 1-2500 mg, 1-2000 mg, 1-1500 mg, 1-1000 mg, 1-750 mg, 1-500 mg, 1-400 mg, 1-300 mg, 1-250 mg, 1-200 mg, 1-100 mg, 1-10 mg, 0.1-10 mg, 0.1-5 mg, or 0.1-1 mg.

An effective amount of a Cbl inhibitor for treatment of T cell dysfunction will, upon administration to a patient in need thereof, result in a concentration of said Cbl inhibitor of between 0.0001-0.5 μM, between 0.001-1 μM, between 0.001-5 μM, between 0.01-10 μM, between 0.1-25 μM, between 0.1-50 μM, between 0.01-100 μM, between 0.1-1000 within the patient.

Patients suffering T cell dysfunctions may be treated with Cbl inhibitors for 1 to 2 days, 1 to 3 days, 1 to 4 days, 1 to 5 days, 1 to 6 days, 1 to 7 days, 1 to 10 days, 1 to 14 days, 1 to 21 days, 1 to 28 days or 1 to 45 days, 1 to 60 days, 2 to 3 days, 2 to 4 days, 2 to 5 days, 2 to 6 days, 2 to 7 days, 2 to 10 days, 2 to 14 days, 2 to 21 days, 2 to 28 days or 2 to 45 days, 2 to 60 days, 4 to 5 days, 4 to 6 days, 4 to 7 days, 4 to 10 days, 4 to 14 days, 4 to 21 days, 4 to 28 days, 4 to 45 days, 4 to 60 days, 7 to 10 days, 7 to 14 days, 7 to 21 days, 7 to 28 days, 7 to 45 days or 7 to 60 days.

Post Infusion Treatment with a Cbl Inhibitor

In certain embodiments, the Cbl inhibitor is administered to an individual after an infusion of immune cells. The length of time between infusion of the immune cells and the administration of the Cbl inhibitor, or vice versa, can be from about 1 minute to about 1 hour, about 5 minutes to about 1 hour, about 10 minutes to about 1 hour, about 15 minutes to about 1 hour, about 20 minutes to about 1 hour, about 30 minutes to about 1 hour, about 45 minutes to about 1 hour, about 1 hour to about 2 hours, about 1 hour to about 4 hours, about 1 hour to about 6 hours, about 1 hour to about 8 hours, about 1 hour to about 12 hours, about 1 hour to about 24 hours, about 2 hours to about 24 hours, about 6 hours to about 7 hours, about 6 hours to about 24 hours, about 8 hours to about 24 hours, about 10 hours to about 24 hours, about 15 hours to about 24 hours, about 20 hours to about 24 hours, about 12 hours to about 48 hours, about 24 hours to about 48 hours, or about 36 hours to about 48 hours.

In some embodiments, the Cbl inhibitor is administered as supportive therapy post infusion. In some embodiments, this period can be from about 1 day to about 7 days, about 2 days to about 7 days, about 3 days to about 7 days, about 4 days to about 7 days, about 5 days to about 7 days, 6 days to about 7 days, 1 day to about 2 weeks, or 1 week to about 3 weeks, 1 week to about 4 weeks, 1 week to about 6 weeks, 1 week to about 9 weeks, 1 week to about 12 weeks, 1 week to about 24 weeks, 1 week to about 48 weeks, 1 week to about 52 weeks, 1 week to about 60 weeks, 1 week to about 100 weeks.

Thus, in some embodiments the therapeutic regimens comprise both adoptive cell therapy and chemotherapy. Some embodiments of the therapeutic regimens described herein comprise drug-enhanced adoptive cell therapy (DE-ACT), drug-enhanced tumor-infiltrating lymphocyte (DE-TIL) therapy, drug enhanced chimeric antigen receptor therapy (DE-CART), or drug enhanced NK-CAR cell therapy.

After the infusion population is administered to an individual, the biological activity of the individual's post-infusion immune cells can be measured by methods known in the art. Parameters to assess include specific binding of modified immune cell or other immune cell to antigen, in vivo (e.g., by imaging) or ex vivo (e.g., by ELISA or flow cytometry). In some embodiments, the ability of modified immune cells to destroy target cells can be measured using any suitable method known in the art, such as cytotoxicity assays described in, for example, Kochenderfer et al., *J Immunotherapy,* 32 (7):689-702 (2009), and Herman et al. *J. Immunological Methods,* 285(1):25-40 (2004). In some embodiments, the biological activity of the individual's post-infusion immune cells also can be measured by assaying expression and/or secretion of certain cytokines, such as IL-2 and IFNγ. In some aspects the biological activity of the post-infusion immune cells is measured by assessing clinical outcome, such as reduction in tumor size or number of tumors.

Conditions Treated

The methods and compositions herein can be used for the treatment of any condition deemed suitable by the person of skill. In certain embodiments, the condition is cancer. In certain embodiments, the condition is a tumor. In certain embodiments, the condition is a hematologic cancer.

In some embodiments of the methods herein, the cancer is a hematologic cancer such as lymphoma, a leukemia, or a myeloma. A hematologic cancer as contemplated herein includes, but is not limited to, one or more leukemias such as B-cell acute lymphoid leukemia ("BALL"), T-cell acute lymphoid leukemia ("TALL"), acute lymphoid leukemia (ALL); one or more chronic leukemias including but not limited to chronic myelogenous leukemia (CML) and chronic lymphocytic leukemia (CLL); additional hematologic cancers or hematologic conditions including, but not limited to B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia," which are a diverse collection of hematological conditions united by ineffective production (or dysplasia) of myeloid blood cells.

In some embodiments of the methods herein, the cancer is a non-hematologic cancer such as a sarcoma, a carcinoma, or a melanoma. A non-hematologic cancer contemplated herein includes, but is not limited to, a neuroblastoma, renal cell carcinoma, colon cancer, colorectal cancer, breast cancer, epithelial squamous cell cancer, melanoma, stomach cancer, brain cancer, lung cancer (e.g., NSCLC), pancreatic cancer, cervical cancer, ovarian cancer, liver cancer, bladder cancer, prostate cancer, testicular cancer, thyroid cancer, uterine cancer, adrenal cancer and head and neck cancer. In certain embodiments, the cancer is melanoma. In certain embodiments, the cancer is cervical cancer. In certain embodiments, the cancer is ovarian cancer. In certain embodiments, the cancer is head and neck squamous cell carcinoma. In certain embodiments, the cancer is non-small cell lung caner.

In some embodiments, the cancer is relapsed or refractory after more than one line of systemic therapy.

Dosage Forms

In some embodiments, the Cbl inhibitors of the disclosure are formulated as pills, capsules, tablets, syrups, ampules, lozenges, powders for oral administration to an individual. In some embodiments, the Cbl inhibitors are formulated for infusion or injection. In some embodiments, the Cbl inhibitors are formulated for use in cell culture in vitro or ex vivo.

In some embodiments of the disclosure the Cbl inhibitor provided herein is a pharmaceutical composition or single unit dosage form. Pharmaceutical compositions and single unit dosage forms provided herein comprise a prophylactically or therapeutically effective amount of one or more Cbl inhibitors. In individuals undergoing in vivo activation prior to providing immune cells, the amount of Cbl inhibitor is an amount sufficient to modulate the activity of the immune cells in vivo compared to an untreated reference sample. The Cbl inhibitor may be administered 1×, 2×, or 3× daily, 4×, or 5× daily.

In certain embodiments, the daily dosage of a Cbl inhibitor for an individual for cell-based immunotherapy is between 1-5000 mg, 1-2500 mg, 1-2000 mg, 1-1500 mg, 1-1000 mg, 1-750 mg, 1-500 mg, 1-400 mg, 1-300 mg, 1-250 mg, 1-200 mg, 1-100 mg, 1-10 mg, 0.1-10 mg, 0.1-5 mg, or 0.1-1 mg.

In certain embodiments, an effective amount of the Cbl inhibitor, upon administration to an individual results in a concentration of said inhibitor of between 0-0.5 μM, between 0-1 μM, between 0-5 μM, between 0-10 μM, between 0-25 μM, between 0-50 μM, between 0-100 μM, or between 0-1000 μM within the affected tissue or tumor or the adjacent or surrounding area during the in vivo activation phase Cells produced by the methods provided herein can be formulated and administered according to standard techniques. Briefly, pharmaceutical compositions may comprise a cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose, dextrans, or mannitol; proteins; polypeptides or amino acids such as glycine; antioxidants; chelating agents such as EDTA or glutathione; adjuvants (e.g., aluminum hydroxide); and preservatives. In certain embodiments, cell compositions are formulated for intravenous administration. Pharmaceutical compositions of the present invention may be administered in a manner appropriate to the disease to be treated (or prevented). The quantity and frequency of administration will be determined by such factors as the condition of the patient, and the type and severity of the patient's disease, and appropriate dosages may be determined by clinical trials.

EXAMPLES

Example 1: Evaluation of a Cbl Inhibitor for Expansion of Human Tumor-Infiltrating Lymphocytes (TIL) Ex Vivo from Tumor Tissue Samples of human ovarian and colon tumors were obtained from the Cooperative Human Tissue Network (CHTN, c/o Vanderbilt University Medical Center, Nashville, Tenn.). Solid tumor specimens were carefully dissected free of surrounding fatty and necrotic areas. The tumors were sliced into 8 $mm^3$ (2×2×2 $mm^3$) fragments under sterile conditions using a scalpel and a scalpel holder.

For tumor cell line generation, multiple fragments were immersed in a mixture of 1 mg/ml Worthington collagenase type 4, 10 μg/ml gentamycin, and 3000 U/ml DNAse in serum-free RPMI 1640 medium. Tumor fragments were initially processed using a Miltenyi gentlemacs octo dissociator and incubated for 30 minutes at 37° C. with gentle agitation. The single-cell slurry was passed through sterile mesh to remove undigested tissue fragments. The resulting slurry of cells was washed and resuspended in media. The cell suspension was layered onto a two-step gradient with 100% Ficoll, and 75% Ficoll and 25% media. After centrifugation at 2000 rpm for 20 minutes, the interfaces were collected. The upper, tumor-cell-enriched fraction was plated at approximately $1\times10^6$ tumor cells in a T75 tissue culture flask (VWR) in RPMI medium containing 20% Fetal Bovine Serum (FBS).

For TIL generation, single 8 $mm^3$ tumor fragments were added to each well of a 24-well plate containing 2 mL RPMI medium containing 25 mM HEPES, 10% heat inactivated human AB serum, 100 U/mL penicillin, 100 μg/ml streptomycin, 2 mM L-glutamine, 10 μg/ml gentamycin and 0.25 μg/ml Fungizone (Complete Medium; CM) with either 6000 IU/mL IL-2 in the presence or absence of 0.1-10 μM of a Cbl inhibitor, or with 0.1-10 μM of the Cbl inhibitor alone. The plates were placed in a humidified 37° C. incubator with 5% $CO_2$. Half of the medium was replaced every two days after culture initiation. As wells became confluent, the contents were mixed vigorously, split into two daughter wells, and filled to 2 mL per well with RPMI medium with either 6000 IU/mL IL-2 in the presence or absence of 0.1-10 μM of the Cbl inhibitor, or with 0.1-10 μM of the Cbl inhibitor alone. Subsequently, half the media was replaced thrice weekly, cultures were split to maintain a cell density of $1\times10^6$ cells/mL. The TIL were pooled and counted at days 17 and 28, and immunophenotyped at day 28 by flow cytometry by measuring expression of lineage (CD4, CD8), differentiation and other T cell markers including ICOS, CD45RA, CD45RO, CD95, CCR7, CD62L, CD3ε, CD8α, CD14, CD19, CD20, CD11c, TCF1, PD-1, TIM3, LAG3, CD27, CD28, CD127, PD-1, CD122, CD132, KLRG-1, HLA, HLA-DR, CD33, CD61, Cd235, TCRγ, TCRδ, CD38, CD69, CD11a, CD58, CD99, CD103, CCR4, CCR5, CCR6, CCR9, CCR10, CXCR3, CXCR4, CLA, CD161, IL-18Ra, c-Kit, and CD130. Mitochondrial markers including, Mitotracker, Mitoprobe, and 2-NBDG may also be used to assess differentiation and/or activation of cells. The initial TIL generation step may be shortened from 28 days to between about 7-11 days with similar results.

Figure 1B:
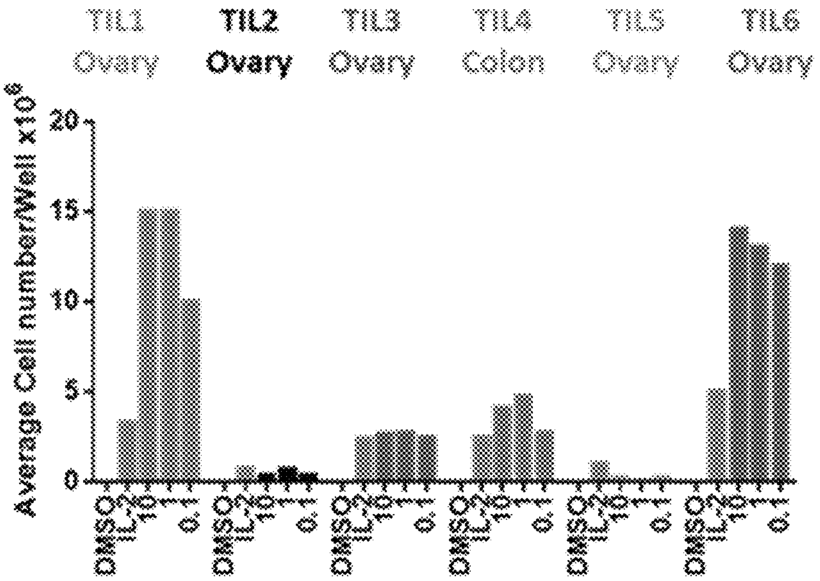
Figure 5A:
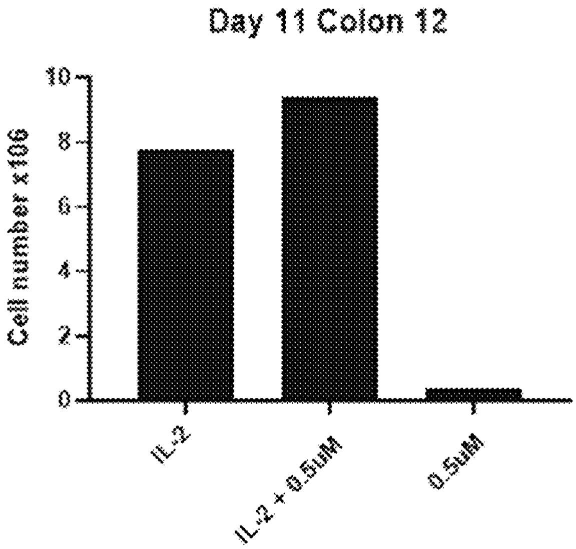
FIGS. 5A and 5B provide results of TIL from colon tumor-derived (FIG. 5A) and ovarian tumor-derived (FIG. 5B) TIL cultured in the presence of IL-2, Cbl inhibitor, and the combination thereof.
Figure 5B:
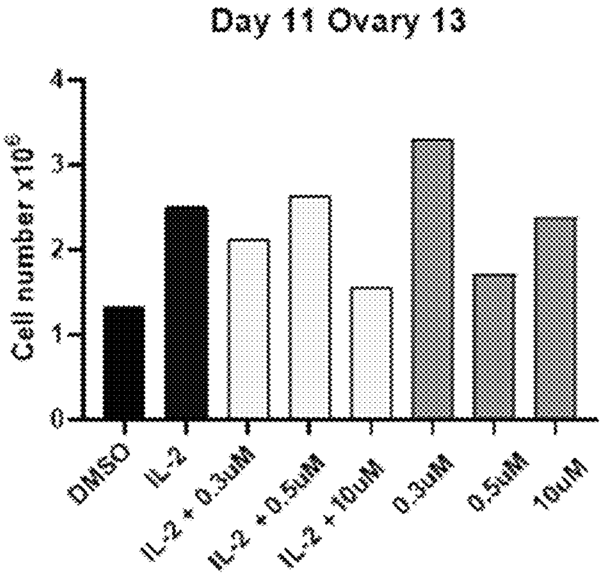
Figure 6:
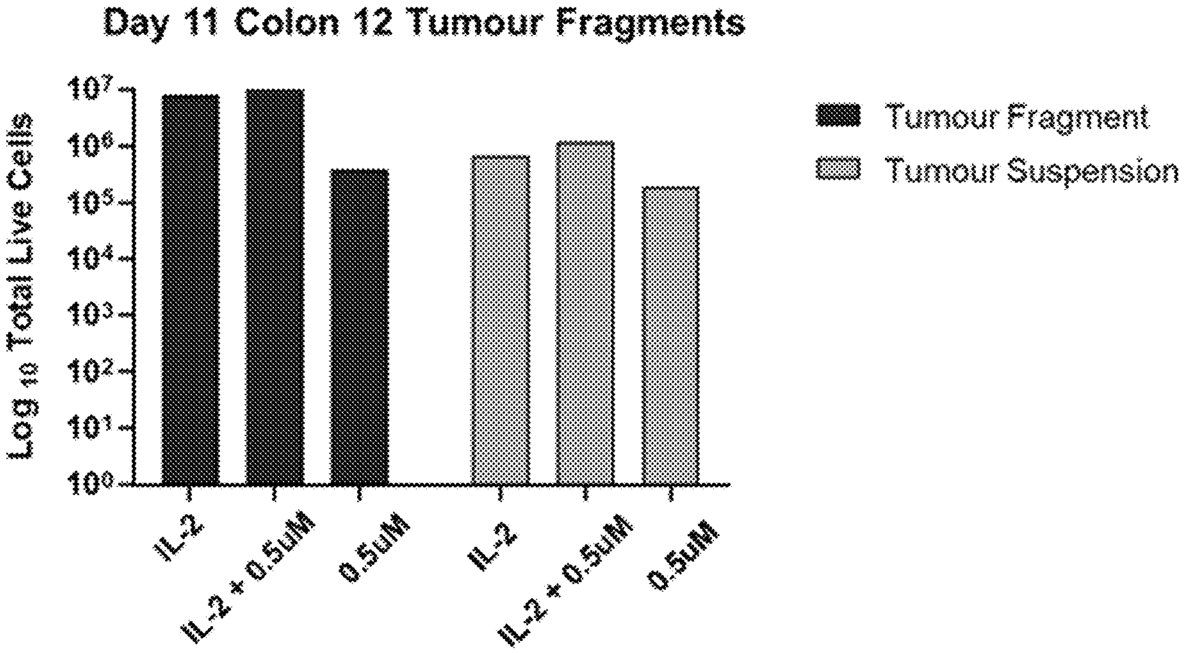
FIG. 6 provides results for studies to determine optimal starting materials for TIL cultures. In a study using tumor fragments vs. tumor cell suspensions from a colon tumor, cultures grown from the tumor fragments for 11 days showed approximately 10-fold higher expansion than cultures using a tumor cell suspension as the starting material for the TIL culture.

The data in Figures and Tables 2-7 are with compound 103. FIG. 1 shows the average number of cells/well and the magnitude of TIL expansion variability between tumor samples. For this reason, the total cell numbers are shown in Table 2 as a percentage of the IL-2 alone condition. FIG. 1A shows the average number of cells with IL-2 alone or Cbl inhibitor alone. FIG. 1B shows the average number of cells with IL-2 alone or IL-2 in combination with 0.1, 1, or 10 μM of Cbl inhibitor. FIGS. 4A-4D show the average numbers of cells with IL-2 alone; with 0.1, 1, or 10 μM of Cbl inhibitor; or IL-2 in combination with 0.1, 1, or 10 μM of Cbl inhibitor with ovary TIL and colon TIL. FIG. 5A shows the average numbers of cells with IL-2 alone; with 0.5 μM of Cbl inhibitor; or IL-2 in combination with 0.50 μM of Cbl inhibitor with colon TIL. FIG. 5B shows the average numbers of cells with IL-2 alone; with 0.3, 0.5 or 10 μM of Cbl inhibitor; or IL-2 in combination with 0.3, 0.5 or 10 μM of Cbl inhibitor with colon TIL. FIG. 6 shows the average numbers of cells with IL-2 alone; with 0.5 μM of Cbl inhibitor; or IL-2 in combination with 0.50 μM of Cbl inhibitor with colon TIL from tumor fragments or from tumor suspensions. Remarkably, culturing TIL in the presence of the Cbl inhibitor, even in the absence of IL-2, resulted in considerable expansion of TIL. This is surprising given that tumor samples cultured in the absence of both the Cbl inhibitor and IL-2 did not yield any viable cells. Additionally, culturing TIL in the presence of both IL-2 and the Cbl inhibitor resulted in the production of substantially more TIL from two of the four tumor samples (TIL1 and TIL4), than did culturing TIL in the presence of either IL-2 or the Cbl inhibitor alone. Thus, Cbl inhibitors support cell viability in the absence of IL 2 and enhance the effects of IL-2 in some tumor samples.

TABLE 2

Expansion of TIL from Human Tumor Samples

| Condition^ | TIL1 % (ovary) | TIL2 % (ovary) | TIL3 % (ovary) | TIL4 % (colon) | TIL5 % (ovary) | TIL6 % (ovary) |
|---|---|---|---|---|---|---|
| IL-2 alone | 100 | 100 | 100 | 100 | 100 | 100 |
| 0.1 μM Cbl-i | 90 | 30 | 30 | 45 | 50 | 93 |
| 1.0 μM Cbl-i | 75 | 26 | 43 | 58 | 70 | 87 |
| 10 μM Cbl-i | 60 | 22 | 16 | 54 | 90 | 80 |
| IL-2 + 0.1 μM Cbl-i | 300 | 49 | 103 | 113 | 20 | 280 |
| IL-2 + 1.0 μM Cbl-i | 450 | 86 | 114 | 197 | 10 | 260 |
| IL-2 + 10 μM Cbl-i | 450 | 49 | 110 | 170 | 20 | 240 |

^Percentage of total cell number relative to IL-2 alone on day 17.

Rapid Expansion Protocol

Rapid Expansion Protocol (REP) used OKT3 (anti-CD3) antibody (Thermo Fisher Scientific) and IL-2 in the presence of irradiated, allogeneic feeder cells (Astarte Biologics) at a 200:1 ratio of feeder cells to responding TIL cells. PBMC, OKT3 antibody (30 ng/mL), complete medium ("CM"), AIM V media (GIBCO/BRL), and TIL effector cells were combined, mixed, and aliquoted to a 75 $cm^2$ tissue culture flask. Flasks were incubated upright at 37° C. in 5% $CO_2$. IL-2 (6000 IU/mL) and/or Cbl inhibitor (0.1, 1, 10 μM) were added on day 2. On day 5, culture supernatant was removed by aspiration and media was replaced with a 1:1 mixture of CM/AIM V containing 6000 IU/mL IL-2 and/or Cbl inhibitor. On day 6, and every day thereafter, cell concentration was determined, and cells were split into additional flasks with additional medium containing 6000 CU/mL IL-2/Cbl inhibitor as needed to maintain cell densities around $1\times10^6$ cells/mL. About 14 days after initiation of the REP, cells were harvested and cryopreserved for future experimental analysis.

Only TIL that expanded during the pre-REP protocol were further expanded in the REP protocol: TIL1, TIL3, TIL4 & TIL6. The magnitude of TIL expansion during the REP varied between the tumor samples. For this reason, the total cell numbers are shown in Table 3 as a percentage of the IL-2 alone condition during the REP expansion protocol.

TABLE 3

Expansion of TIL from Human Tumor Samples (REP)

| Condition^ | TIL1 % (ovary) | TIL3 % (ovary) | TIL4 % (colon) | TIL6 % (ovary) |
|---|---|---|---|---|
| IL-2 alone | 100 | 100 | 100 | 100 |
| 0.1 μM Cbl-i | 40 | 127 | 80 | 51 |
| 1.0 μM Cbl-i | 42 | 150 | 80 | 63 |
| 10 μM Cbl-i | 32 | 107 | 107 | 49 |
| IL-2 + 0.1 μM Cbl-i | 50 | 193 | 167 | 206 |
| IL-2 + 1.0 μM Cbl-i | 52 | 207 | 194 | 180 |
| IL-2 + 10 μM Cbl-i | 49 | 197 | 240 | 168 |

^Percentage of total cell number relative to IL-2 alone on day 42 (Pre-REP and REP).

Figure 7:
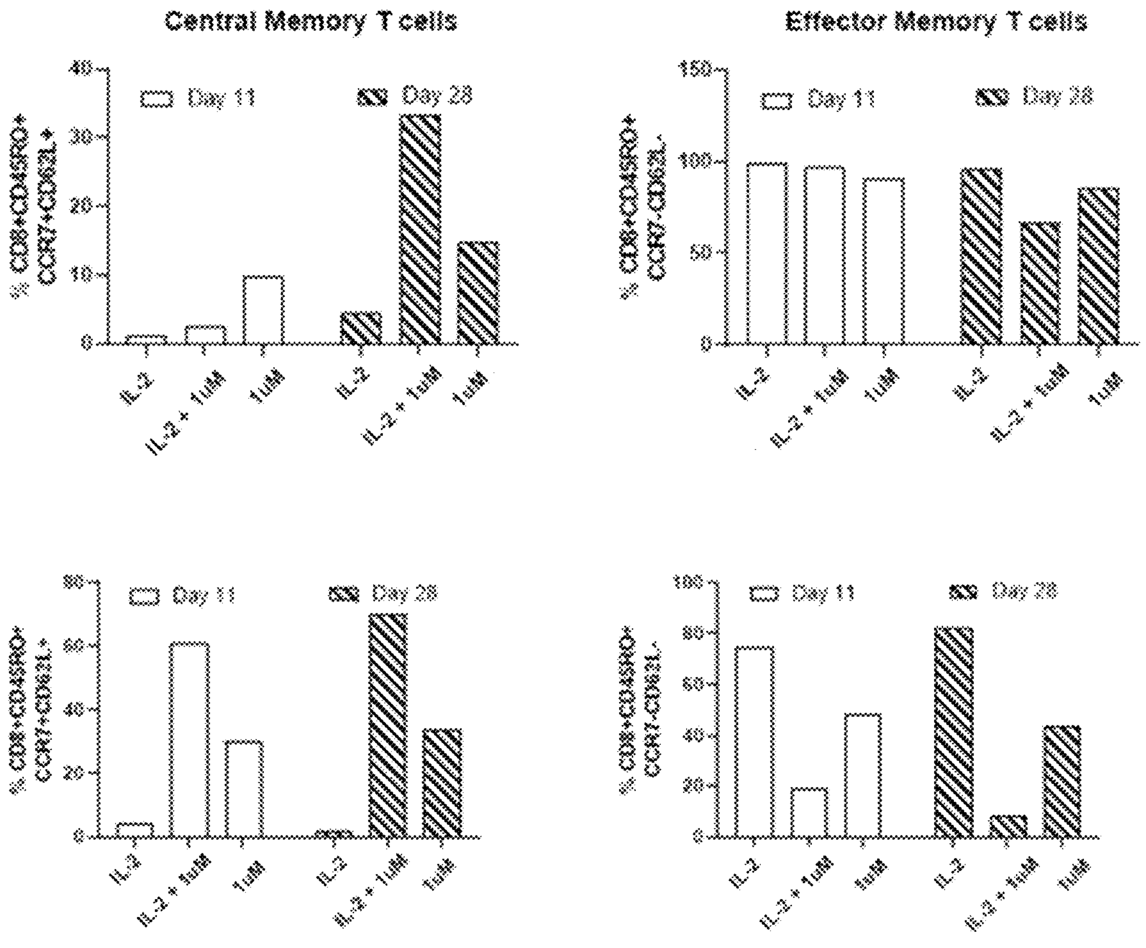
FIG. 7 provides day 11 and day 28 results for % of CD4+ and CD8+ cells showing a central memory phenotype (CD45RO+) after culture of TIL derived from a human colon tumor.

T lymphocytes were defined based on lineage and differentiation marker expression according to the developmental model (Restifo, Blood, 124:476-477, 2014), as shown in Table 4. Interestingly, human TIL expanded ex vivo in the presence of the Cbl inhibitor have a $T_{CM}$ (CD45RO+, CD95+, CCR7+, CD62L+) or $T_{EM}$ (CD45RO+, CD95+, CCR7−, CD62L−) phenotype, as shown in Table 5. Additionally, the Cbl inhibitor was found to selectively expand CD8+ T lymphocytes from a malignant ovarian tumor sample, as shown in FIG. 7. This is remarkable given that essentially equivalent numbers of CD4+ and CD8+ T lymphocytes were produced when TIL were cultured ex vivo with IL-2 alone. Monocytes (CD14+), B cells (CD20+) and NK cells (CD56+) accounted for <10% of the total number of cells.

TABLE 4

Marker Expression by T Lymphocytes

| Type | CD45RA/RO | CD95 | CCR7 | CD62L |
|---|---|---|---|---|
| $T_N$ (naïve) | RA+ | − | + | + |
| $T_{SCM}$ (stem cell memory) | RA+ | + | + | + |
| $T_{CM}$ (central memory) | RO+ | + | + | + |
| $T_{EM}$ (effector memory) | RO+ | + | − | − |
| $T_{EFF}$ (effector) | RA+ | + | − | − |

TABLE 5

Central and Effector Memory T Cells in TIL1 Population^

| Condition | CD8 $T_{CM}$ CD62L+ CCR7+ | CD8 $T_{EM}$ CD62L− CCR7− | CD4 $T_{CM}$ CD62L+ CCR7+ | CD4 $T_{EM}$ CD62L− CCR7− |
|---|---|---|---|---|
| DMSO | 0 | 0 | 0 | 0 |
| IL-2 alone | 4.2 | 48.7 | 1.8 | 48.9 |
| 0.1 μM Cbl-i | 19.5 | 37.2 | 2.8 | 67.2 |
| 1.0 μM Cbl-i | 20.2 | 15.6 | 8.0 | 24.2 |
| 10 μM Cbl-i | 29.7 | 13.2 | 15.8 | 66.7 |
| IL-2 + 0.1 μM Cbl-i | 20.3 | 35.5 | 12.1 | 49.3 |
| IL-2 + 1.0 μM Cbl-i | 16.5 | 43.3 | 15.2 | 57.3 |
| IL-2 + 10 μM Cbl-i | 20.5 | 35.4 | 0 | 55.8 |

^Percentage of total TIL cell number on day 28.

^T cells genetically engineered to express chimeric antigen receptors (CARs) may be similarly expanded. Briefly, T cells are isolated from a patient's whole blood, buffy coats or leukopaks and expanded as described above. Lentiviral transduction introduces the CAR to the T cells. The T cells are assessed for the total number of cells generated as well as their phenotype by flow cytometric analysis determining memory, effector, exhaustion and stemness (e.g., CD95, TCF7, CD62L, CCR7, CD45RO and CD45RA, TOX, PD-1, TIM3, LAG3) and transduction efficiency. The resulting CAR T cells are expanded and assessed for their ability to produce cytokines (e.g., IFNγ) following reactivation by specific antigen for the CAR or a generic T cell activation method (e.g., anti-CD3/CD28).

Example 2: Evaluation of a Cbl Inhibitor for Expansion of Antigen Specific Human T Cells from Peripheral Blood Mononuclear Cells Ex vivo expansion of T cells from peripheral blood mononuclear cells in the presence Cbl inhibitor was evaluated.

CMV pp65 (495-503) reactive T cells were expanded by thawing CMV seropositive donors (Conversant) and 2×10 6 cells/ml were resuspended in RPMI medium (Gibco) supplemented with 1% GlutaMax (Gibco), 1% non-essential amino acids (NEAA), penicillin/streptomycin (Gibco), 10% heat inactivated human AB serum (Corning), 1 μg/ml CMV pp65 (495-503) (Anaspec), 2 ng/mL IL-2 (R&D), and/or Cbl inhibitor (01, 1, 10 μM). PBMCs were cultured for eight days with IL-2 and/or Cbl inhibitor and replenished at day three and day five. At day eight, cells were harvested, and re-plated in low dose IL-2 (100 U/ml) and/or Cbl inhibitor at 2 million/ml in complete RPMI media for two days. At day eleven, cells were pooled and counted, and immunophenotyped at day 11 by flow cytometry by measuring expression of lineage (CD4, CD8) and differentiation (including CD45RA, CD45RO, CD95, CCR7, CD62L, TCF1, PD-1, TIM3, LAG3) markers.

The magnitude of expansion varied between samples. Remarkably, culturing T cells in the presence of the Cbl inhibitor, even in the absence of IL-2, resulted in considerable expansion of T cells.

TABLE 6

Expansion of T cells from Human Peripheral Mononuclear Cells.

| Condition^ | Donor 1% | Donor 2% | Donor 3% |
|---|---|---|---|
| IL-2 alone | 100 | 100 | 100 |
| 0.1 μM Cbl-i | 12 | 70 | 175 |
| 1.0 μM Cbl-i | 12 | 95 | 75 |
| 10 μM Cbl-i | 44 | 45 | 38 |
| IL-2 + 0.1 μM Cbl-i | 614 | 2059 | 3622 |
| IL-2 + 1.0 μM Cbl-i | 1007 | 170 | 2145 |
| IL-2 + 10 μM Cbl-i | 898 | 2161 | 1151 |

^Percentage of total cell number relative to IL-2 alone on day 11.

Figure 2A:
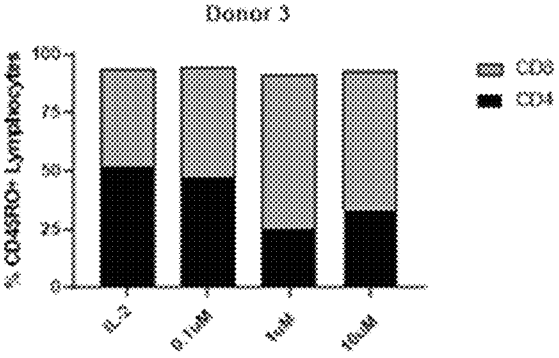
FIGS. 2A and 2B provide results of flow cytometry studies performed on TIL after expansion for 11 days in the presence of 0.1 μM, 1.0 μM, and 10 μM Cbl inhibitor in the absence (FIG. 2A) and presence (FIG. 2B) of IL-2.
Figure 2B:
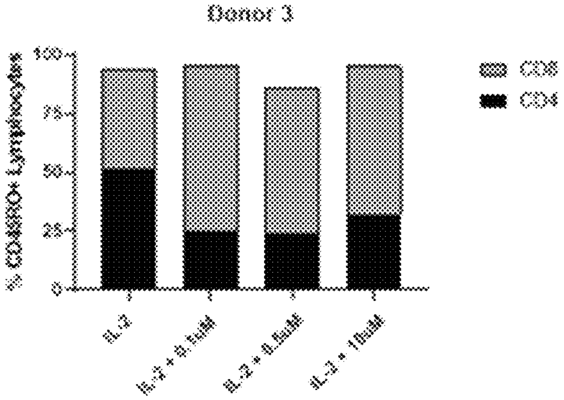

T lymphocytes were defined based on lineage and differentiation marker expression according to the developmental model (Restifo, Blood, 124:476-477, 2014), as shown in Table 4. Interestingly, human T cells expanded ex vivo in the presence of the Cbl inhibitor have a $T_{SCM}$ (CD45RA+, CD95+, CCR7+, CD62L+), $T_{CM}$ (CD45RO+, CD95+, CCR7+, CD62L+) or $T_{EM}$ (CD45RO+, CD95+, CCR7−, CD62L−) phenotype, as shown in Table 7. Additionally, the Cbl inhibitor was found to selectively expand CD8+ T lymphocytes from donor PBMCs, as shown in FIGS. 2A and 2B. FIG. 2A shows the selective expansion of T cells from a PBMC sample in the presence of IL-2, 0.1 μM Cbl inhibitor, 1 μM Cbl inhibitor, and 10 μM Cbl inhibitor in the absence (FIG. 2A) and presence (FIG. 2B) of IL-2. Cells cultured in the presence of IL-2 in combination with 0.1 or 0.5 μM of Cbl inhibitor showed the highest percentage of CD8+ cells in culture. Additionally, cells cultured in 1 μM Cbl inhibitor alone showed higher percentages of CD8+ cells than those cultured in IL-2 alone.

TABLE 7

Central and Effector Memory T Cells in donor PBMC

| Condition | CD8 $Ts_{CM}$ | CD8 $T_{CM}$ | CD8 $T_{EM}$ | CD4 $Ts_{CM}$ | CD4 $T_{CM}$ | CD4 $T_{EM}$ |
|---|---|---|---|---|---|---|
| DMSO | 0 | 0 | 0 | 0 | 0 | 0 |
| IL-2 alone | 39.9 | 25.4 | 11 | 16.9 | 43.2 | 24.9 |
| 0.1 μM Cbl-i | 17.1 | 50.7 | 14.2 | 12 | 53.1 | 23.9 |
| 1.0 μM Cbl-i | 7.29 | 61.1 | 12.9 | 7.27 | 55.3 | 19.3 |
| 10 μM Cbl-i | 10.8 | 34.2 | 9.23 | 1.37 | 47.3 | 23.3 |
| IL-2 + 0.1 μM Cbl-i | 4.2 | 47.8 | 18.3 | 8.53 | 13.9 | 29.7 |
| IL-2 + 1.0 μM Cbl-i | 0.23 | 37.8 | 41.4 | 1.98 | 16.8 | 28.4 |
| IL-2 + 10 μM Cbl-i | 9.36 | 49 | 10.6 | 2.69 | 24.3 | 25.8 |

Percentage of total cell number on day 11.

Figure 3A:
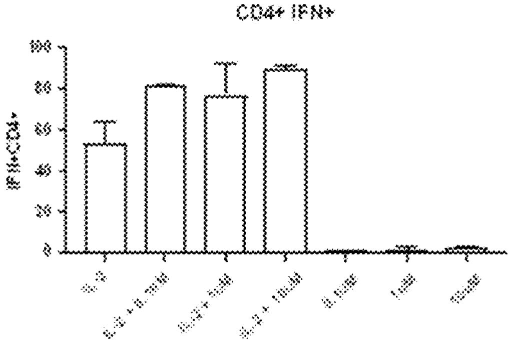
FIGS. 3A and 3B show the levels of CD4+/IFNγ (FIG. 3A) and CD8+/IFNγ (FIG. 3B) TIL after 11 days expansion the presence of 0.1 μM, 1.0 μM, and 10 μM Cbl inhibitor in the absence and presence of IL-2.
Figure 3B:
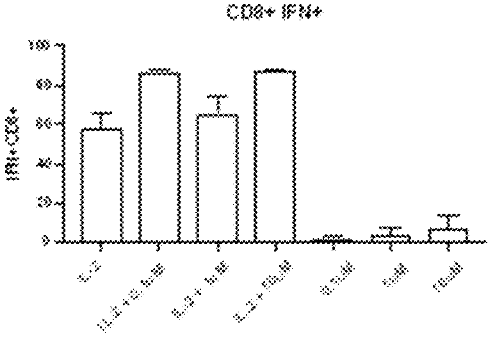
Figure 4A:
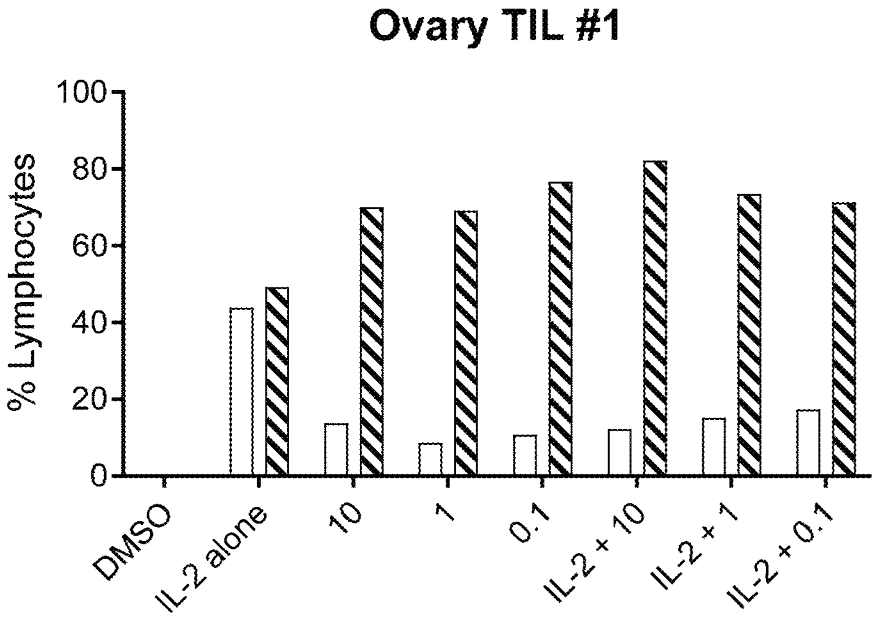
FIGS. 4A-4D show the % lymphocytes grown from tumors from different patients. TIL derived from ovarian tumors were grown in the presence of DMSO (control), IL-2, and 10 μM, 1 μM, and 0.1 μM Cbl inhibitor alone, and in combination with IL-2.
Figure 4B:
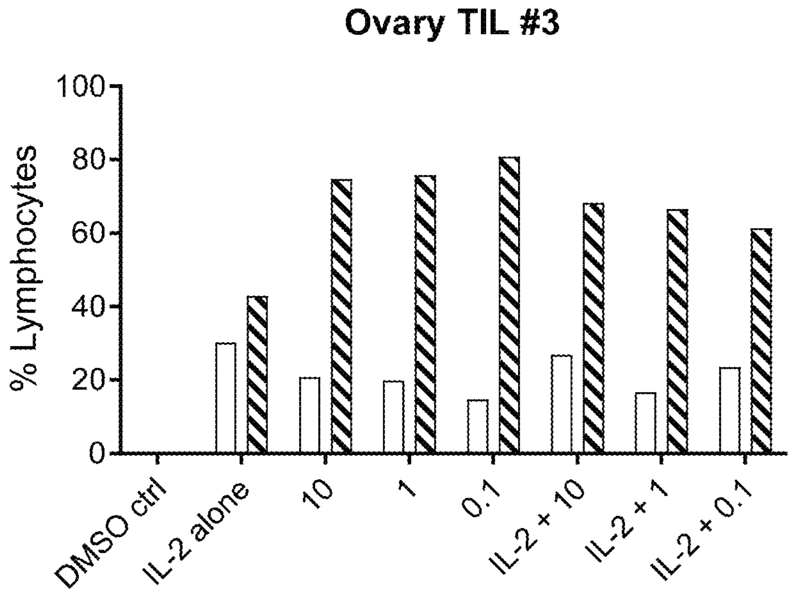
Figure 4C:
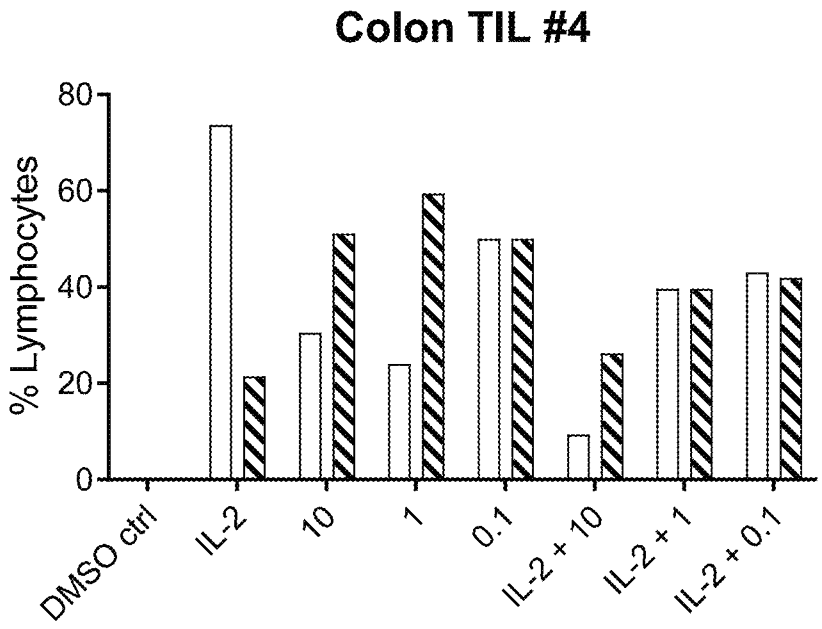
Figure 4D:
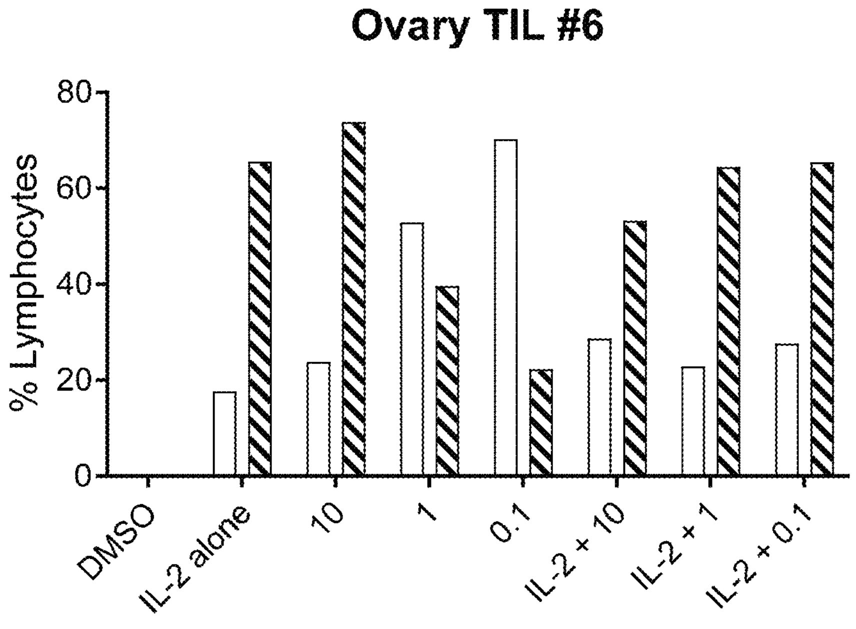

T cell activity was determined by analysis of cytokine secretion. To investigate whether these expanded T cells are capable of responding to extracellular stimulation, T cells were stimulated with 25 ng/mL phorbol myristate acetate (PMA) and 0.5 μM ionomycin. After 90 min of stimulation, monensin, 1:50, (GolgiStop, BD Biosciences) was added. After 6 h, cells were stained for surface expression of CD4+, CD8+, CD45RA+, CD95+, CCR7+, CD62L+, and subsequently, fixed, permeabilized and stained for intracellular cytokine, IFN-7. After 6 hr, we observed a clear increase in accumulated intracellular IFN-γ, an important effector of the anti-tumor response when T cells had been expanded with IL-2 and Cbl inhibitor. We found that approximately 50% of CD4/8+ T cells were positive for IFN-γ expression in IL-2 expanded T cells, and greater than 85% IL-2 and Cbl inhibitor expanded CD4/8+ T cells were capable of producing IFN-7. FIG. 3A shows that T cells cultured in the presence of Cbl inhibitor and IL-2 showed higher levels of both CD4/CD8+ and IFNγ+ cells than those cultured in the presence of IL-2 alone or the Cbl inhibitor alone. The expression of both CD4/8+ and IFNγ+ cells suggest that IL-2 and Cbl inhibitor expanded T cells contain the functional potential to elicit an anti-tumor response.

Example 3: Evaluation of a Cbl Inhibitor for Expansion of Human Tumor-Infiltrating Lymphocytes (TIL) Ex Vivo from Tumor Tissue Using Gas Permeable Flasks FIG. 6 provides results for studies to determine optimal starting materials for TIL cultures. In a study using tumor fragments vs. tumor cell suspensions from a colon tumor, cultures grown from the tumor fragments for 11 days showed approximately 10-fold higher expansion than cultures using a tumor cell suspension as the starting material for the TIL culture.

Cultures were initiated in gas permeable flasks with a 40 mL capacity and a 10 $cm^2$ gas permeable silicon bottom (GREX™6M; Wilson Wolf Manufacturing, MN), each flask was loaded with 5 tumor fragments in 40 mL of media with IL-2 and or 1 uM Cbl inhibitor added either alone or in combination at Day 0 (D0) or Day 3 (D3). The G-REX™ wells were incubated in a humidified incubator at 37C in 5% $CO_2$ for 7 to 28 days.

Figure 8:
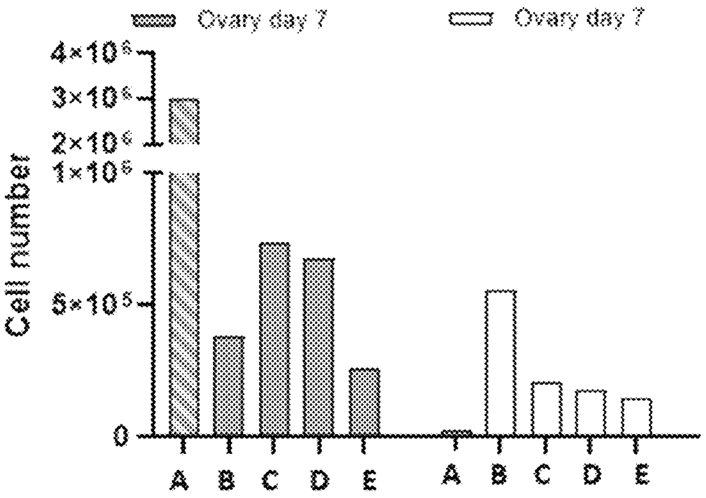
FIG. 8 provides day 7 results using a gas permeable flask with a gas permeable silicon bottom for cell expansions from 2 different ovary tumor samples where the addition of IL-2 or Cbl inhibitor at day 0 or day 3 were compared. “A” is the addition of IL-2 alone on day 0. “B” is the addition of IL-2 and 1 μM Cbl inhibitor on day 0. “C” is the addition of IL-2 on day 0 and the addition of 1 μM of Cbl inhibitor on day 3. “D” is the addition of IL-2 on day 3 and the addition of Cbl inhibitor on day 3. “E” is the addition of Cbl inhibitor on day 0.

FIG. 8 provides day 7 results using a gas permeable flask with a gas permeable silicon bottom for cell expansions from 2 different ovary tumor samples where the addition of IL-2 or Cbl inhibitor at day 0 or day 3 were compared. "A" is the addition of IL-2 alone on day 0. "B" is the addition of IL-2 and 1 μM Cbl inhibitor on day 0. "C" is the addition of IL-2 on day 0 and the addition of 1 μM of Cbl inhibitor on day 3. "D" is the addition of IL-2 on day 3 and the addition of Cbl inhibitor on day 3. "E" is the addition of Cbl inhibitor on day 0.

Example 4: Evaluation of a Cbl Inhibitor Effects on Ex Vivo Expansion of Antigen Specific T Cells Transferred In Vivo to Determine Efficacy and Mechanism of Action in a Tumor Model Culture of tumor specific T cells ex vivo in the presence of a Cbl Inhibitor can confer a superior anti-tumor effect as compared to standard culture conditions using IL-2 alone. In this example, it demonstrated that even a short, 3-day ex vivo exposure of T cells to compound 103, either alone or in combination with IL-2, conferred a lasting anti-tumor phenotype for over a month upon transfer of the cells into a tumor-bearing animal as compared to controls.

Antigen specific T cells from transgenic mice can be leveraged as a model for CAR T or TIL expansion ex vivo with a Cbl inhibitor. The OT-1 transgenic animals, that are commercially available, have CD8 T cells that recognize OVA peptide aa 257-264 when presented by the MHC I molecule. CD8+ T cells from OT-1 mice were isolated from a single cell suspension of splenocytes by negative selection (StemCell Technologies cat #19853 EasySep™ Mouse CD8+ T Cell Isolation Kit). Cell were then resuspended in complete media (RPMI1640, 10% heat inactivated FBS, 1× Penicillin/Streptomycin, 1× Glutamine and β-mercaptoethanol) at concentration of $0.5\times10^6$ per mL. Six well tissue culture plates (Falcon) were coated with 2 ug/mL of anti-mouse CD3 (Bio Xcell Cat #BE0001-1-R100 mg InVivoMAb anti-mouse CD3ε Clone: 145-2C11) for >3 hrs at 37° C. and washed with PBS (MediaTech) prior to cell addition. For ex vivo expansion, $1.5\times10^6$ cells/well were cultured in the presence of IL-2 (300 IU) (R&D Systems), Cbl inhibitor (1 μM) or a combination of IL-2 and Cbl inhibitor. Cbl inhibitors have been shown to interact with mouse CBLB and demonstrate a similar profile of enhanced proliferation and cytokine secretion. Following three days of OT-1 T cell activation and expansion the cells were collected, counted and immunophenotyped by flow cytometry by measuring expression of differentiation and additional T cell makers including: CD3, CD4, CD8, CD45, CD25, Granzyme B, CD107a, CD127, PD-1, TIM3, LAG3, KLRG-1, ICOS, TCF1, Ki67, T-bet and FOXP3. A trend of increased effector function in response to the inclusion of a CBL inhibitor during expansion was found as measured enhanced granzyme and T-bet.

Dead cells were removed (Miltenyi Biotec Cat #130-090-101) prior to transfer in vivo to monitor their trafficking and function in an EG.7 lymphoma model, which expresses the OVA antigen. Approximately five million cells per mouse were transferred to mice having an average tumor burden of about 70 $mm^3$. Following in vivo transfer of the OT-1 cells, antitumor response was monitored over time and the quality and quantity of immune response were assessed at various time points. The OT-1 cells from blood and spleen demonstrated higher frequency in total CD8+ T cells and CD45+ cells and in vivo persistence when they were analyzed 4 and 9 days post transfer. In addition, OT-1 cells expanded with Cbl inhibitor showed a greater percentage of cells that expressed stem markers $TCF1^+$, $PD\text{-}1^+$, and $TIM\text{-}3^+$.

Figure 9:
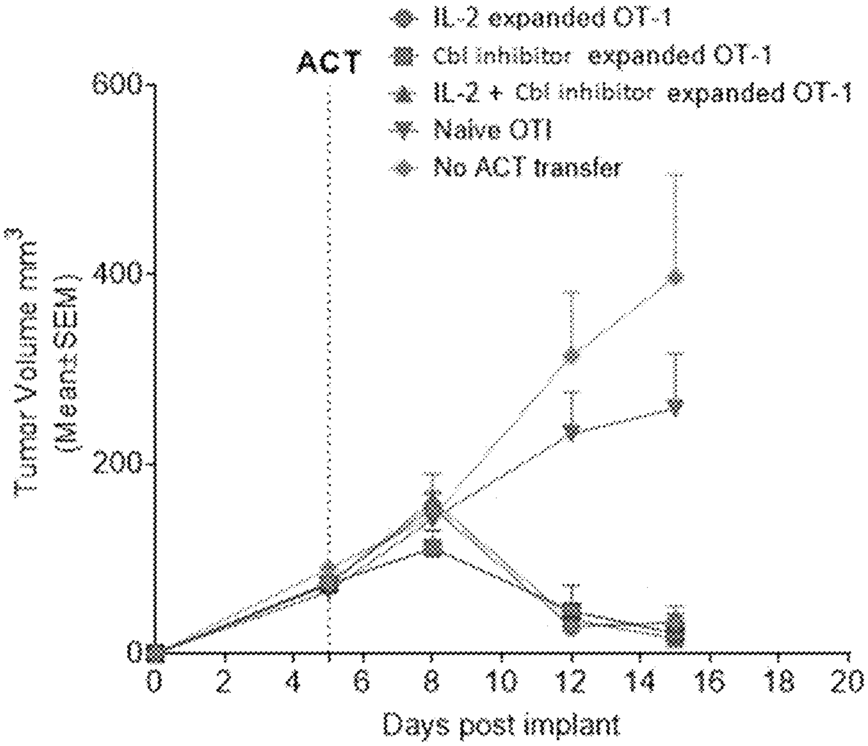
FIG. 9 provides results showing that OT-1 cells expanded with Cbl inhibitor are potent effectors capable of rejecting established tumors in mice subcutaneously implanted with E.G7-OVA cells in one flank.

FIG. 9 provides results showing that OT-1 cells expanded with Cbl inhibitor are potent effectors capable of rejecting established tumors in mice subcutaneously implanted with E.G7-OVA cells.

Figure 10:
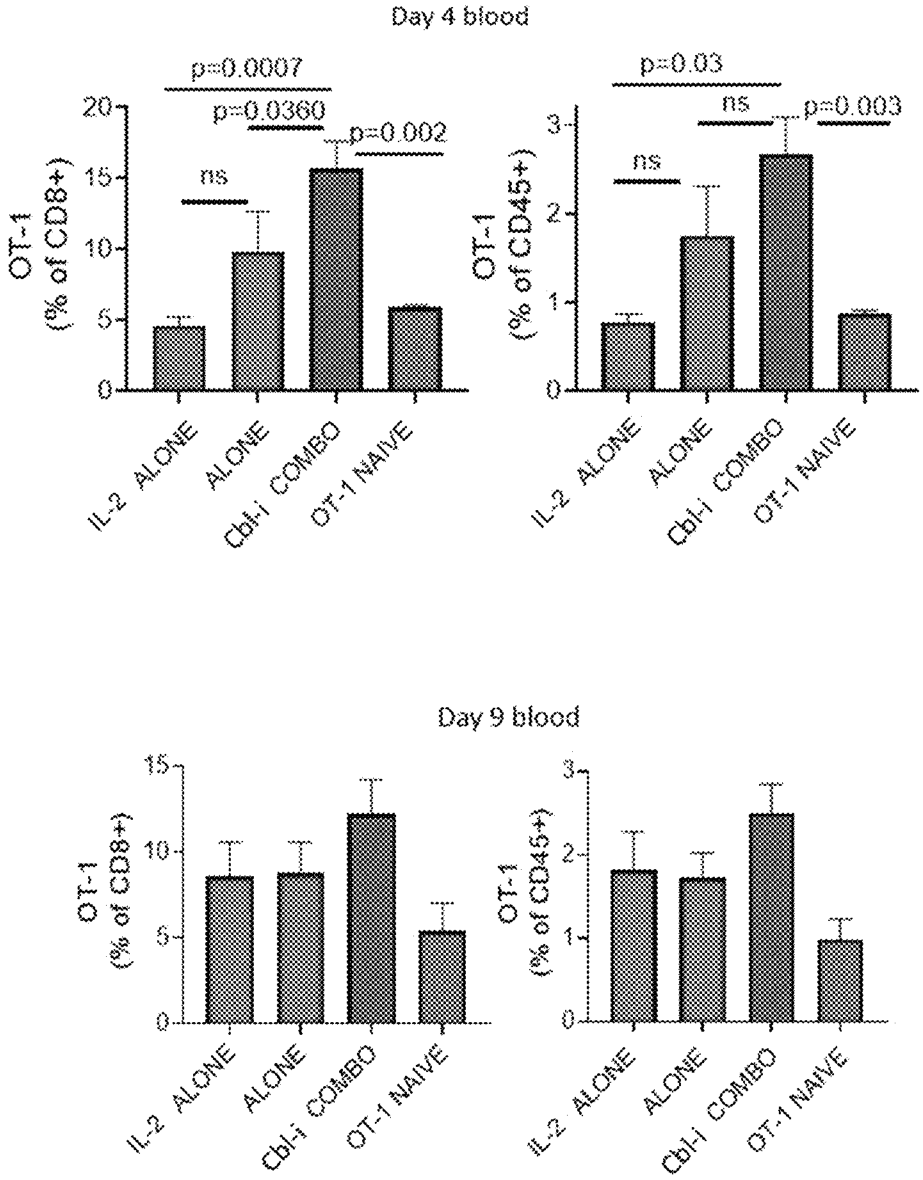
FIG. 10. Provides results showing that OT-1 cells expanded with Cbl inhibitor demonstrate higher frequency in total CD8+ T cells and CD45+ cells and in vivo persistence in the blood. The OT-1 cells in blood were assessed 4 or 9 days after transfer. Similar data were obtained when OT-1 cells obtained from spleen were analyzed.

FIG. 10. Provides results showing that OT-1 cells expanded with Cbl inhibitor demonstrate higher frequency in total CD8+ T cells and CD45+ cells and in vivo persistence in the blood. The OT-1 cells in blood were assessed 4 or 9 days after transfer. Similar data were obtained when OT-1 cells obtained from spleen were analyzed.

Example 5: Evaluation of Cbl Inhibitor-Expanded Tumor Antigen Specific T Cells This example evaluates the therapeutic efficacy of cells expanded in the presence of a Cbl-b inhibitor.

Briefly, tumor antigen specific CD8+ T cells expressing transgenic T cell receptor specific for ovalbumin (OT-1) were expanded in vitro for three days in the presence of plate-bound CD3 plus 1) Cbl inhibitor at 1 μM, 2) IL-2 at 300 IU, and 3) Cbl inhibitor and IL-2 in combination. The expanded OT-1 cells were characterized by FACS analysis and transferred into E.G7-OVA mice, which bear ovalbumin (OVA) expressing tumors. Following in vivo transfer of expanded OT-1 cells, antitumor response was monitored over time and the quality and quantity of immune response was assessed at various time points. Analysis included FACS analysis on blood, tumor, and spleen samples. Analysis also included re-stimulation of splenocytes with OVA Class I peptide to evaluate the multifunctionality of the antigen-specific effector T cells.

On Day 0, E.G7-OVA cells were implanted into each mouse. On Day 5, approximately $5\times10^6$ in vitro expanded OT-1 cells were injected into the tail of each mouse. On Day 9, blood was analyzed by FACS. On Day 14, blood, tumor and spleen samples were analyzed by FACS. On Day 27, blood was analyzed by FACS. Tumor volume was measured approximately every five days through about 50 days post implant.

Figure 11A:
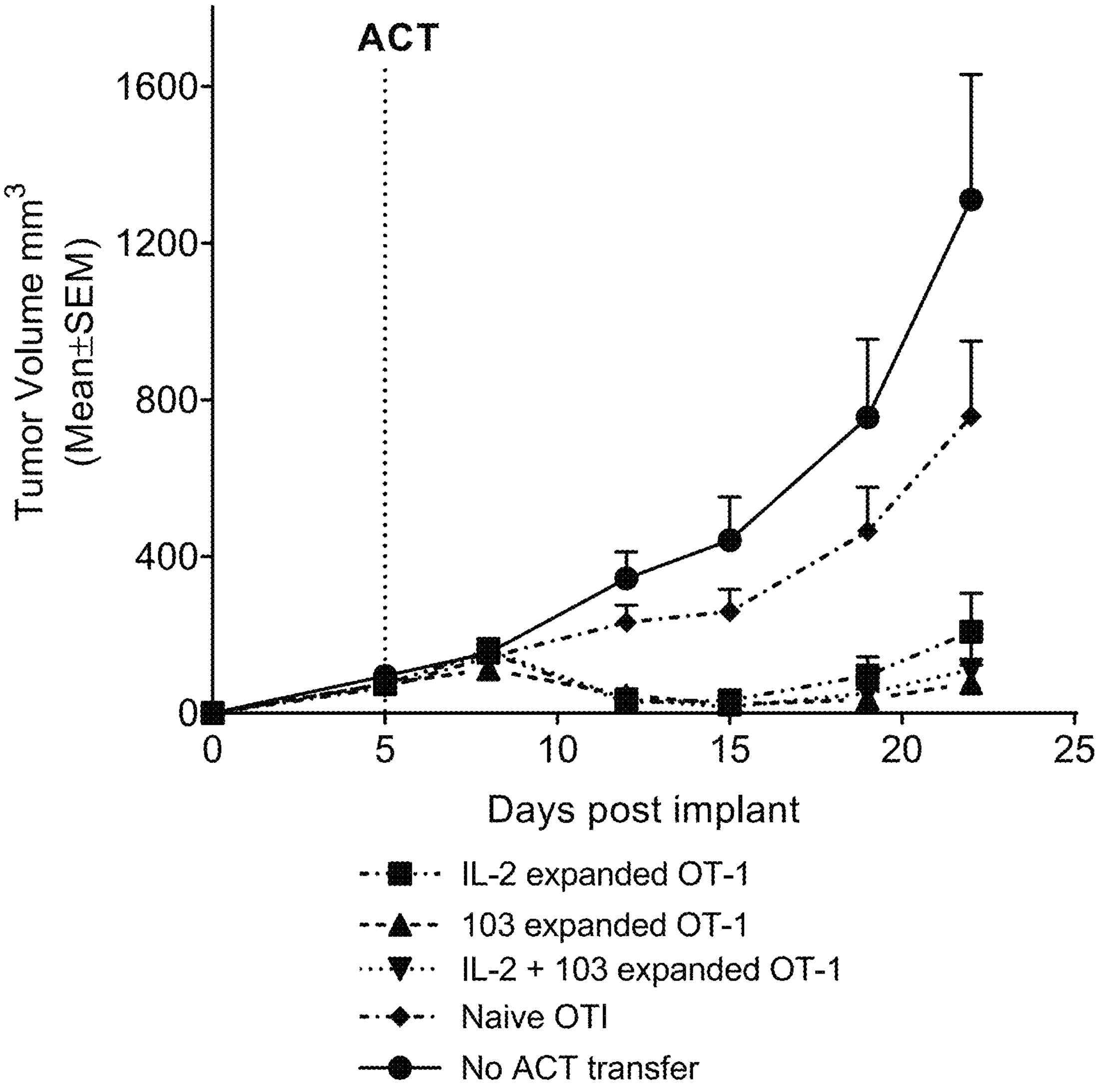
FIGS. 11A and 11B provide tumor volume over time following administration of CD8+OT-1 cells expanded with Cbl inhibitor, IL-2, Cbl inhibitor plus IL-2, and controls.
Figure 11B:
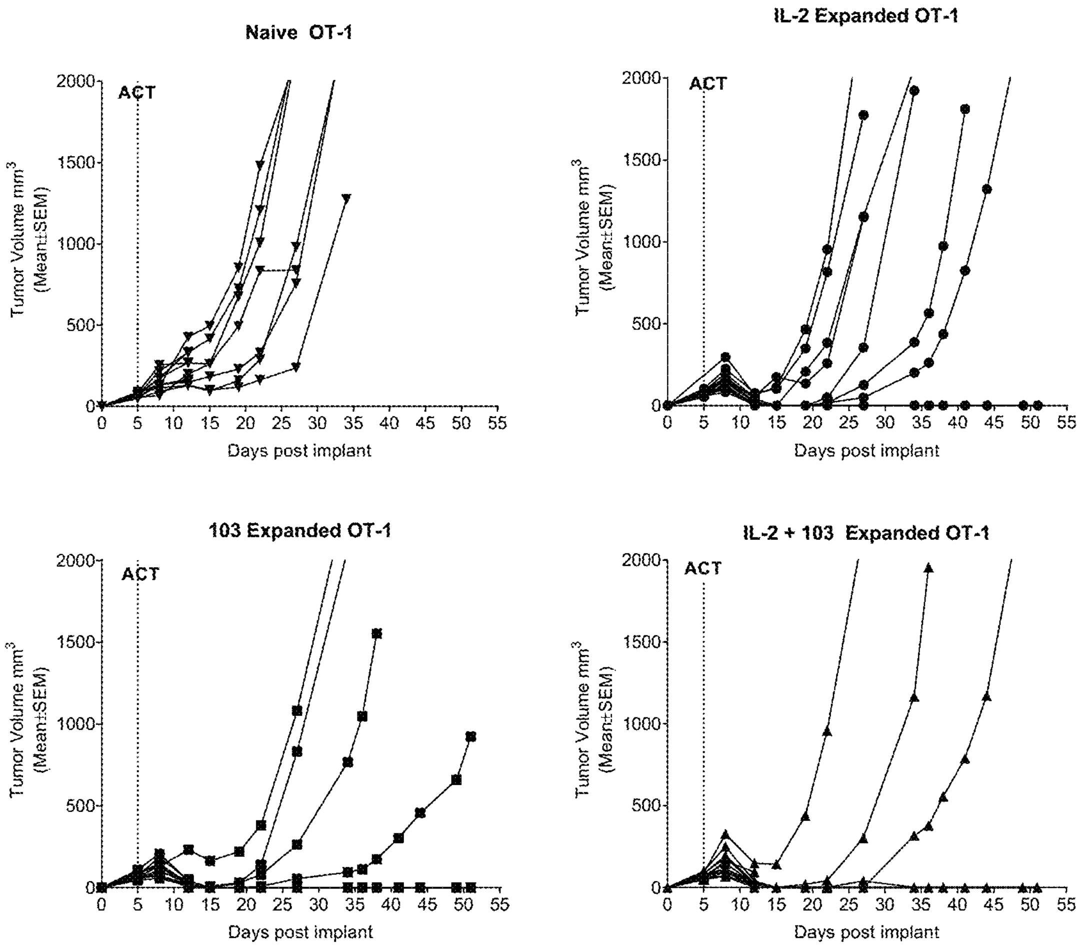

As shown in FIGS. 11A and 11B, CD8+OT-1 cells expanded with compound 103 were at least as potent as CD8+OT-1 cells expanded with IL-2. Expansion with the combination of compound 103 and IL-2 also showed similar potency through at least 20 days post implant.

In a second study shown in FIG. 12, Control cells expanded with CD3 alone demonstrated minimal antitumor activity. Cells expanded with compound 103 showed increased potency compared to IL-2 expanded cells as demonstrated by a more pronounced inhibition of tumor growth (panel A) and long term survival (B). Also, cells compound 103 plus IL-2 expanded cells showed increased potency compared to IL-2 as demonstrated by a more pronounced inhibition of tumor growth (panel A) and long term survival (B).

Figure 12A:
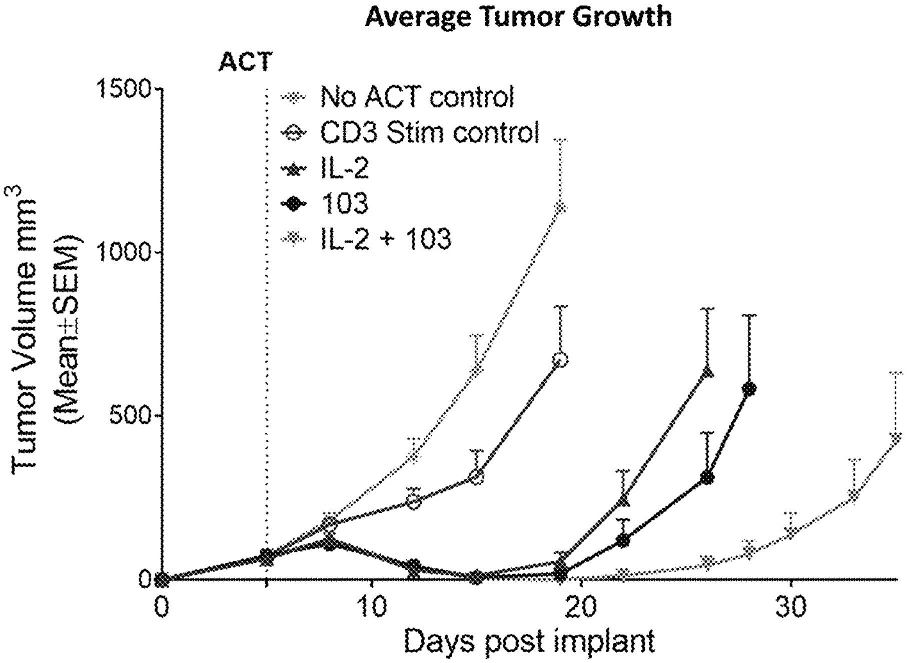
FIGS. 12A and 12B provides tumor volume over time (FIG. 12A) and conditional survival rates (FIG. 12B) following administration of anti-CD3 stimulated OT-1 cells expanded with Cbl inhibitor, IL-2, Cbl inhibitor plus IL-2, and controls.
Figure 12B:
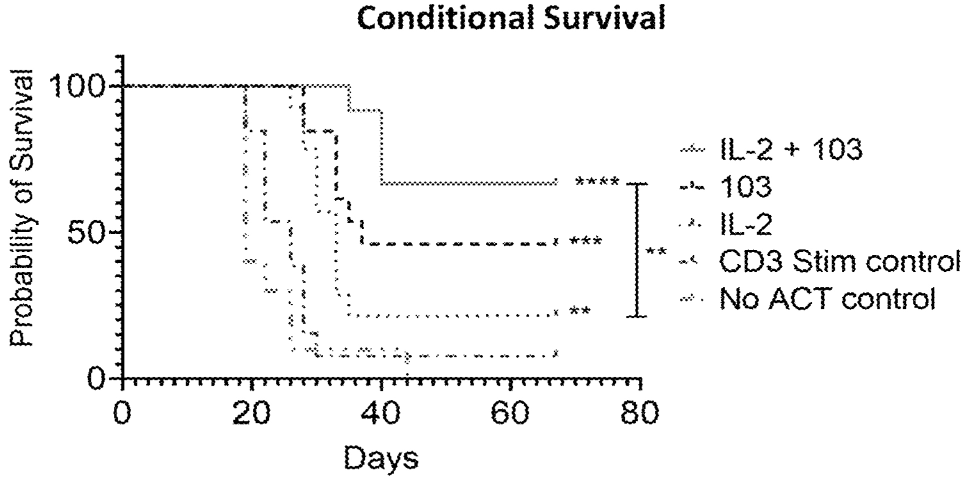

The experiment depicted in FIG. 12 demonstrates that OT-1 cells expanded with compound 103 showed increased potency compared to TL-2 expanded cells as demonstrated by a more pronounced inhibition of tumor growth (FIG. 12A) and improved long-term survival (FIG. 12B). Importantly, OT-1 cells expanded with compound 103 plus IL-2 cells showed increased potency compared to single agents alone, IL-2 or compound 103 as demonstrated by a more pronounced inhibition of tumor growth (FIG. 12 A) and superior long term survival (FIG. 12B).

Example 6: Cbl Inhibitor-Expanded Tumor Antigen Specific T Cells Demonstrate Superior Properties Compared to the Same Cells Expanded with IL-2

OT-1 cells were expanded according to the previous examples and administered to E.G7-OVA mice, which bear ovalbumin (OVA) expressing tumors. The cells were evaluated for their in vivo properties.

Figure 13A:
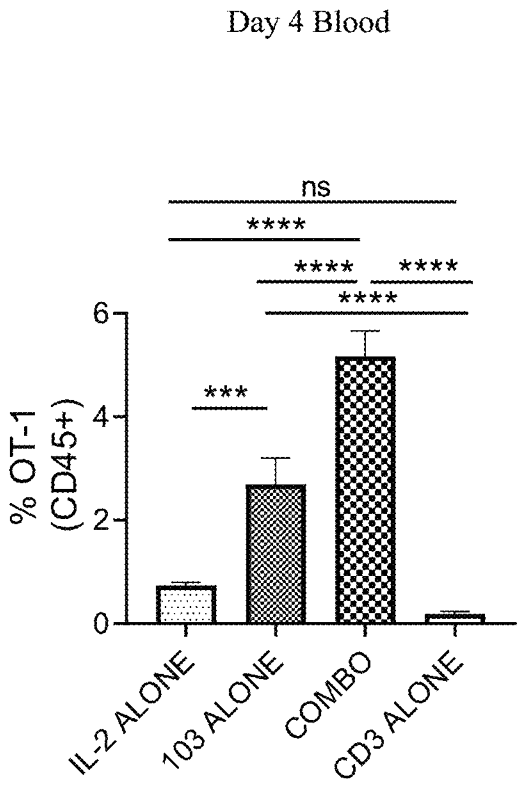
FIG. 13A (Day 4 after transfer) and FIG. 13B (Day 22 after transfer) provide frequency in total CD45+ cells and in vivo persistence in the blood of OT-1 cells expanded with and without Cbl inhibitor.
Figure 13B:
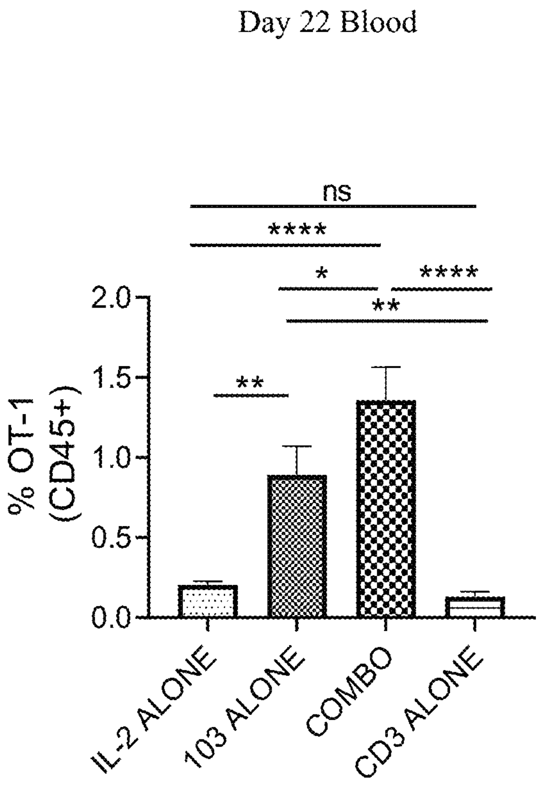

Expanded OT-1 cells were assessed in blood 4 days and 22 days after transfer. As shown in FIG. 13A (Day 4) and FIG. 13B (Day 22), Cbl inhibitor expanded cells showed higher frequency in total CD45+ cells and persisted longer than cells expanded with IL-2 alone and longer than cells expanded with anti-CD3 alone. Cells expanded with a combination of Cbl inhibitor and IL-2 showed even higher frequency in total CD45+ cells and higher persistence.

Figure 14A:
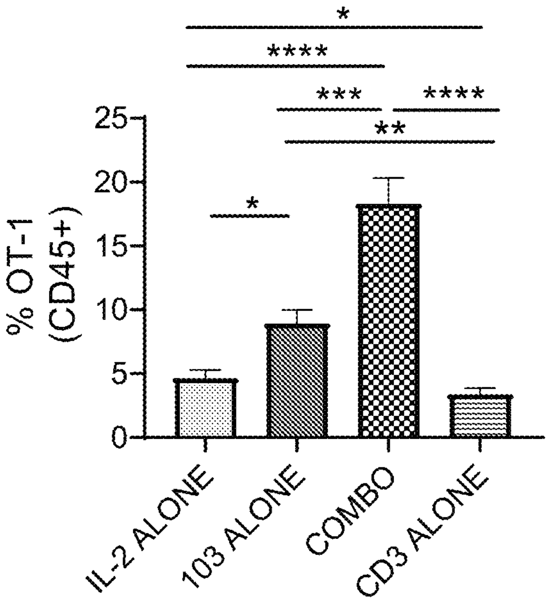
FIGS. 14A-C show the effect of a Cbl inhibitor on OT-1 cell growth.
Figure 14B:
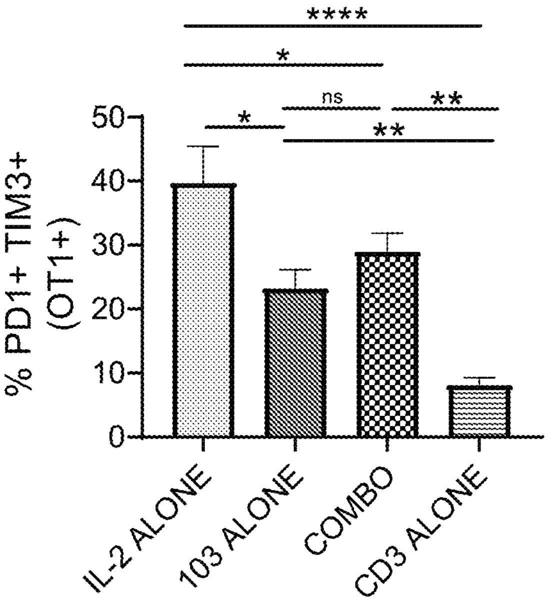
Figure 14C:
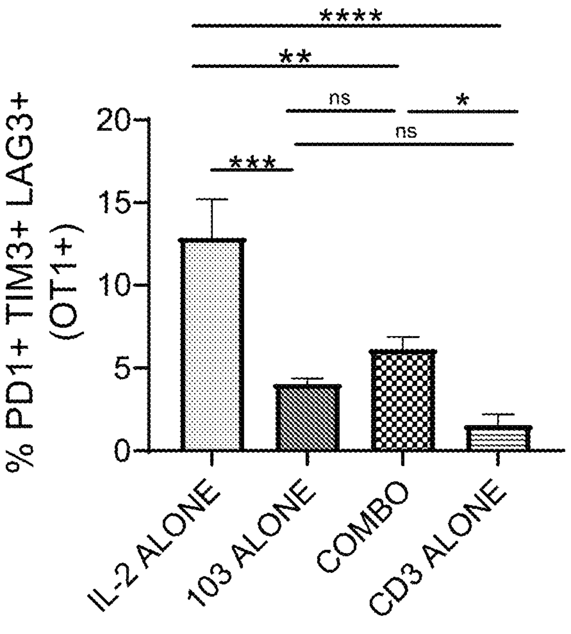

Expanded OT-1 cells were assessed in tumors 4 days after transfer. As shown in FIG. 14A, Cbl inhibitor expanded cells demonstrate an increased ability to infiltrate the tumor as shown by an higher frequency in the total CD45+ cells compared to cells expanded with IL-2 alone and cells expanded with anti-CD3 alone. Cells expanded with a combination of Cbl inhibitor and IL-2 infiltrate better tumors as demonstrated by the highest frequency in total CD45+ cells. Further, OT-1 cells expanded with Cbl inhibitor or Cbl inhibitor plus IL-2 showed lower level of expression of exhaustion markers PD1 and TIM3 (FIG. 14B) and PD1, TIM3, and LAG3 (FIG. 14C) compared to OT-1 cells expanded with IL-2 alone.

Figure 15:
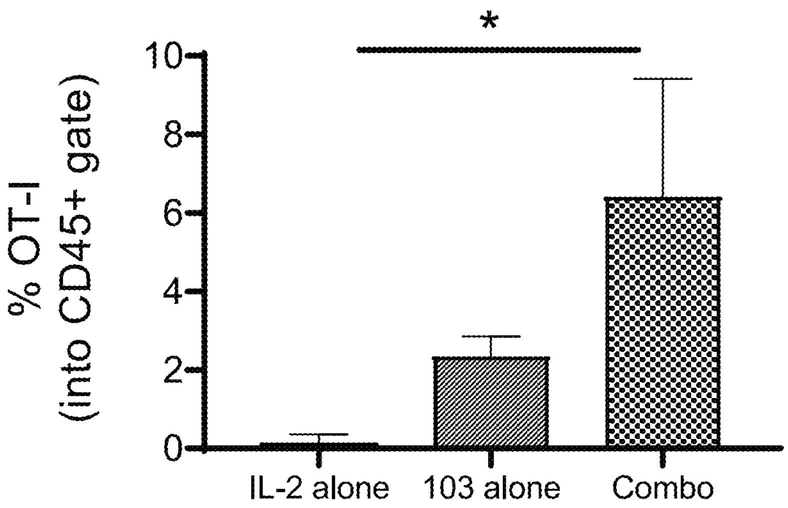
FIG. 15 provides the frequency in total CD45+ cells in response to peptide restimulation in harvested OT-1 cells expanded with and without Cbl inhibitor.

Expanded OT-1 cells were assessed from splenocytes 11 days after transfer. Harvested splenocytes were re-stimulated with OVA Class I peptide for 72 hours. As shown in FIG. 15, Cbl inhibitor expanded cells showed a superior intrinsic ability to proliferate in response to peptide restimulation compared to cells expanded with IL-2 alone. Cells expanded with a combination of Cbl inhibitor and IL-2 showed an even greater intrinsic ability to proliferate in response to peptide restimulation.

Figure 16A:
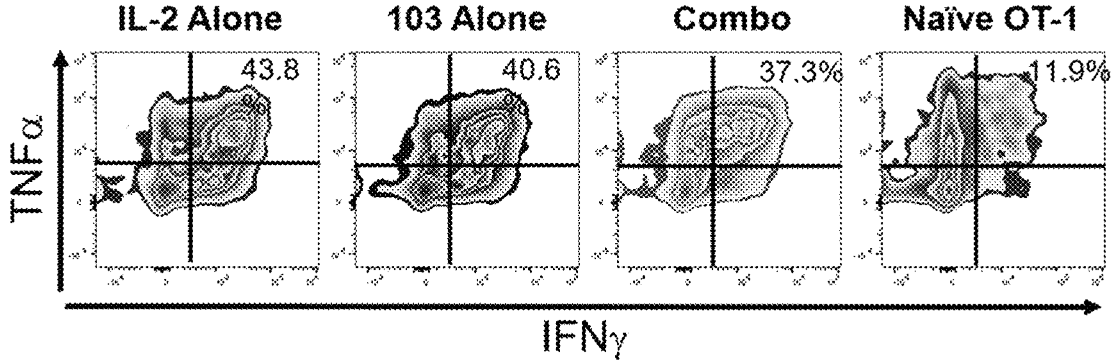
FIGS. 16A-16C show the effect of a Cbl inhibitor on OT-1 cell growth.
Figure 16B:
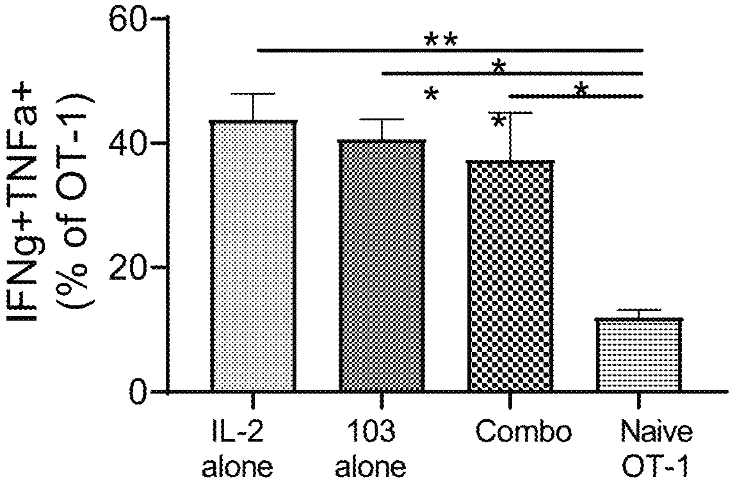
Figure 16C:
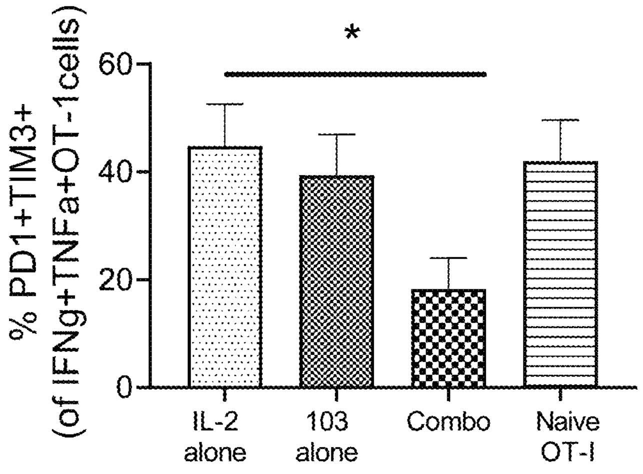

Expanded OT-1 cells were assessed from splenocytes 11 days after transfer. Harvested splenocytes were re-stimulated with OVA Class I peptide for 4 hours. As shown in FIGS. 16A and 16B, Cbl inhibitor expanded cells showed comparable multifunctionality (IFN-gamma and TNF-alpha double positive cells) in peptide-restimulated OT-1 cells compared to cells expanded with IL-2 alone. As shown in FIG. 16C, Cbl inhibitor expanded cells showed lower level of expression of exhaustion markers (PD1 and TIM3) in multifunctional (IFN-gamma and TNF-alpha double positive) cells compared to cells expanded with IL-2 alone.

Figure 17A:
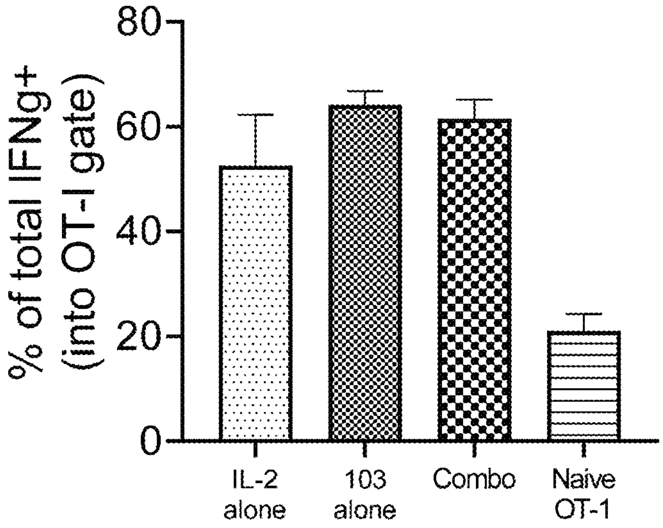
FIGS. 17A and 17B provide IFN-gamma and IL2 production in peptide-restimulated OT-1 cells harvested from splenocytes.
Figure 17B:
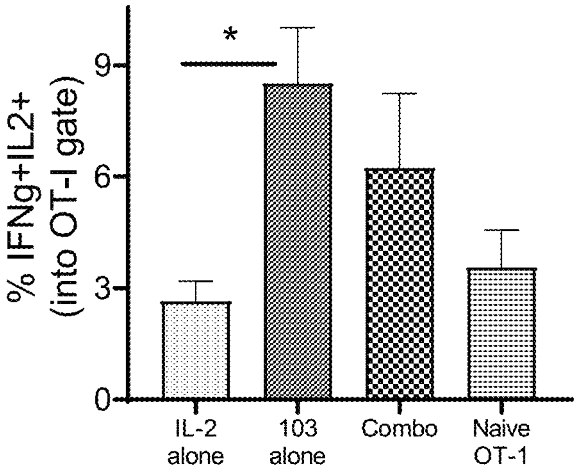

Expanded OT-1 cells were assessed from splenocytes 11 days after transfer. Harvested splenocytes were re-stimulated with OVA Class I peptide for 24 hours. IL-2 production was measured after 24 hours of peptide restimulation. As shown in FIG. 17A, expansion conditions did not affect IFN-gamma production. As shown in FIG. 17B, Cbl inhibitor expanded cells showed increased IL-2 production upon restimulation. Both total IL-2 and double IFN-g/IL-2 producing cells were increased when cells were expanded in vitro in the presence of Cbl inhibitor.

Figure 18:
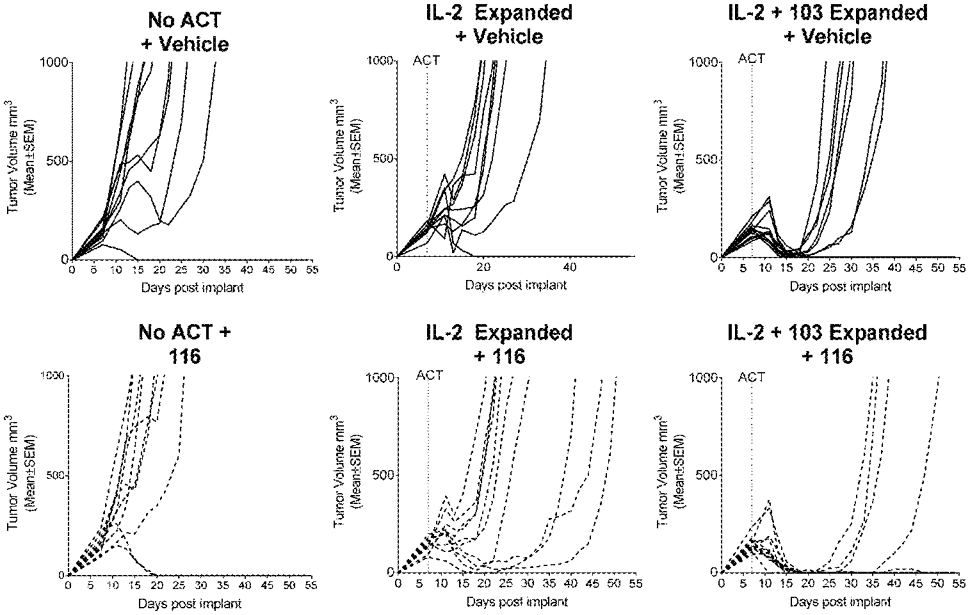
FIG. 18 provides anti-tumor efficacy of OT-1 cells expanded with IL-2 and compound 103 along with, and without, oral administration of compound 116.
Figure 19:
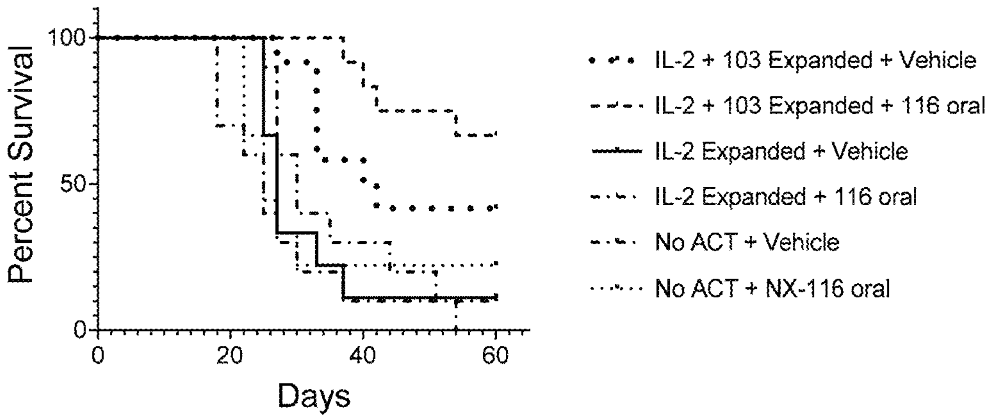
FIG. 19 provides survival of mice treated with OT-1 cells expanded with IL-2 and compound 103 along with, and without, oral administration of compound 116.

Example 7: Oral Cbl Inhibitor Treatment Enhances Anti-Tumor Efficacy of Expanded OT-1 Cells Tumor volume was measured roughly every five days after cell transfer. As shown in FIG. 18, oral administration of compound 116 enhanced the anti-tumor efficacy of OT-1 cells expanded with compound 103 plus IL-2. As shown in FIG. 19, oral administration of compound 116 enhanced survival of mice treated with OT-1 cells expanded with compound 103 plus IL-2 when compared to mice not receiving the oral treatment of compound 116.

Figure 20A:
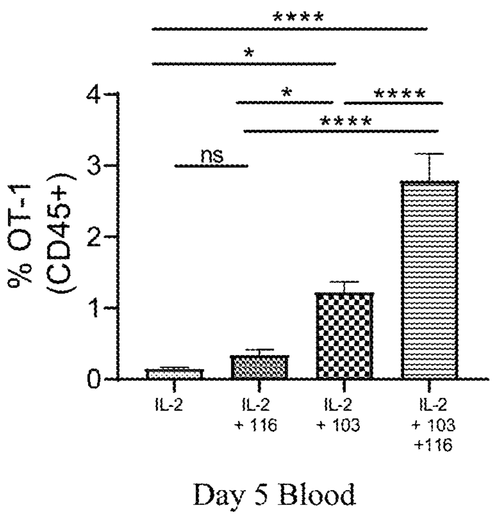
FIG. 20A (Day 5 after transfer) and 20B (Day 20 after transfer), provide frequency in total CD45+ cells and in vivo persistence of OT-1 cells expanded with IL-2 and compound 103 along with, and without, oral administration of compound 116.
Figure 20B:
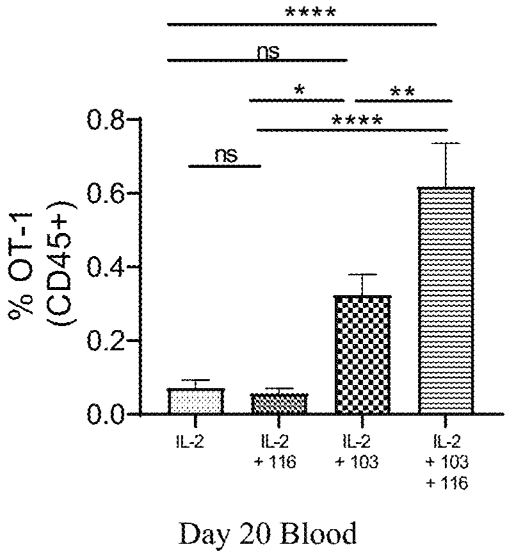

OT-1 cells were assessed in mouse blood 5 days and 20 days after transfer. As shown in FIGS. 20A and 20B, compound 116 induced increased frequency of OT-1 cells expanded with Cbl inhibitor plus IL-2. Compound 116 also induced longer persistence of OT-1 cells expanded with Cbl inhibitor plus IL-2.

Example 8: Long Term Anti-Tumor Efficacy of Expanded OT-1 Cells

Figure 21:
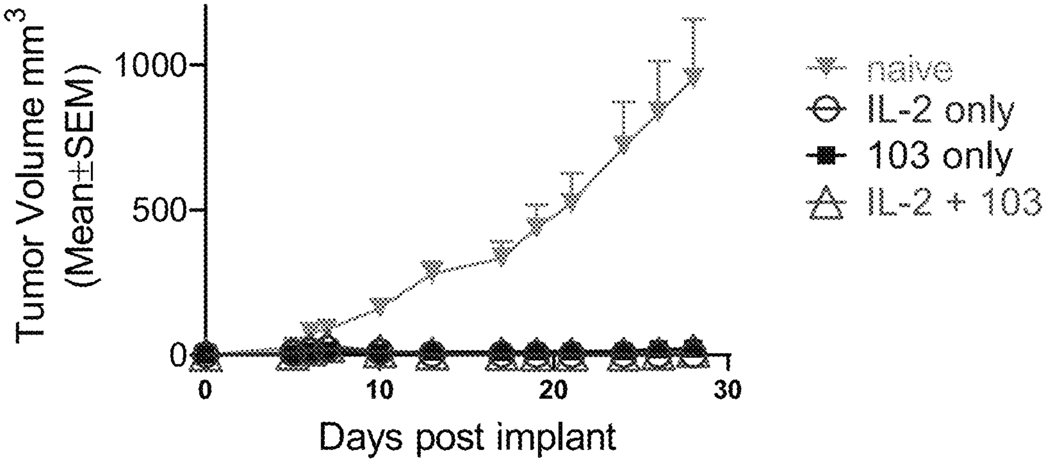
FIG. 21 demonstrates that tumor antigen specific T cells (OT-1 cells) expanded in vitro with Cbl inhibitor become potent memory cells capable of protecting mice from tumor re-challenge at a later time point.

To determine whether OT-1 cells are capable of long-term tumor protection, the long term survivors of the above experiment (FIG. 12) were re-challenged with a lethal dose of E.G7-OVA tumor cells 149 days after the initial adoptive transfer of the in vitro expanded OT-1 cells. Re-challenge induced OT-1 cell expansion at the site engrafted with E.G7-OVA tumor cells expressing ovalbumin antigen, thereby effectively controlling tumor growth (FIG. 21). Results in FIG. 21 demonstrate that mice that rejected tumors were resistant to tumor re-challenge 149 days after the initial OT-1 T cell transfer (FIG. 21).

Figure 22A:
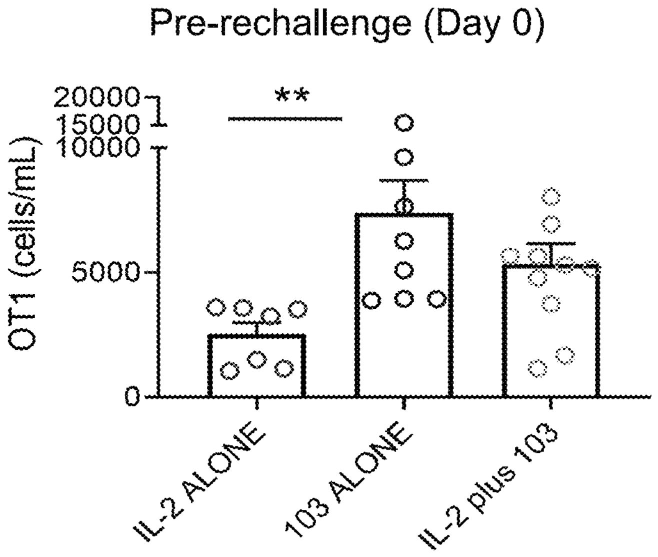
FIG. 22A provides results showing in vivo persistence of OT-1 cells expanded with IL-2 alone, Cbl inhibitor alone, and the combination IL-2 and Cbl inhibitor 149 days after the initial OT-1 T cell transfer.

To evaluate the potency of recall response, the number of OT-1 cells were assessed in blood at day 0 before the tumor re-challenge (149 days after the initial adoptive transfer) and 5 days, 12 days, 20 days, and 27 days after re-challenge. As shown in FIG. 22A, 149 days after initial adoptive transfer, OT-1 cells in vitro expanded with Cbl inhibitor or the combination of Cbl inhibitor plus IL-2 are present at a higher number in the blood, indicating a superior ability to persist in vivo.

Figure 22B:
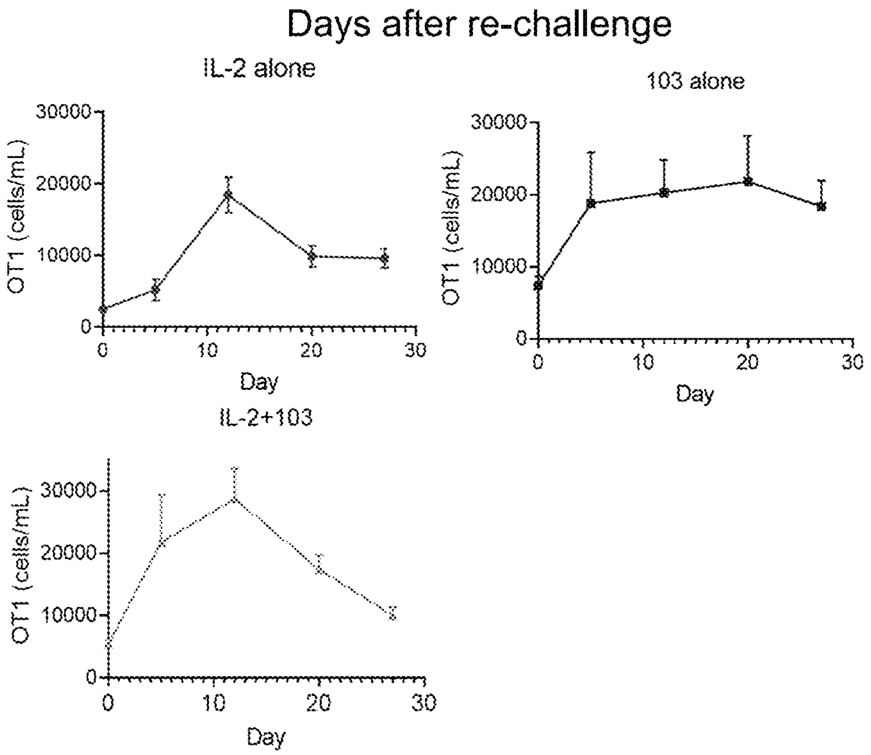
FIG. 22B provides results showing that the number of Cbl inhibitor expanded OT-1 cells increased more rapidly in the blood after tumor re-challenge.

To evaluate the recall response of the memory OT-1 cells expanded with Cbl inhibitor (alone or in combination with IL-2), the number of OT-1 cells were assessed in the blood 5 days, 12 days, 20 days, and 27 days after tumor re-challenge. As shown in FIG. 22B, OT-1 cells in vitro expanded with Cbl inhibitor, or the combination of Cbl inhibitor plus IL-2, were able to mount a significantly more rapid recall response compared to OT-1 cells expanded with IL-2 alone, as demonstrated by an higher number of OT-1 cells per ml of blood at day 5 (FIG. 22B).

Example 9: Phenotypes of Cells Expanded with Cbl Inhibitor

Cells cultured in the presence of Cbl inhibitor were characterized extensively.

Figure 23A:
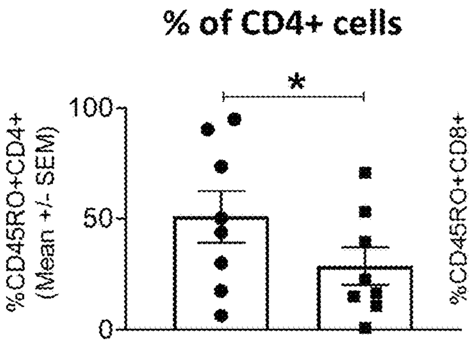
FIGS. 23A and 23B provides result showing that addition of Cbl inhibitor with IL-2 decreases CD4+ T cells and increases CD8+ cells during ex vivo TIL expansion compared to IL-2 alone in 24 well format.
Figure 23B:
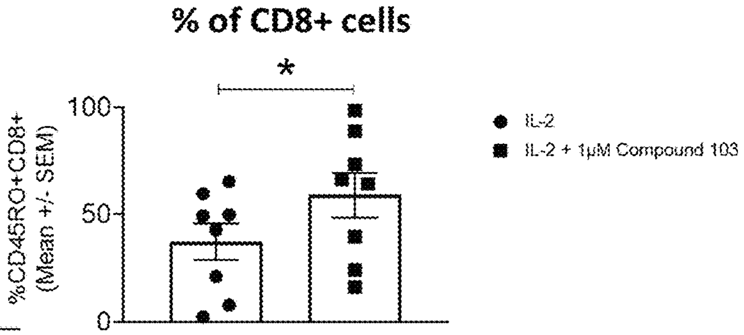

Initial studies involved TIL expansion with ovarian and CRC tumor tissues (average about 0.5-0.8 g). These were fragmented into multiple pieces (approximately 2 $mm^3$ in size), and one fragment was added per 24 well plate. These fragments were cultured in either 6000 IU IL-2 or 6000 IU IL-2+1 uM compound 103 for 28 days prior to rapid expansion (pre-REP). The wells were then pooled by treatment and total cell numbers were assessed by flow cytometry. Following TIL expansion the phenotypes of the cells were characterized. They were majority CD45RO+ and CD4+ and CD8+. In FIG. 23A, there was a decrease in the % of CD4. In FIG. 24B, there was a corresponding increase in CD8 in cells. Both were expanded with IL-2+ compound 103 in comparison to IL-2 alone. This indicates that the Cbl inhibitor selectively expands CD8 T cells in multiple tumors.

Figure 24:
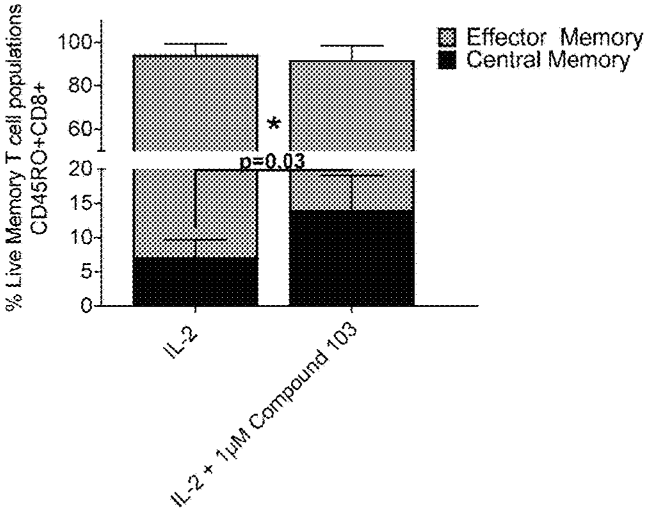
FIG. 24 provides results showing that addition of Cbl inhibitor increases CD8+ central memory T cells during ex vivo TIL expansion compared to IL-2 alone in 24 well format.

TIL directly derived from fresh ovarian and colon cancer tissues (fresh, n=8) obtained after 28 days' ex vivo culture of cancer tissue fragments were analyzed by flow cytometry. FIG. 24 provides FACS data showing percentages of central memory (CD45RO+CCR7+) and effector memory (CD45RO+CCR7−) phenotype among CD8+CD45RO+, respectively. FACS results expressed as the mean ±SEM. Statistical significance calculated using two-tailed Wilcoxon signed-rank test (*, $p<0.05$). The CD8 T cells were further characterized by assessing T cell differentiation phenotypic markers; CCR7 and CD45RO. A significant increase of central memory T cells (CCR7+CD45RO+ cells) was observed in the TIL that had been expanded with IL-2+ compound 103 in comparison to IL-2 alone (FIG. 24). This indicates the expansion of a less differentiated, persistent T cell.

Figure 25A:
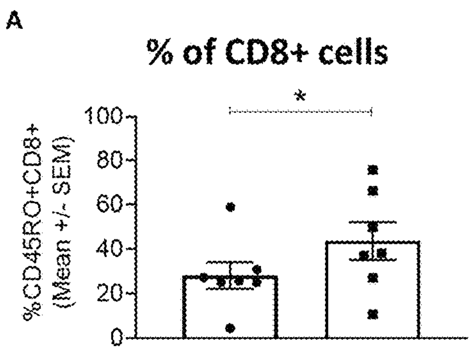
FIGS. 25A and 25B provides results indicating that Cbl inhibitor increases CD8+ cells during ex vivo TIL expansion compared to IL-2 alone in a GREX™10 format.
Figure 25B:
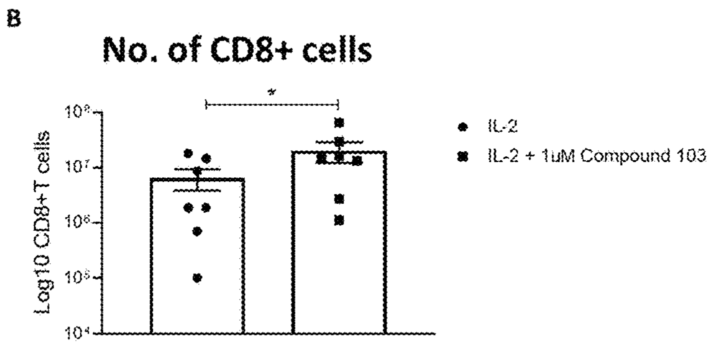

TIL directly derived from fresh ovarian, colon and breast cancer tissues (fresh, n=7) obtained after 14 days' ex vivo culture of cancer tissue fragments were analyzed by flow cytometry. Tumors were fragmented and 5 fragments were added to GREX™10 flasks containing either IL-2 or IL-2+ compound 103 in 50 ml volumes for 14 days, with cells being fed every 5 days. Focusing in on CD8 T cells, increased expansion of CD8 T cells with IL-2+ compound 103 and an increase of % CD8 T (FIG. 25A) and total numbers (FIG. 25B) were observed.

Figure 26:
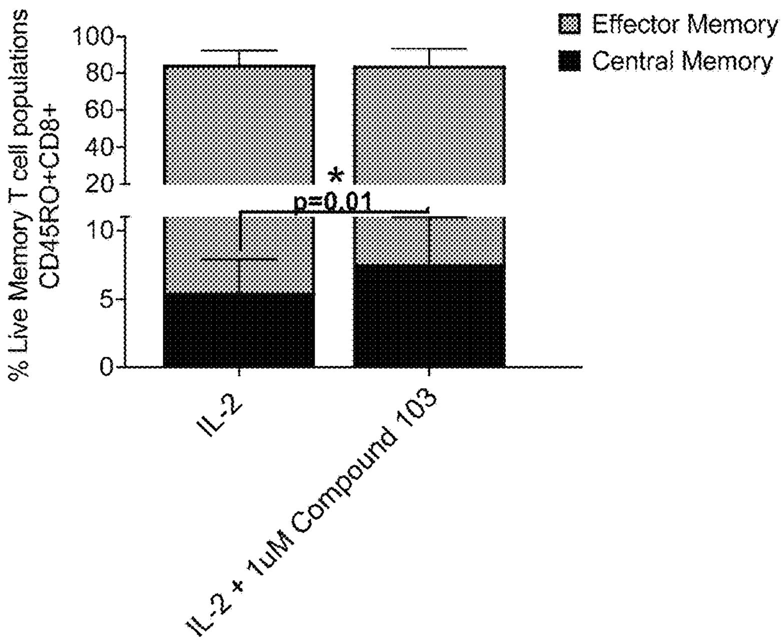
FIG. 26 provides results indicating that Cbl inhibitor increases CD8+ central memory T cells during ex vivo TIL expansion compared to IL-2 alone in GREX™10 format. Statistical significance was calculated using two-tailed Wilcoxon signed-rank test (*, $p<0.05$).

TIL directly derived from fresh ovarian, colon and breast cancer tissues (fresh, n=7) obtained after 14 days' ex vivo culture of cancer tissue fragments were analyzed by flow cytometry. FIG. 26 provides FACS data showing percentages of central memory (CD45RO+CD8+) and effector memory (CD45RO+CD8-) phenotype among CD8+ CD45RO+, respectively. FACS results were expressed as the mean SEM. This demonstrates a significant increase of central memory cells as highlighted in black.

Figure 27A:
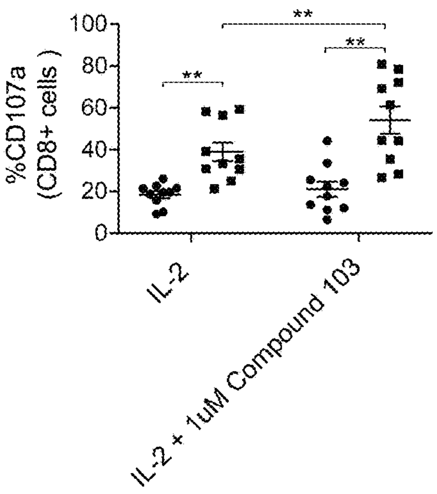
FIGS. 27A and 27B provides results indicating that pre-REP TIL expanded in GREX™10 are functional as determined by CD107a mobilization in response to non-specific stimulation. CD8+ TIL (FIG. 27A) and CD4+ (FIG. 27B) TIL derived from colon, lung, ovarian and breast (n=10) were assessed for CD107a+ expression in response to anti-CD3/antiCD28 stimulation for 6 hours in the presence of secretion inhibitors and anti-CD107a, by flow cytometry. FACS results expressed as the mean ±SEM. Statistical significance calculated using two-tailed Wilcoxon signed-rank test (*, $p<0.05$).
Figure 27B:
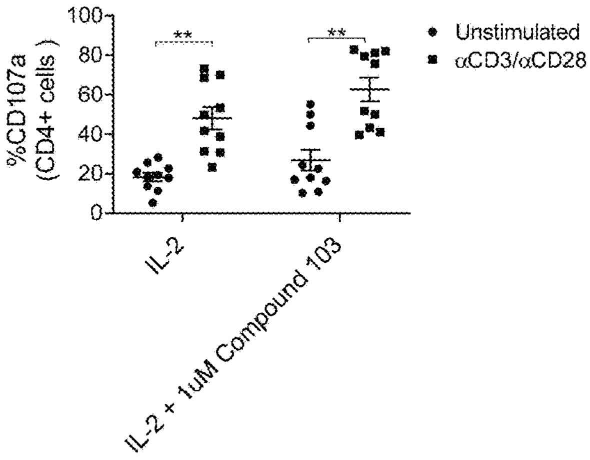

To investigate whether expanded TIL are capable of responding to extracellular stimulation, TIL were stimulated with anti-CD3/CD28 for 6 hours in the presence of secretion inhibitors and anti-CD107a. After 6 h, a clear increase was observed in surface expression of CD107a, which is associated with degranulation and cytotoxic activity of T cells. Upon stimulation, an average of 40% of $CD8^+$ TIL expanded with IL2 were positive for CD107A expression, and greater than 60% of CD8+ TIL expanded with IL2+ compound 103 were capable of producing CD107a (FIG. 27A). Upon stimulation, an average of 50% of CD4+ TIL expanded with IL2 were positive for CD107A expression, and greater than 60% of CD4+ TIL expanded with IL2+ compound 103 were capable of producing CD107a (FIG. 27B).

Figure 28A:
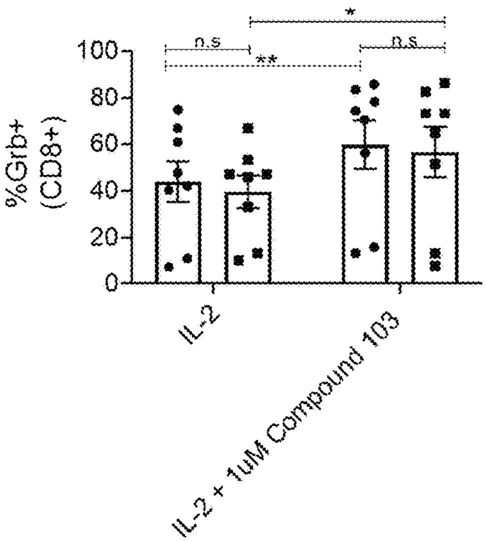
FIGS. 28A and 28B provide results indicating that pre-REP TIL expanded in GREX™10 are functional as determined by Granzyme+ secretion and Granzyme B+CD107a+ mobilization in response to non-specific stimulation. CD8+ TIL derived from colon, lung, ovarian and breast (n=10) were assessed for Granzyme B+ alone (FIG. 28A) and Granzyme B+CD107a (FIG. 28B) expression in response to anti-CD3/antiCD28 stimulation for 6 hours in the presence of secretion inhibitors by flow cytometry. FACS results were expressed as the mean ±SEM. Statistical significance was calculated using two-tailed Wilcoxon signed-rank test (*, $p<0.05$).
Figure 28B:
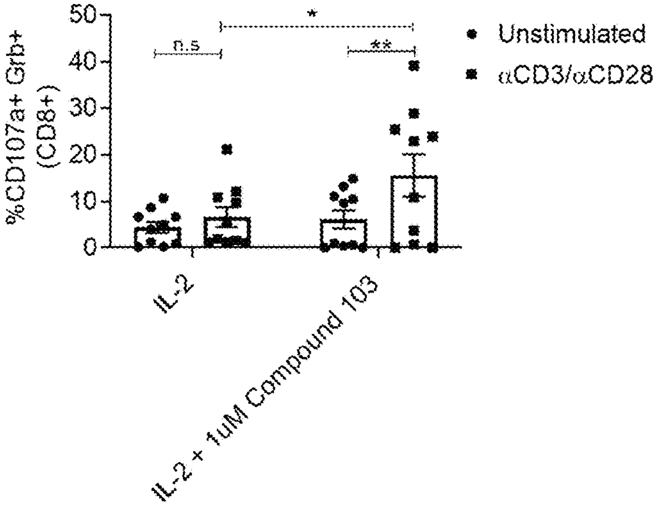

In the context of cytotoxicity, granzyme B (Grb), a protease secreted to mediate apoptosis, was assessed. Upon stimulation, there was a significant increase of Grb produced in TIL expanded with IL-2+ compound 103 in comparison to IL-2 alone (FIG. 28A). CD107A+GRB+ cells were also assessed, and again a significant increase in cells expanded with IL-2+ compound 103 was observed upon stimulation (FIG. 28B). From this, we conclude that Cbl inhibitor appears to expand TIL with increased cytotoxic potential.

Figure 29:
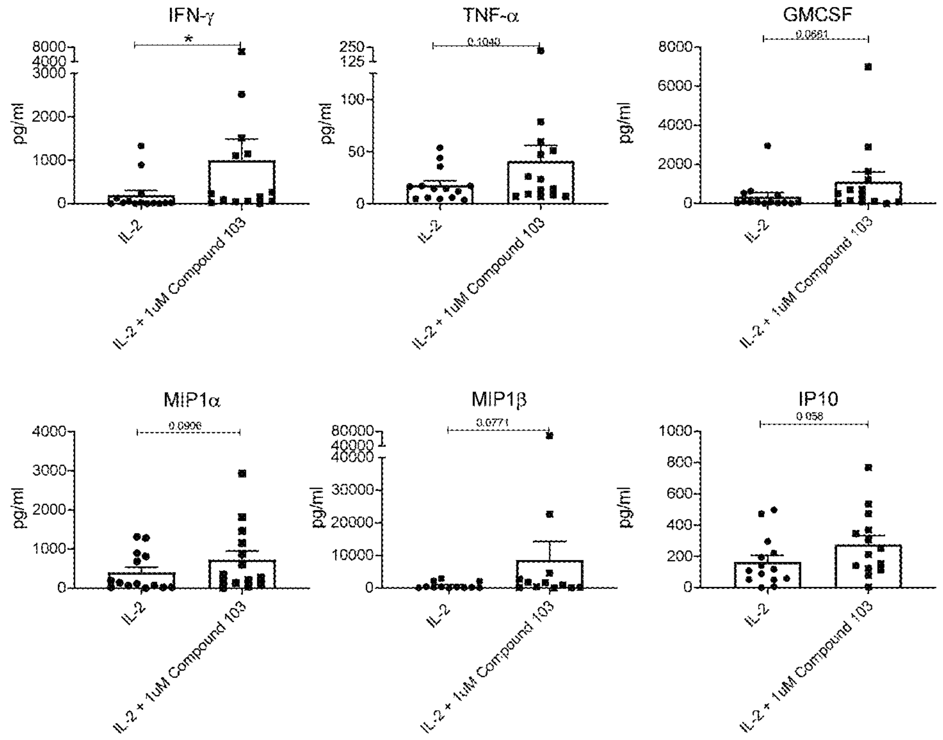
FIG. 29 provides results indicating that pre-REP expanded TIL are functional as determined by cytokine secretion in response to high dose (6000 IU/ml) IL-2 or high dose IL-2+1 uM Cbl inhibitor. Cytokines that were secreted during the 14 day expansion of TIL derived from colon, lung, ovarian and breast (n=10) were assessed using Luminex. FACS results were expressed as the mean ±SEM. Statistical significance was calculated using two-tailed Wilcoxon signed-rank test (*, $p<0.05$).

Also assessed were cytokines and chemokines secreted during the 14 day expansion in GREX™. In the flasks expanded with IL-2 + compound 103, there was significant increase of IFN-γ, with trending increases observed in GMCSF, MIP1α, MIP1β and IP10 (FIG. 29).

With addition of Cbl inhibitor, observations included increased numbers of cells, potentially better quality more persistent central memory T cells, that may be more potent in terms of it function as evidenced by cytokine secretion, and increased expression of granzyme B and degranulation marker CD107A. These support a new clinical approach for patients with solid tumor indications.

Figure 30A:
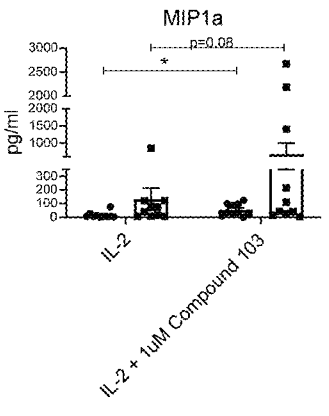
FIGS. 30A and 30B provide results indicating that TIL expanded with high dose IL-2 (6000 IU/ml) in combination with 1 μM Cbl inhibitor secrete increased T cell chemoattractants MIP1A (FIG. 30A) and MIP1B (FIG. 30B) in response to non-specific stimulation compared to IL-2 alone. FACS results were expressed as the mean ±SEM. Statistical significance was calculated using two-tailed Wilcoxon signed-rank test (*, $p<0.05$).
Figure 30B:
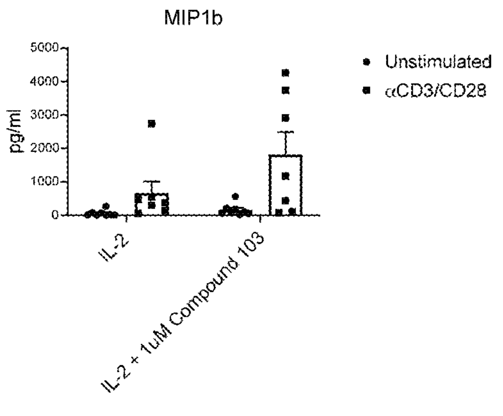

To assess chemoattractant secretion in treated cells, $1\times10^5$ TIL expanded in GREX™10 with either high dose IL-2 +/−1 μM compound 103 from multiple tumor indications (n=10) were cultured for 24 hours +/−anti-3/CD28 for 24 hours. Supernatants were assessed by Luminex. TIL expanded with IL-2 and compound 103 showed significant increases in secretion of MIP1α (FIG. 30A) and MIP1β (FIG. 30B) upon stimulation.

Figure 31:
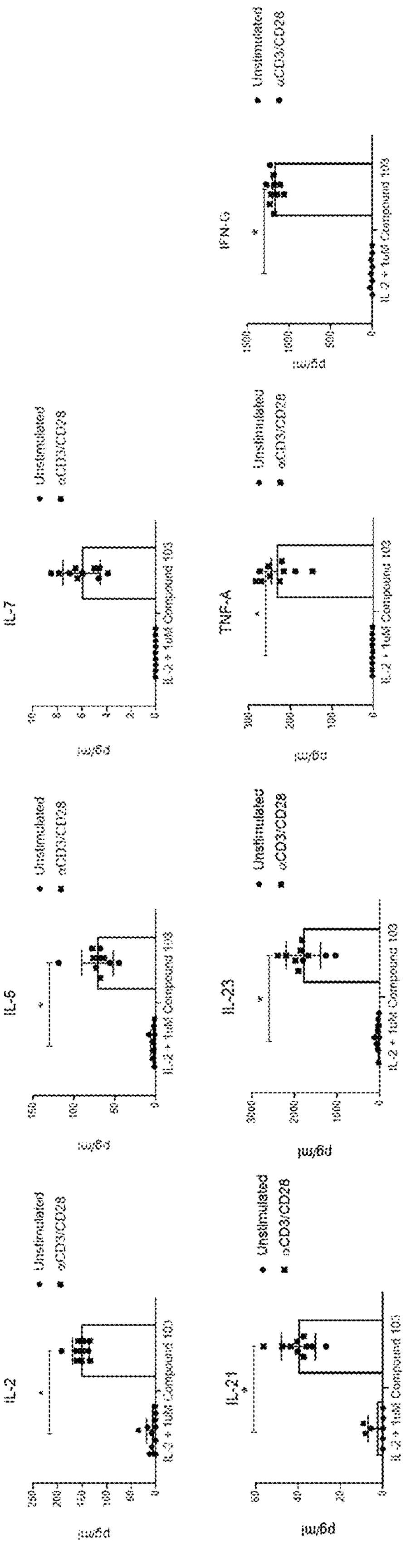
FIG. 31 provides results indicating that TIL expanded with high dose IL-2 (6000 IU/ml) and 1 μM compound 103 secrete T cell growth factor cytokines in response to non-specific stimulation. FACS results were expressed as the mean ±SEM. Statistical significance was calculated using two-tailed Wilcoxon signed-rank test (*, $p<0.05$).

To assess cytokine secretion in treated cells, $1\times10^5$ TIL expanded in GREX™10 with either high dose IL-2 +/−1 μM compound 103 from multiple tumor indications (n=10) were cultured for 24 hours +/- anti-3/CD28 for 24 hours. TIL expanded with IL-2 and compound 103 showed significant secretion of IL-2, IL-5, IL-7, IL-21, IL-23, TNF-α, and IFN-γ upon stimulation (FIG. 31).

Figures 32A, 32B, 32C:
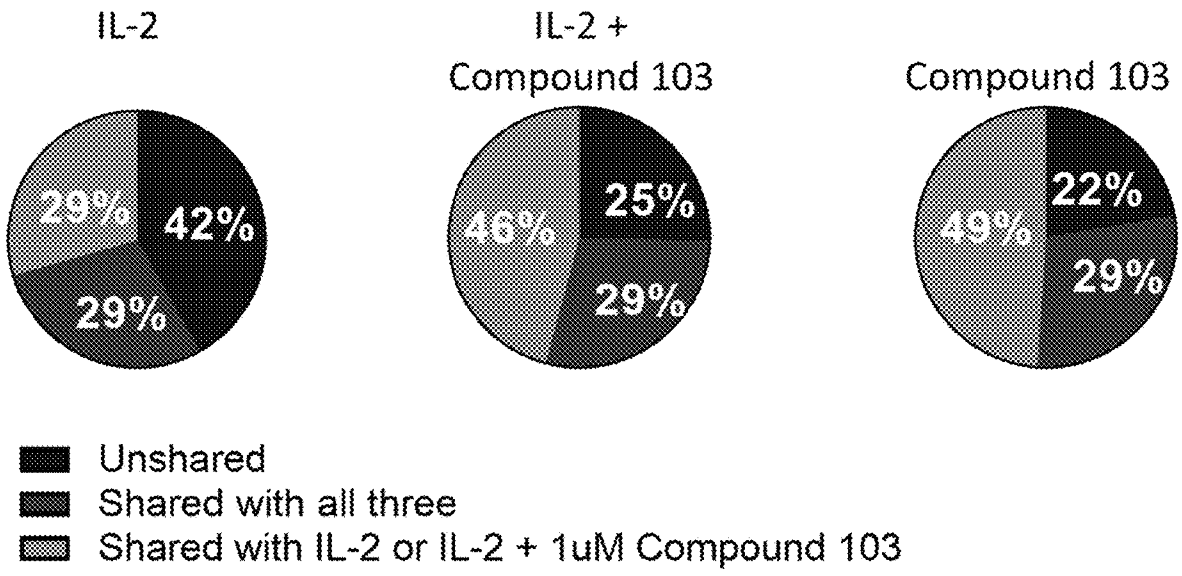
FIGS. 32A-C provides results indicating that Cbl inhibitor increases the percentage of unique CDR3s shared between treatment groups. The groups were high dose IL-2 (FIG. 32A) high dose IL-2 with compound 103 (FIG. 32B) and compound 103 alone (FIG. 32C).

To assess CDR3 diversity, representative breast TIL expanded with high dose IL-2 (FIG. 32A) high dose IL-2 with compound 103 (FIG. 32B) or compound 103 alone (FIG. 32C). TIL were cultured for 14 days in GREX™10. Total RNA of the TIL expanded with IL-2 +/−compound 103 was isolated and subjected to RT-PCR and sequencing by iRepertoire (Huntsville, AL, USA). The raw data were analyzed by iRepertoire using IRmap programs with a modified Smith-Waterman algorithm. Using CDR3algebra software, the calculation of shared CDR3s across samples with the indicated treatment was assessed. Data was filtered by the frequency of a CDR3 so that only shared CDR3 sequences with a pre-set frequency in the original data were displayed. All CDR3 frequencies were scaled to 10 million reads to account for differences in read depth among samples. Data was normalized so that each uCDR3-VDJ combination was treated as a quantity of 1 regardless of read count, and then analyzed for V usage and J usage. Unique CDR3s increased in the compound 103 groups.

Example 10: Phenotypes of Cells Expanded with Cbl Inhibitor

Figure 33:
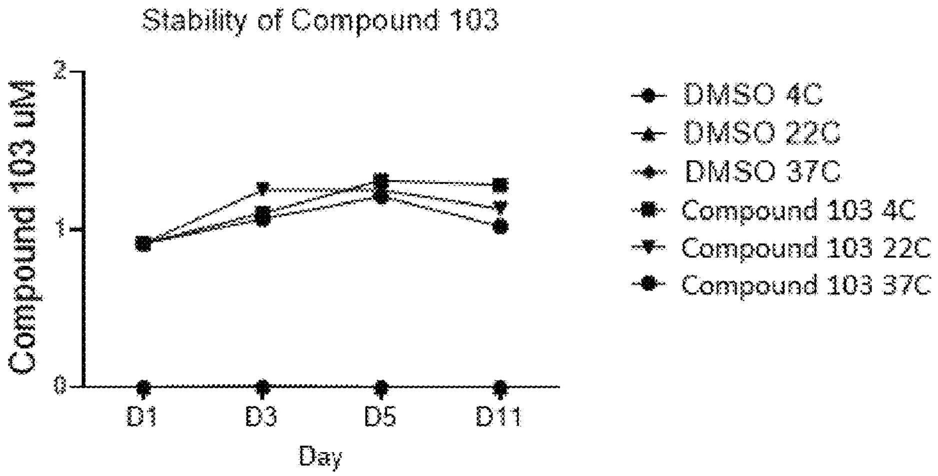
FIG. 33 provides results indicating that Cbl inhibitor compound 103 is stable at multiple temperatures (4° C.-37° C.) over an 11 day period.

To assess compound stability, at day 1, 1 μM compound 103 or DMSO was added to complete RMPI containing 10% human serum and stored at either 4° C., 22° C. or 37° C. over an 11 day time period. Concentration of compound 103 was assessed at each indicated timepoint and storage temperature by mass spectrometry. Compound 103 was stable for at least 11 days in RPMI medium (FIG. 33).

Figure 34:
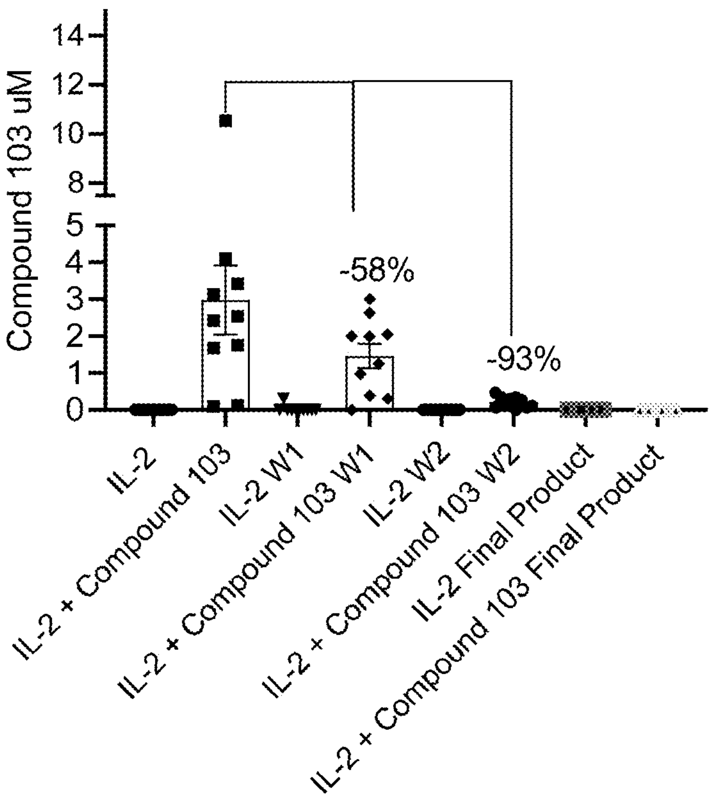
FIG. 34 provides results showing Cbl inhibitor stability in TIL culture.

To assess compound stability in culture, TIL were cultured in the presence of 1 μM compound 103, which was sequentially added every 4 days over 14 days followed by two washes in PBS (W1: Wash 1, W2: Wash 2). The amount of compound 103 was measured in the initial media, and in the resuspension buffers (W1&W2) after both sequential washes, and the cell pellet lysate (Final product) (FIG. 34). The residual amount of compound 103 was below the pharmacological effect level (PEL) for the product.

Example 11: Expansion Protocol

On Day −1, tumor tissue is harvested and fragmented. On Day 0, cells are expanded in RPMI medium with 10% serum with compound 103 and IL-2 (6000 IU). On Day 4, compound 103 is added. On Day 7, compound 103 is again added. On day 11, cells are harvested. On day 11, rapid expansion is started with the harvested cells with compound 103, IL-2 (3000 IU), and optionally OKT3 and optionally irradiated peripheral blood mononuclear cells. On day 16, compound 103 and IL-2 (3000 IU) are added. On day 22 expanded cells are harvested and ready for infusion. On day 24, cells are administered to the patient.

All publications and patent, applications cited in this specification are herein incorporated by reference as if each individual publication or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the subject matter limited solely by the scope of the following claims, including equivalents thereof.

The invention claimed is:

1. A method of producing expanded immune cells, comprising the step of:

expanding immune cells in vitro in the presence of a Cbl inhibitor in culture under conditions wherein at least $10^9$ expanded immune cells are produced in a first expansion, wherein the immune cells are tumor infiltrating lymphocytes, wherein no expansion steps are performed before the first expansion, and wherein the Cbl inhibitor is a compound of Formula (A):

Formula (A)

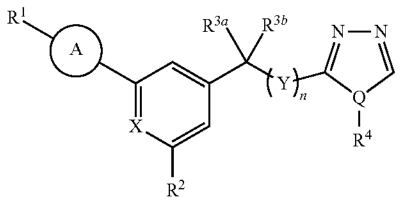

or a tautomer thereof, or a pharmaceutically acceptable salt of any of the foregoing, wherein:

$R^1$ is H, $C_1$-$C_6$ alkyl, $C_3$-$C_6$ cycloalkyl, 3-to 6-membered heterocyclyl, $C_1$-$C_6$ alkyl-($C_3$-$C_6$ cycloalkyl), $C_1$-$C_6$ alkyl-(3-to 6-membered heterocyclyl);

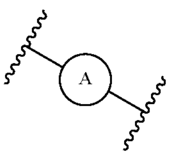

is

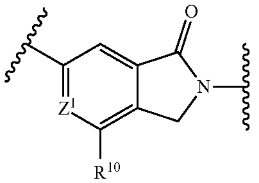

or

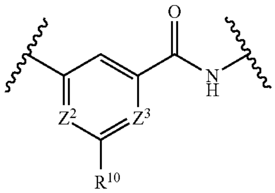

;

$Z^1$ is CH or N;

$Z^2$ is CH or N;

$Z^3$ is CH or N;

X is CH or N;

$R^2$ is H, halo, $C_3$-$C_6$ cycloalkyl, —NH-(3-to 6-membered heterocyclyl), —NH—($C_1$-$C_6$ alkyl), —NH—($C_3$-$C_6$ cycloalkyl), —O-(3-to 6-membered heterocyclyl), —O—($C_1$-$C_6$ alkyl), or —O—($C_3$-to $C_6$ cycloalkyl);

$R^{3a}$ is H, halo, or $C_1$-$C_6$ alkyl;

$R^{3b}$ is H, halo, $C_1$-$C_6$ alkyl, or $C_3$-$C_6$ cycloalkyl; or $R^{3a}$ and $R^{3b}$ are taken together with the carbon atom to which they are attached to form a 4- to 8-membered heterocyclyl or a $C_3$-$C_6$ cycloalkyl, wherein the heterocyclyl or cycloalkyl are optionally substituted by 1-3 $R^{12}$ groups;

n is 0 or 1;

Y is $C(R^{11a})(R^{11b})$ or S, with the proviso that if either or both of $R^{3a}$ and $R^{3b}$ are halo, Y is $C(R^{11a})(R^{11b})$;

Q is CH or N;

$R^4$ is H, $C_1$-$C_6$ alkyl, $C_1$-$C_6$ haloalkyl, or $C_3$-$C_6$ cycloalkyl;

$R^{10}$ is H, $C_1$-$C_6$ alkyl, $C_1$-$C_6$ haloalkyl, or $C_3$-$C_6$ cycloalkyl;

$R^{11a}$ and $R^{11b}$ are independently H, halo, $C_1$-$C_6$ alkyl, or $C_1$-$C_6$ haloalkyl; or $R^{11a}$ and $R^{11b}$ are taken together with the carbon atom to which they are attached to form a $C_3$-$C_6$ cycloalkyl; or $R^{3b}$ and $R^{11a}$ are taken together with the carbon atoms to which they are attached to form a $C_3$-$C_6$ cycloalkyl optionally substituted by $C_1$-$C_6$ alkyl; and each $R^{12}$ is independently $C_1$-$C_6$ alkyl, halo, hydroxy, —O($C_1$-$C_6$ alkyl), —CN, $C_1$-$C_6$ alkyl-CN, $C_1$-$C_6$ alkyl-OH, or $C_1$-$C_6$ haloalkyl; wherein two geminal $R^{12}$ groups can be taken together with the carbon atom to which they are attached to form a spiro $C_3$-$C_4$ cycloalkyl.

2. The method of claim 1 that comprises the first expansion step and no further expansion steps.

3. The method of claim 1 that comprises the first expansion step and one or more further expansions.

4. The method of claim 3 wherein the first expansion is for 8-12 days.

5. The method of claim 3 wherein the second expansion is for 8-12 days and there are no further expansions.

6. The method of claim 1, wherein the Cbl inhibitor is added to the culture every 3-5 days.

7. The method of claim 1, wherein the Cbl inhibitor is added to the culture on or about a day 0, a day 4, and a day 7 of the first expansion relative to culture initiation of the first expansion.

8. The method of claim 1, further comprising a second expansion step, wherein the Cbl inhibitor is added to the culture on or about a day 0 and a day 5 of the second expansion step relative to culture initiation of the second expansion step.

9. The method of claim 1, wherein the culture further comprises IL-2.

10. The method of claim 1, further comprising a second expansion, wherein IL-2 is added to the first expansion at a day 0 and to the second expansion at a day 0 and a day 5 relative to the first expansion and the second expansion, respectively.

11. The method of claim 1, wherein the culture does not comprise a component that binds to a surface receptor of the immune cells.

12. The method of claim 1, wherein the culture does not comprise anti-CD3 antibody or OKT3.

13. The method of claim 1, wherein the culture does not comprise added feeder cells.

14. The method of claim 1, wherein the culture does not comprise added irradiated peripheral blood mononuclear cells.

15. The method of claim 1, wherein the culture does not comprise added 4-IBB agonist.

16. The method of claim 1, wherein the immune cells are harvested from a donor.

17. The method of claim 1, wherein the immune cells are from a tumor or a tumor fragment.

18. The method of claim 1 that produces at least $10^{10}$ or $10^{11}$ expanded immune cells.

19. The method of claim 1, wherein the expanded immune cells are capable of use in therapy without further expansion.

20. The method of claim 1, wherein the expanded immune cells secrete a proinflammatory cytokine.

21. The method of claim 20, wherein said proinflammatory cytokine is IL-2 or IFNγ.

22. The method of claim 1, further comprising a second expansion, wherein the length of the first expansion is 0-4 days, 0-7 days, 0-11 days, 0-14 days, or 0-30 days, and/or wherein the length of the second expansion is 0-4 days, 0-7 days, 0-11 days, 0-14 days, or 0-30 days.

23. The method of claim 1, wherein the immune cells are expanded for 0-4 days, 0-7 days, 0-11 days, 0-14 days, or 0-30 days.

24. The method of claim 1, wherein the immune cells are expanded in vitro in a culture vessel comprising a gas permeable rapid expansion cell culture membrane.

25. The method of claim 1, wherein the Cbl inhibitor is at a concentration of 0.5-50 μM.

26. The method of claim 1, wherein the Cbl inhibitor inhibits activity of an enzyme selected from the group consisting of cCbl, Cbl-b, and Cbl-c.

27. The method of claim 1, wherein the Cbl inhibitor is a small molecule selected from the group consisting of compounds 101-129:

| Compound No. | Structure |
|---|---|
| 101 | 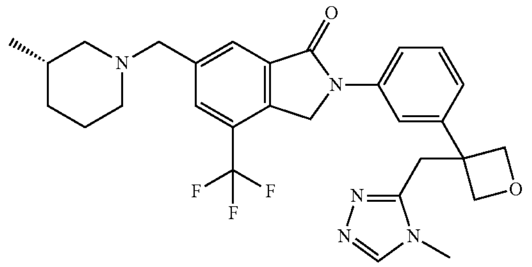 [SMILES: C[C@H]1CCCN(Cc2cc3c(c(C(F)(F)F)c2)CN(c2cccc(C4(Cc5nncn5C)COC4)c2)C3=O)C1] |
| 102 | 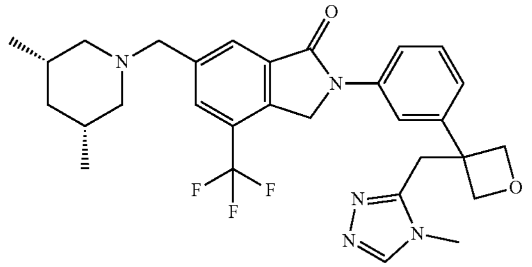 [SMILES: C[C@@H]1C[C@H](C)CN(Cc2cc3c(c(C(F)(F)F)c2)CN(c2cccc(C4(Cc5nncn5C)COC4)c2)C3=O)C1] |

-continued
| Compound No. | Structure |
| --- | --- |
| 103 | 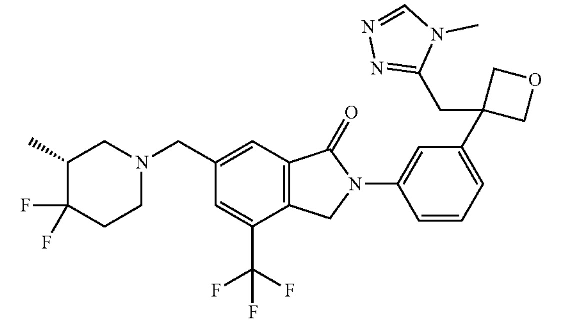 [SMILES: C[C@@H]1CN(Cc2cc3c(c(C(F)(F)F)c2)CN(c2cccc(C4(Cc5nncn5C)COC4)c2)C3=O)CCC1(F)F] |
| 104 | 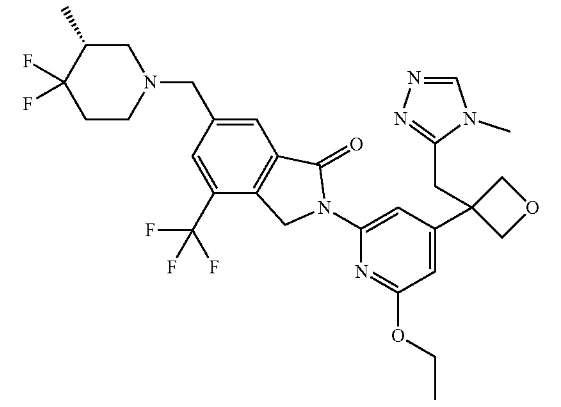 [SMILES: CCOc1cc(C2(Cc3nncn3C)COC2)cc(N2Cc3c(cc(CN4CCC(F)(F)[C@H](C)C4)cc3C(F)(F)F)C2=O)n1] |
| 105 | 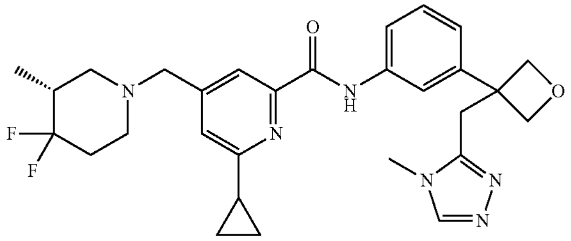 [SMILES: C[C@@H]1CN(Cc2cc(C(=O)Nc3cccc(C4(Cc5nncn5C)COC4)c3)nc(C3CC3)c2)CCC1(F)F] |
| 106 | 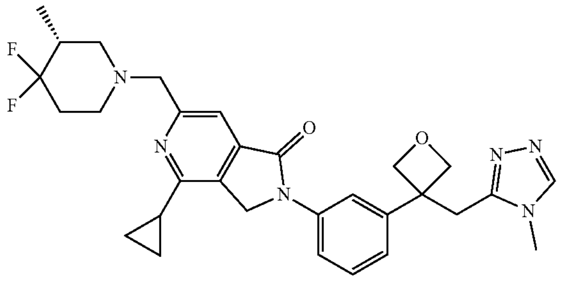 [SMILES: C[C@@H]1CN(Cc2cc3c(c(C4CC4)n2)CN(c2cccc(C4(Cc5nncn5C)COC4)c2)C3=O)CCC1(F)F] |

-continued
| Compound No. | Structure |
|---|---|
| 107 | 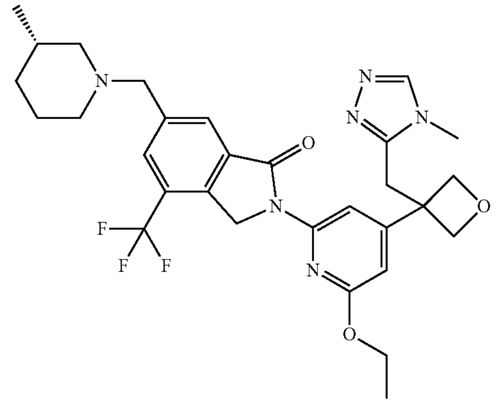 [SMILES: CCOc1cc(C2(Cc3nncn3C)COC2)cc(N2Cc3c(cc(CN4CCC[C@H](C)C4)cc3C(F)(F)F)C2=O)n1] |
| 108 | 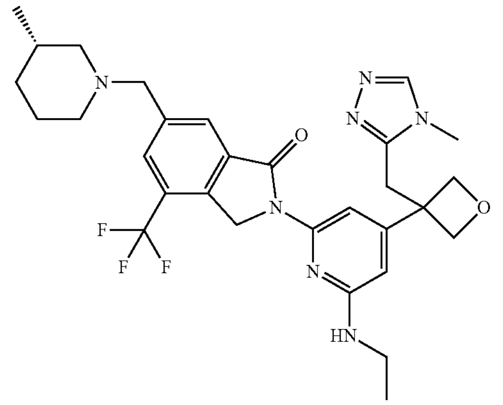 [SMILES: CCNc1cc(C2(Cc3nncn3C)COC2)cc(N2Cc3c(cc(CN4CCC[C@H](C)C4)cc3C(F)(F)F)C2=O)n1] |
| 109 | 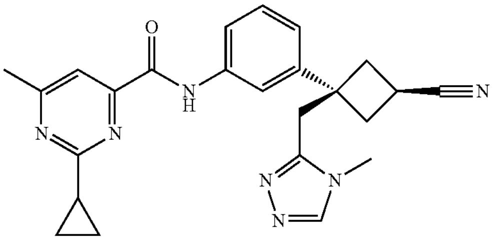 [SMILES: Cc1cc(C(=O)Nc2cccc([C@]3(Cc4nncn4C)C[C@@H](C#N)C3)c2)nc(C2CC2)n1] |
| 110 | 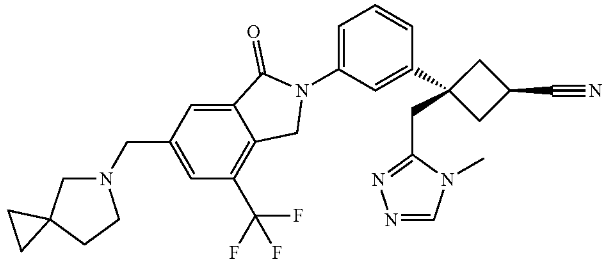 [SMILES: Cn1cnnc1C[C@]1(c2cccc(N3Cc4c(cc(CN5CCC6(CC6)C5)cc4C(F)(F)F)C3=O)c2)C[C@H](C#N)C1] |

-continued
| Compound No. | Structure |
|---|---|
| 111 | 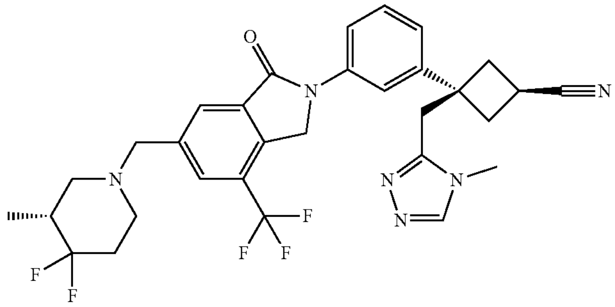 [SMILES: C[C@@H]1CN(Cc2cc3c(c(C(F)(F)F)c2)CN(c2cccc([C@]4(Cc5nncn5C)C[C@@H](C#N)C4)c2)C3=O)CCC1(F)F] |
| 112 | 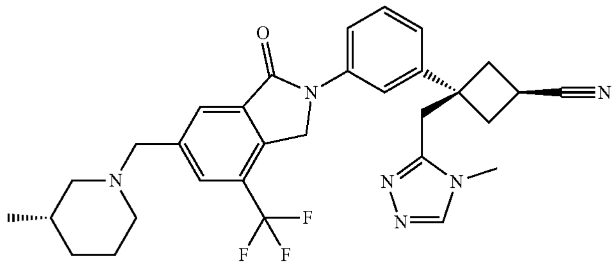 [SMILES: C[C@H]1CCCN(Cc2cc3c(c(C(F)(F)F)c2)CN(c2cccc([C@]4(Cc5nncn5C)C[C@@H](C#N)C4)c2)C3=O)C1] |
| 113 | 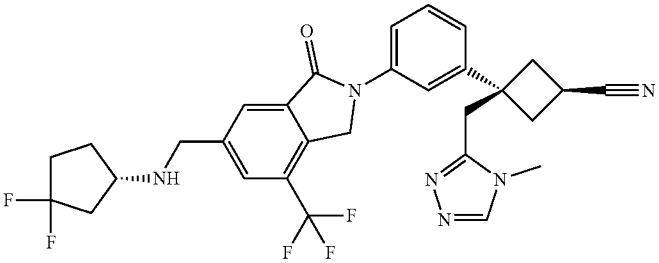 [SMILES: Cn1cnnc1C[C@]1(c2cccc(N3Cc4c(cc(CN[C@H]5CCC(F)(F)C5)cc4C(F)(F)F)C3=O)c2)C[C@H](C#N)C1] |
| 114 | 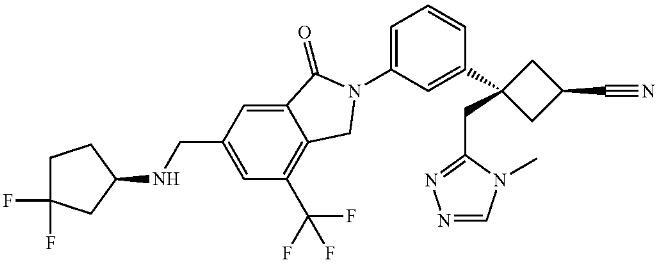 [SMILES: Cn1cnnc1C[C@]1(c2cccc(N3Cc4c(cc(CN[C@@H]5CCC(F)(F)C5)cc4C(F)(F)F)C3=O)c2)C[C@H](C#N)C1] |
| 115 | 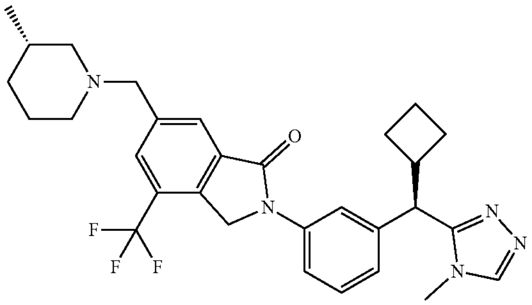 [SMILES: C[C@H]1CCCN(Cc2cc3c(c(C(F)(F)F)c2)CN(c2cccc([C@H](c4nncn4C)C4CCC4)c2)C3=O)C1] |

-continued
| Compound No. | Structure |
|---|---|
| 116 | 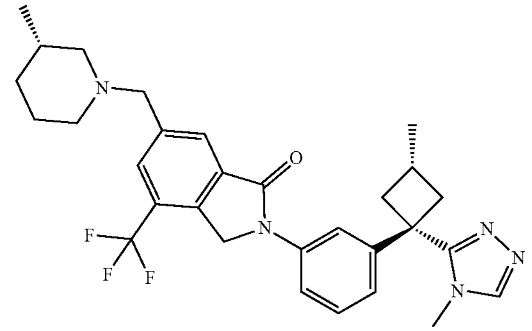 [SMILES: C[C@H]1CCCN(Cc2cc3c(c(C(F)(F)F)c2)CN(c2cccc([C@]4(c5nncn5C)C[C@@H](C)C4)c2)C3=O)C1] |
| 117 | 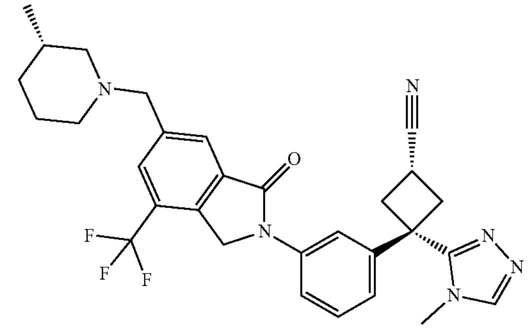 [SMILES: C[C@H]1CCCN(Cc2cc3c(c(C(F)(F)F)c2)CN(c2cccc([C@]4(c5nncn5C)C[C@@H](C#N)C4)c2)C3=O)C1] |
| 118 | 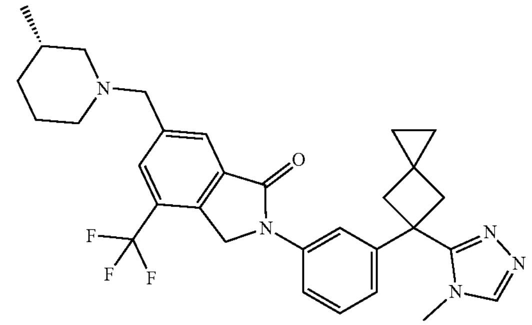 [SMILES: C[C@H]1CCCN(Cc2cc3c(c(C(F)(F)F)c2)CN(c2cccc(C4(c5nncn5C)CC5(CC5)C4)c2)C3=O)C1] |
| 119 | 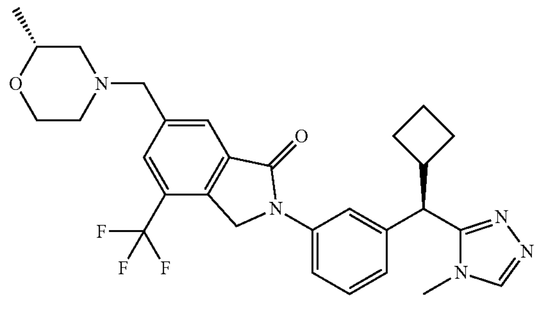 [SMILES: C[C@@H]1CN(Cc2cc3c(c(C(F)(F)F)c2)CN(c2cccc([C@H](c4nncn4C)C4CCC4)c2)C3=O)CCO1] |

-continued
| Compound No. | Structure |
|---|---|
| 120 | 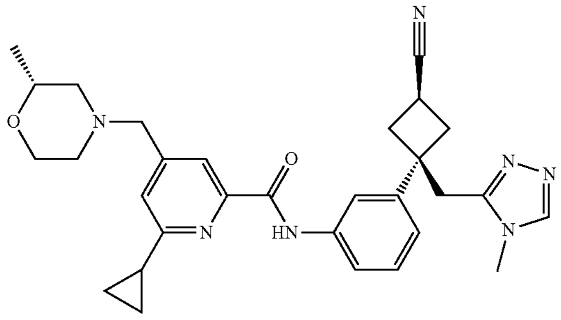 [SMILES: C[C@@H]1CN(Cc2cc(C(=O)Nc3cccc([C@]4(Cc5nncn5C)C[C@@H](C#N)C4)c3)nc(C3CC3)c2)CCO1] |
| 121 | 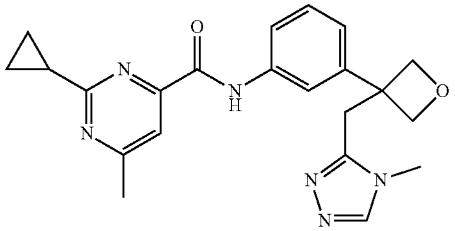 [SMILES: Cc1cc(C(=O)Nc2cccc(C3(Cc4nncn4C)COC3)c2)nc(C2CC2)n1] |
| 122 | 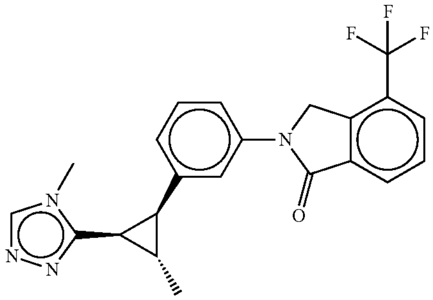 |
| 123 | 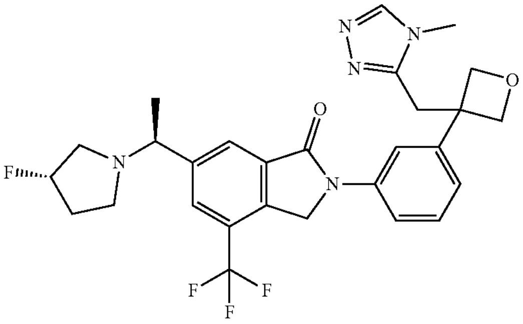 [SMILES: C[C@@H](c1cc2c(c(C(F)(F)F)c1)CN(c1cccc(C3(Cc4nncn4C)COC3)c1)C2=O)N1CC[C@H](F)C1] |
| 124 | 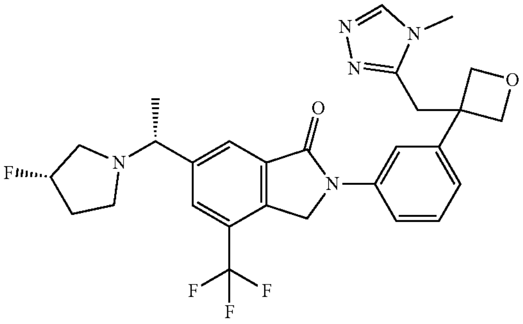 [SMILES: C[C@H](c1cc2c(c(C(F)(F)F)c1)CN(c1cccc(C3(Cc4nncn4C)COC3)c1)C2=O)N1CC[C@H](F)C1] |

-continued
| Compound No. | Structure |
|---|---|
| 125 | 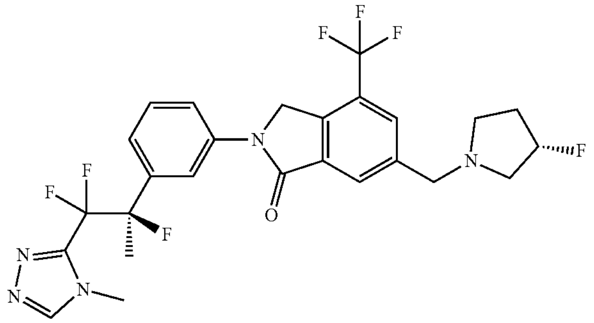 [SMILES: Cn1cnnc1C(F)(F)[C@](C)(F)c1cccc(N2Cc3c(cc(CN4CC[C@H](F)C4)cc3C(F)(F)F)C2=O)c1] |
| 126 | 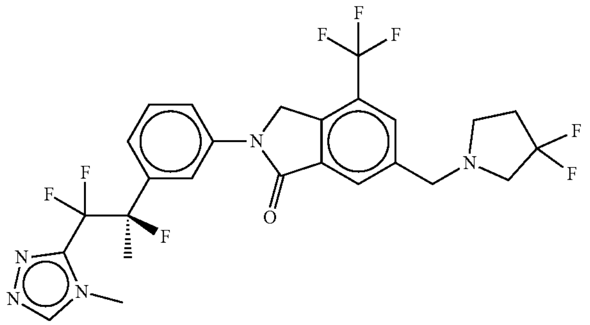 |
| 127 | 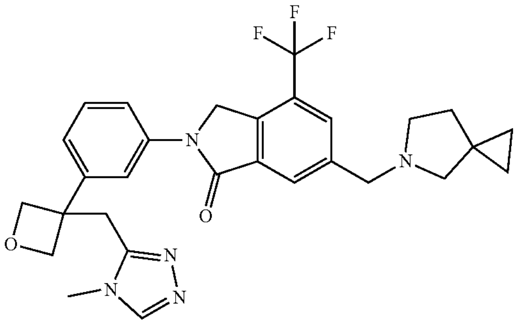 [SMILES: Cn1cnnc1CC1(c2cccc(N3Cc4c(cc(CN5CCC6(CC6)C5)cc4C(F)(F)F)C3=O)c2)COC1] |
| 128 | 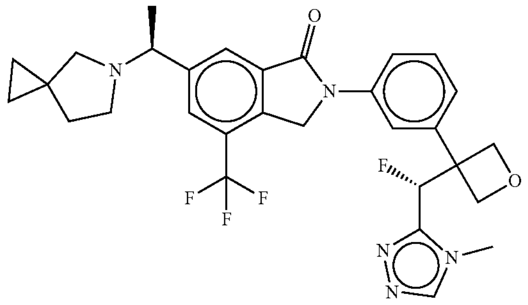 |

-continued

| Compound No. | Structure |
| --- | --- |
| 129 | 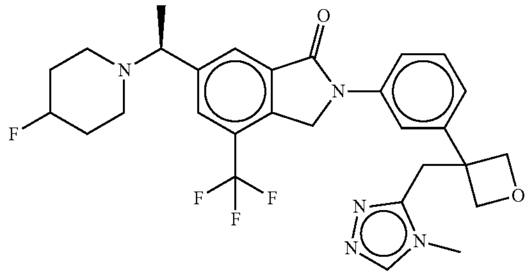 |

28. A composition comprising expanded immune cells produced by the method of claim 1.

29. A method of treating T cell dysfunction in a patient in need thereof, comprising administering to the patient an effective amount of the composition of claim 28.

30. A method of treating cancer in a patient in need thereof, comprising administering to the patient an effective amount of the composition of claim 28.

31. The method of claim 30, further comprising administering to the patient a Cbl inhibitor, or a salt or pharmaceutically acceptable composition thereof, in an amount effective to enhance the treatment.

* * * * *